(12) United States Patent
Iakovlev et al.

(10) Patent No.: US 12,202,906 B2
(45) Date of Patent: Jan. 21, 2025

(54) MONOCLONAL ANTIBODY THAT SPECIFICALLY BINDS TO CD20

(71) Applicant: JOINT STOCK COMPANY "BIOCAD", St.Petersburg (RU)

(72) Inventors: Pavel Andreevich Iakovlev, St.Petersburg (RU); Natalia Eugenievna Pestova, St.Petersburg (RU); Arina Vitalevna Anikina, Moscow (RU); Anna Alexandrovna Trudovishnikova, g. Chekhov (RU); Mariia Aleksandrovna Shchemeleva, St.Petersburg (RU); Nina Grachyaevna Kharatian, St.Petersburg (RU); Valery Vladimirovich Solovyev, Pushchino (RU); Alexey Konstantinovich Misorin, St.Petersburg (RU); Sergei Vasilyevich Diduk, Klimovsk (RU); Anna Vladimirovna Eroshova, p.Bohan (RU); Veronika Sergeevna Usatova, g.Borovichi (RU); Elena Andreevna Krendeleva, St.Petersburg (RU); Iakov Iurevich Ustiugov, Berezniki (RU); Aleksei Aleksandrovich Aleksandrov, Perm (RU); Iana Andreevna Smirnova, Moscow (RU); Svetlana Vladimirovna Koskova, St.Petersburg (RU); Roman Alekseevich Ivanov, Moscow (RU); Dmitry Valentinovich Morozov, St.Petersburg (RU)

( * ) Notice: Subject to any disclaimer, the term of this patent is extended or adjusted under 35 U.S.C. 154(b) by 920 days.

(21) Appl. No.: 17/288,234

(22) PCT Filed: Oct. 30, 2019

(86) PCT No.: PCT/RU2019/050205
§ 371 (c)(1),
(2) Date: Apr. 23, 2021

(87) PCT Pub. No.: WO2020/091634
PCT Pub. Date: May 7, 2020

(65) Prior Publication Data
US 2022/0089761 A1 Mar. 24, 2022

(30) Foreign Application Priority Data
Oct. 31, 2018 (RU) .......................... RU2018138510

(51) Int. Cl.
*A61K 39/395* (2006.01)
*A61P 35/02* (2006.01)
*C07K 16/28* (2006.01)
*C12N 15/63* (2006.01)
*A61K 39/00* (2006.01)

(52) U.S. Cl.
CPC ...... *C07K 16/2887* (2013.01); *A61K 39/3955* (2013.01); *A61P 35/02* (2018.01); *C12N 15/63* (2013.01); *A61K 2039/505* (2013.01); *C07K 2317/24* (2013.01); *C07K 2317/55* (2013.01); *C07K 2317/732* (2013.01); *C07K 2317/734* (2013.01); *C07K 2317/92* (2013.01)

(58) Field of Classification Search
CPC .............. A61K 39/3955; A61K 39/395; C07K 16/2887; C07K 16/28
See application file for complete search history.

(56) References Cited

U.S. PATENT DOCUMENTS

| | | |
|---|---|---|
| 4,120,649 A | 10/1978 | Schechter |
| 4,399,216 A | 8/1983 | Axel et al. |
| 4,510,245 A | 4/1985 | Cousens et al. |
| 4,634,665 A | 1/1987 | Axel et al. |
| 4,665,077 A | 5/1987 | Stringfellow et al. |
| 4,740,461 A | 4/1988 | Kaufman |
| 4,816,567 A | 3/1989 | Cabilly et al. |
| 4,912,040 A | 3/1990 | Kaufman et al. |
| 4,959,455 A | 9/1990 | Clark et al. |
| 4,968,615 A | 11/1990 | Koszinowski et al. |
| 5,114,721 A | 5/1992 | Cohen et al. |
| 5,168,062 A | 12/1992 | Stinski |
| 5,179,017 A | 1/1993 | Axel et al. |
| 5,229,275 A | 7/1993 | Goroff |
| 5,500,362 A | 3/1996 | Robinson et al. |
| 5,545,806 A | 8/1996 | Lonberg et al. |
| 5,545,807 A | 8/1996 | Surani et al. |
| 5,567,610 A | 10/1996 | Borrebaeck et al. |

(Continued)

FOREIGN PATENT DOCUMENTS

| | | |
|---|---|---|
| AU | 2017202590 A1 | 5/2017 |
| CN | 102167744 A | 8/2011 |

(Continued)

OTHER PUBLICATIONS

Related International Application No. PCT/RU2019/050205 International Search Report dated Mar. 12, 2020 with its translations.

(Continued)

*Primary Examiner* — Xiaozhen Xie
(74) *Attorney, Agent, or Firm* — Anglehart et al.

(57) ABSTRACT

The present invention relates to biotechnology and provides a monoclonal antibody that specifically binds to CD20. The invention also relates to DNA encoding said antibody, the corresponding expression vectors and methods of production thereof, as well as methods of treatment using said antibody.

14 Claims, 35 Drawing Sheets
Specification includes a Sequence Listing.

(56) References Cited

U.S. PATENT DOCUMENTS

| | | | |
|---|---|---|---|
| 5,569,825 | A | 10/1996 | Lonberg et al. |
| 5,571,894 | A | 11/1996 | Wells et al. |
| 5,587,458 | A | 12/1996 | King et al. |
| 5,591,669 | A | 1/1997 | Krimpenfort et al. |
| 5,641,870 | A | 6/1997 | Rinderknecht et al. |
| 5,736,137 | A | 4/1998 | Anderson et al. |
| 5,776,456 | A | 7/1998 | Anderson et al. |
| 5,821,337 | A | 10/1998 | Carter et al. |
| 5,869,046 | A | 2/1999 | Presta et al. |
| 6,517,529 | B1 | 2/2003 | Quinn |
| 7,151,164 | B2 | 12/2006 | Hansen et al. |
| 9,045,543 | B2 * | 6/2015 | Liu .................. A61P 21/04 |
| 2013/0089540 | A1 | 4/2013 | Liu et al. |

FOREIGN PATENT DOCUMENTS

| | | |
|---|---|---|
| EP | 0216846 B1 | 1/1990 |
| EP | 0256055 B1 | 8/1991 |
| EP | 0323997 B1 | 4/1993 |
| EP | 0338841 B1 | 3/1995 |
| EP | 0340109 B1 | 5/1997 |
| RU | 2358762 C2 | 6/2009 |
| RU | 2457860 C2 | 8/2012 |
| RU | 2489166 C2 | 8/2013 |
| WO | 90/08187 A1 | 7/1990 |
| WO | 90/11294 A1 | 10/1990 |
| WO | 91/01133 A1 | 2/1991 |
| WO | 93/16185 A2 | 8/1993 |
| WO | 97/17852 A1 | 5/1997 |
| WO | 2003/068821 A2 | 8/2003 |
| WO | 2004/056312 A2 | 7/2004 |
| WO | 2006/084264 A2 | 8/2006 |
| WO | 2011/100398 A1 | 8/2011 |
| WO | 2013/007052 A1 | 1/2013 |
| WO | 2014/072741 A1 | 5/2014 |

OTHER PUBLICATIONS

Related International Application No. PCT/RU2019/050205 Written Opinion dated Mar. 12, 2020.
Cheson Bruce D. Monoclonal antibody therapy of chronic lymphocytic leukemia. Cancer Immunol Immunother. Feb. 2006; 55 (2): 188-96, doi: 10.1007/s00262-005-0010-0.
Rabat Elvin A et al. Sequences of proteins of immunological interest. Bethesda. 5th ed. Md: U.S. Dept, of Health and Human Services, Public Health Service, National Institutes of Health, 1991, vol. 1, NIH Publication No. 91-3242, p. 339, 379.
Alekseev S.M. et al. Sovremennyi podkhod k razrabotke i issledovaniiu bioanalogov na primere pervogo rossiiskogo preparata monoklonalnykh antitel—Atsellbiia® (Rituksimab) Современный подход к разработке и исследованию биоаналогов на примере первого российского препарата моноклональных антител Ацеллбия ® (ритуксимаб) Issledovaniia i praktika v meditsine. 2015, t. 2, JN ° 1, p. 8-12, doi:10.17709/2409-2231-2015-2-1-8-12.
Ulrich Storz, How approval history is reflected by a corresponding patent filing strategy, Rituximab, mAbs, pp. 820-837, Received Mar. 2, 2014, Accepted May 3, 2014, Published online: May 19, 2014, https://www.tandfonline.com/doi/full/10.4161/mabs.29105.
Corresponding European application No. 19880700.0 extended European search report dated Apr. 2, 2024.
Corresponding European application No. 19880700.0 extended European search report dated Jul. 1, 2022.
Corresponding Chinese application No. 201980087511.2 examination report dated Dec. 19, 2023. (English translation provided).
Wirt Tim et al., "An Fc Double-Engineered CD20 Antibody with Enhanced Ability to Trigger Complement-Dependent Cytotoxicity and Antibody-Dependent Cell-Mediated Cytotoxicity", Transfusion Medicine Hemotherapy, vol. 44, No. 5, Sep. 11, 2017 (Sep. 11, 2017), pp. 292-300.
Sean H. Lim et al., "Anti-CD20 monoclonal antibodies: historical and future perspectives", Haematologica. Jan. 2010; 95(1): 135-143. Published online Sep. 22, 2009. doi: 10.3324/haematol.2008.001628.
Kabat, Elvin A., "[Passage]", Sequences of proteins of immunological interest (5th ed.), U.S. Dept. of Health and Human Services, Public Health Service, National Institutes of Health, Bethesda, MD, (Nov. 30, 1990), vol. 1,Nov. 30, 1990, pp. 339-379.
Anderson et al., Expression of human B cell-associated antigens on leukemias and lymphomas: a model of human B cell differentiation. Blood. vol. 63, Issue 6, Jun. 1, 1984. p. 1424-1433.
Bird et al. Single-chain antigen-binding proteins. Science. Vol 242, Issue 4877. Oct. 21, 1988. pp. 423-426.
Burks et al., In vitro scanning saturation mutagenesis of an antibody binding pocket. Proc Natl Acad Sci USA, 94:412-417 (1997).
Carter et al., High Level *Escherichia coli* Expression and Production of a Bivalent Humanized Antibody Fragment. Bio/Technology 10:163-167 (1992).
Chen, Y., et al., Selection and analysis of an optimized anti-VEGF antibody: crystal structure of an affinity-matured fab in complex with antigen. J. Mol. Biol. 293: 865-881(1999).
Clynes et al. Fc receptors are required in passive and active immunity to melanoma. PNAS (USA) 95: 652-656 (1998).
De Haard HJ et al., A large non-immunized human Fab fragment phage library that permits rapid isolation and kinetic analysis of high affinity antibodies. J Biol Chem 1999,274:18218-18230.
Edelman, G.M., et al., The Covalent Structure of an Entire yG Immunoglobulin Molecule. Proc. Natl. Acad. Sci. Natl. Acad. Sci. USA 63 (1969) 78-85.
Einfeld et al., Molecular cloning of the human B cell CD20 receptor predicts a hydrophobic protein with multiple transmembrane domains. EMBO J. 7(3), 1988, p. 711-717.
Gazzano-Santoro et al., A non-radioactive complement-dependent cytotoxicity assay for anti-CD20 monoclonal antibody. J. Immunol. Methods 202: 163 (1996).
J. A. Singh et al., 2015 American College of Rheumatology Guideline for the Treatment of Rheumatoid Arthritis. Arthritis Care Res (Hoboken) 68, 1-25 (2016).
Lefranc et al., IMGT unique numbering for immunoglobulin and T cell receptor variable domains and Ig superfamily V-like domains. Dev. Comp Immunol. 27:55-77 (2003).
Magdelaine-Beuzelin et al., Structure-function relationships of the variable domains of monoclonal antibodies approved for cancer treatment. Crit Rev.Oncol Hematol. 64:210 225 (2007).
Miller R.A et al., Monoclonal antibody therapeutic trials in seven patients with T-cell lymphoma, Blood, 62, 1983, p. 988-995.
Reff et al., Depletion of B cells in vivo by a chimeric mouse human monoclonal antibody to CD20. Blood 83(2), 1994, p. 435-445.
Schroff R.W. et al., Human anti-murine immunoglobulin response in patients receiving monoclonal antibody therapy, Cancer Res., 45, 1985, p. 879-885.
Sheets MD et al. Efficient construction of a large nonimmune phage antibody library: the production of high-affinity human single-chain antibodies to protein antigens. Proc Natl Acad Sci U S A 1998,95:6157-6162.
Huston et al. Protein engineering of antibody binding sites: recovery of specific activity in an anti-digoxin single-chain Fv analogue produced in Escherichia coli. Proc. Natl. Acad. Sci. USA 85:5879-5883 (1988).
Ulitin AB et al. The library of human miniantibodies in the phage display format: Designing and testing DAN: Izd-vo "Nauka"; 2005.
Valentine et al., Phosphorylation of the CD20 Phosphoprotein in Resting B Lymphocytes: Regulation by protein kinase C. Journal of Biological Chemistry. Volume 264, Issue 19, Jul. 5, 1989, pp. 11282-11287.
Wu et al., Stepwise in vitro affinity maturation of Vitaxin, an avB3-specific humanized mAb. PNAS May 26, 1998 95 (11) 6037-6042.
Has et al. A Large Non-immunized Human Fab Fragment Phage Library That Permits Rapid Isolation and Kinetic Analysis of High Affinity Antibodies. J Biol Chem. Jun. 25, 1999; 274(26): 18218-18230.
Janas E et all., Functional role of lipid rafts in CD20 activity?, Biochem Soc Symp. 2005;(72):165-175 Jones et al., Nature (London), 321, 1986, p. 522-525.
Kohler, et al. Continuous cultures of fused cells secreting antibody of predefined specificity. Nature 256, 1975.

(56) References Cited

OTHER PUBLICATIONS

Marks et al., By-Passing Immunization: Building High Affinity Human Antibodies by Chain Shuffling. Bio/Technology, 10:779-783 (1992).
Sachdev S. Sidhu et al., [21] Phage display for selection of novel binding peptides. Methods in Enzymology. vol. 328, 2000, pp. 333-363, IN5.
Munson et al., Ligand: A versatile computerized approach for characterization of ligand-binding systems. Analytical Biochemistry. vol. 107, Issue 1, Sep. 1, 1980, pp. 220-239 (1980).
Tristan J. Vaughan et al., Human antibodies with sub-nanomolar affinities isolated from a large non-immunized phage display library. Nature Biotechnology vol. 14, pp. 309-314 (1996).
Neuberger et al., A hapten-specific chimaeric IgE antibody with human physiological effector function. Nature (London), 314, 1985, p. 268-270.
Offner et al., T cell receptor peptide therapy triggers autoregulation of experimental encephalomyelitis. Science 251:430-432 (1991).
Smith GP. Filamentous fusion phage: novel expression vectors that display cloned antigens on the virion surface. Science 1985, 228:1315-1317.
Ward et al., Binding activities of a repertoire of single immunoglobulin variable domains secreted from *Escherichia coli*. (1989) Nature 341:544-546.
Woof J., Burton D., Human antibody-Fc receptor interactions illuminated by crystal structures. Nature Reviews Immunology vol. 4, pp. 89-99 (2004).
Vaughan TJ et al. Human antibodies with sub-nanomolar affinities isolated from a large non-immunized phage display library. Nat Biotechnol 1996, 14:309-314.
Clackson et al., Making antibody fragments using phage display libraries. Nature, 352:624-628 (1991).
Waterhouse et al., Combinatorial infection and in vivo recombination: a strategy for making large phage antibody repertoires. Nucl. Acids. Res. 21:2265-2266 (1993).
Morrison, et al., Chimeric human antibody molecules: mouse antigen-binding domains with human constant region domains. Proc. Natl. Acad. Sci. USA: 81:6851 (1984).
Ravetch and Kinet, Fc Receptors. Annual Review of Immunology. vol. 9:457-492 (vol. publication date Apr. 1991).
Daeron, Fc Receptor Biology. Annu. Rev. Immunol. 15: 203-234 (1997).
McCafferty et al., Phage antibodies: filamentous phage displaying antibody variable domains. Nature, 348:552-553 (1990).
Marks JD et al., Bypassing immunization. Human antibodies from V-gene libraries displayed on phage. J Mol Biol 1991,222:581-597.
Riechman et al., Reshaping human antibodies for therapy. Nature (London), 332, 1988, p. 323-327.
Kozbor, A human hybrid myeloma for production of human monoclonal antibodies. J Immunol Dec. 1, 1984, 133 (6) p. 3001-3005 (Abstract).
Tedder et al., The B cell surface molecule B1 is functionally linked with B cell activation and differentiation. J. Immunol. 135(2), 1985, p. 973-979 (Abstract).
Corresponding European application No. 2019313199 extended European search report dated Jul. 1, 2022.
Lim et al., Anti-CD20 monoclonal antibodies: historical and future perspectives. Haematologica, Fondazione Ferrata Storti It; Biosciences Information Service, Philadelphia, PA, US, vol. 95, No. 1, Jan. 1, 2010, pp. 135-143.
Ai-Lan et al., Monoclonal antibodies in the treatment of multiple sclerosis: emergence of B-cell-targeted therapies: Monoclonal antibodies in Ms. Britsh Journal of Pharmacology. vol. 171, No. 13, Jul. 1, 2017, pp. 1895-1907.
Corresponding Japanese application No. 2021-523796 examination report dated Nov. 8, 2023. (English translation provided).

\* cited by examiner

MONOCLONAL ANTIBODY THAT SPECIFICALLY BINDS TO CD20

REFERENCE TO A SEQUENCE LISTING SUBMITTED VIA EFS-WEB

The content of the ASCII text file of the sequence listing named "P2253US00-BCD-132_PCTRU2019050205_SL_corrected_v2" which is 15.3 kb in size was created on Nov. 26, 2021 and electronically submitted herewith via EFS-Web is incorporated herein by reference.

FIELD OF INVENTION

The present invention relates to the field of biotechnology, in particular to anti-CD20 antibodies or antigen-binding fragments thereof, and to use thereof for treatment of diseases associated with B cells. More specifically, the present invention relates to monoclonal antibodies that specifically bind to CD20 (B-lymphocyte antigen CD20). The invention also relates to a nucleic acid encoding said antibody or antigen-binding fragment thereof, an expression vector, a method for producing an antibody, and the use of antibody for treatment of diseases or disorders associated with B cells, in particular with B-lymphocyte antigen CD20.

BACKGROUND OF THE INVENTION

Lymphocytes are one of many types of white blood cells; they specifically recognize and respond to a foreign antigen. The three main types of lymphocytes are B-lymphocytes (B cells), T-lymphocytes (T-cells) and natural killer (NK) cells. B-lymphocytes are cells responsible for production of antibodies and for humoral immunity. B cells mature within the bone marrow and leave the marrow expressing an antigen-binding antibody on the cell surface. When a previously unexposed B cell first encounters an antigen for which the membrane-bound antibody is specific, the cell begins dividing rapidly and its progeny differentiate into memory B cells and effector cells called "plasma cells". Memory B cells have a longer life span and continue to express membrane-bound antibody with the same specificity as the original parent cell. Plasma cells do not produce a membrane-bound antibody, but instead they produce an antibody in a form that can be secreted. Secreted antibodies are the major effector molecules of humoral immunity.

Antigen CD20 (also called human B-lymphocyte-restricted differentiation antigen, Bp35) is a hydrophobic transmembrane protein with a molecular weight of approximately 35 kDa located on pre-B and mature B lymphocytes (Valentine et al., J. Biol. Chem. 264(19), 1989, p. 11282-11287; and Einfeld et al, EMBO J. 7(3), 1988, p. 711-717). Antigen is also expressed on the surface of more than 90% of B cells in non-Hodgkin's lymphomas (HXJI) (Anderson et al, Blood 63(6), 1984, p. 1424-1433), but has not been detected on hematopoietic stem cells, pro-B cells, normal plasma cells or other normal tissues (Tedder et al, J. Immunol. 135(2), 1985, p. 973-979). CD20 seems to regulate an early step(s) in the activation process for cell cycle initiation and differentiation (Tedder et al., supra) and possibly functions as a calcium ion channel (Tedder et al., J. Cell. Biochem. 14D, 1990, p. 195).

Given the expression of CD20 in B cell lymphomas, this antigen can be a valuable therapeutic target in the treatment of said lymphomas.

Antibody Rituximab (RITUXAN, MabThera, Acellbia), which is a genetically engineered chimeric murine/human monoclonal antibody against human antigen CD20, is indicated for the treatment of patients suffering from relapsed or refractory low-grade or follicular CD20-positive B cell non-Hodgkin lymphoma. Rituximab is an antibody called "C2B8" in U.S. Pat. Nos. 5,736,137 and 5,776,456. The study of in vitro mode of action has shown that Rituximab binds human complement and lyse B-lymphoid cell lines through complement dependent cytotoxicity (CDC) (Reff et al, Blood 83(2), 1994, p. 435-445). Furthermore, this antibody has significant activity in antibody-dependent cellular cytotoxicity (ADCC) assay. Preclinical trials in vivo have shown that rituximab depletes B cells from the peripheral blood, lymph nodes and bone marrow of cynomolgus monkeys (*Macaca fascicularis*) presumably through complement- and cell-mediated processes (Reff et al, Blood 83(2), 1994, p. 435-445).

Furthermore, later it was found that anti-CD20 antibodies, such as rituximab, were also an effective therapeutic agent in the treatment of various autoimmune diseases, such as rheumatoid arthritis (patents RU2358762, RU2489166 and RU2457860) or Wegener's granulomatosis (patent RU2326127).

A major limitation in the use of murine antibodies in human therapy is the formation of human anti-mouse antibodies (HAMA) (see, for example, Miller R. A. et al «Monoclonal antibody therapeutic trials in seven patients with T-cell lymphoma», Blood, 62, 1983, p. 988-995; and Schroff R. W. et al «Human anti-murine immunoglobulin response in patients receiving monoclonal antibody therapy», Cancer Res., 45, 1985, p. 879-885). Even chimeric molecules, where the variable (V) domains of rodent antibodies are fused to human constant (C) regions, are still capable of eliciting a significant immune response (HACA, human anti-chimeric antibody response) (Neuberger et al, Nature (London), 314, 1985, p. 268-270).

A powerful approach to overcome these limitations in the clinical use of monoclonal antibodies is "humanization" of the murine antibody or antibody from a non-human species (Jones et al, Nature (London), 321, 1986, p. 522-525; Riechman et al, Nature (London), 332, 1988, p. 323-327).

Thus, it is beneficial to produce therapeutic antibodies against CD20 antigen that create minimal or no antigenicity when administered to patients and are primarily intended for use in chronic treatment. The present invention solves this problem.

The monoclonal antibody BCD-132 selectively and specifically binds to CD20 antigen and is an effective inhibitor of CD20 antigen; also, an antibody of the invention has minimal antigenicity when administered to patients.

BRIEF SUMMARY OF INVENTION

In one aspect, the present invention relates to a monoclonal antibody or antigen-binding fragment thereof that specifically binds to CD20 and comprises:
1) a heavy chain variable domain comprising an amino acid sequence shown in SEQ ID NO: 2 or SEQ ID NO: 6;
2) a light chain variable domain comprising an amino acid sequence shown in SEQ ID NO: 4 or SEQ ID NO: 8.

In some embodiments, a monoclonal antibody or antigen-binding fragment thereof comprise:
1) a heavy chain variable domain comprising an amino acid sequence shown in SEQ ID NO: 2;

2) a light chain variable domain comprising an amino acid sequence shown in SEQ ID NO: 4.

In some embodiments, a monoclonal antibody or antigen-binding fragment thereof comprise:
1) a heavy chain variable domain comprising an amino acid sequence shown in SEQ ID NO: 6;
2) a light chain variable domain comprising an amino acid sequence shown in SEQ ID NO: 8.

In some embodiments, a monoclonal antibody comprises:
1) a heavy chain comprising an amino acid sequence shown in SEQ ID NO: 1 or SEQ ID NO: 5;
2) a light chain comprising an amino acid sequence shown in SEQ ID NO: 3 or SEQ ID NO: 7.

In some embodiments, a monoclonal antibody comprises:
1) a heavy chain comprising an amino acid sequence shown in SEQ ID NO: 1;
2) a light chain comprising an amino acid sequence shown in SEQ ID NO: 3.

In some embodiments, a monoclonal antibody comprises:
1) a heavy chain comprising an amino acid sequence shown in SEQ ID NO: 5;
2) a light chain comprising an amino acid sequence shown in SEQ ID NO: 7.

In some embodiments, a monoclonal antibody that specifically binds to CD20 is a full-length IgG antibody.

In some embodiments, a monoclonal antibody is of human IgG1, IgG2, IgG3, IgG4 isotype.

In some embodiments, a monoclonal antibody is of human IgG1 isotype.

In one aspect, the present invention relates to a nucleic acid that encodes the above antibody.

In some embodiments, a nucleic acid is DNA.

In one aspect, the present invention relates to an expression vector comprising the above nucleic acid.

In one aspect, the present invention relates to a method for production of a host cell for production of the above antibody that comprises transformation of a cell with the above vector.

In one aspect, the present invention relates to a host cell for production of the above antibody, said host cell comprising the above nucleic acid.

In one aspect, the present invention relates to a method for production of the above antibody that comprises culturing of the above host cell in a culture medium under conditions sufficient to produce said antibody, if necessary, followed by isolation and purification of the obtained antibody.

In one aspect, the present invention relates to a pharmaceutical composition used for treatment of a disease or disorder mediated by CD20 comprising said antibody or antigen-binding fragment thereof in a therapeutically effective amount in combination with one or more pharmaceutically acceptable excipients.

In some embodiments, a pharmaceutical composition is intended to be used for treatment of a disease or disorder, where the disease or disorder is selected from:
a) an oncological disease or disorder or
b) an autoimmune disease or disorder.

In some embodiments, a pharmaceutical composition is intended to be used for treatment of an oncological disease or disorder that is selected from the group comprising: B cell lymphoma or leukemia.

In some embodiments, a pharmaceutical composition is intended for the treatment of B cell lymphoma selected from: non-Hodgkin lymphoma (NHL) or Hodgkin's disease (Hodgkin's lymphoma).

In some embodiments, a pharmaceutical composition is intended for the treatment of leukemia selected from: chronic lymphocytic leukemia (CLL) or small lymphocytic lymphoma (SLL).

In some embodiments, a pharmaceutical composition is intended for the treatment of an autoimmune disease or disorder selected from the group comprising: rheumatoid arthritis, juvenile rheumatoid arthritis (Still's disease), systemic lupus erythematosus (SLE), lupus nephritis, ulcerative colitis, Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, ANCA vasculitis, rejection of graft of parenchymatous organs, graft-versus-host disease (GvHD), diabetes mellitus, Raynaud's syndrome, Sjorgen's syndrome and glomerulonephritis.

In one aspect, the present invention relates to a pharmaceutical combination for prevention or treatment of a disease or disorder mediated by CD20 that comprises said antibody or antigen-binding fragment thereof and at least one therapeutically active compound.

In some embodiments, a pharmaceutical combination comprises a different therapeutically active antitumour compound selected from a chemotherapeutic agent, antibody or anti-hormonal agent.

In one aspect, the present invention relates to a method for inhibition of biological activity of CD20 in a subject in need of such inhibition that comprises administration of an effective amount of said antibody or antigen-binding fragment thereof.

In one aspect, the present invention relates to a method for treatment of a disease or disorder mediated by CD20 that comprises administration to a subject in need of such treatment of said antibody or antigen-binding fragment thereof or said pharmaceutical composition, in a therapeutically effective amount.

In some embodiments, a method for treatment of a disease or disorder relates to a disease or disorder selected from:
a) an oncological disease or disorder or
b) an autoimmune disease or disorder.

In some embodiments, a method for treatment of a disease or disorder relates to an oncological disease or disorder selected the group comprising: B cell lymphoma or leukemia.

In some embodiments, a method for treatment of a disease or disorder relates to B cell lymphoma selected from: non-Hodgkin lymphoma (NHL) or Hodgkin's disease (Hodgkin's lymphoma).

In some embodiments, a method for treatment of a disease or disorder relates to leukemia selected from: chronic lymphocytic leukemia (CLL) or small lymphocytic lymphoma (SLL).

In some embodiments, a method for treatment of a disease or disorder relates to an autoimmune disease or disorder selected from the group comprising: rheumatoid arthritis, juvenile rheumatoid arthritis (Still's disease), systemic lupus erythematosus (SLE), lupus nephritis, ulcerative colitis, Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, ANCA vasculitis, rejection of graft of parenchymatous organs, graft-versus-host disease (GvHD), diabetes mellitus, Raynaud's syndrome, Sjorgen's syndrome and glomerulonephritis.

In one aspect, the present invention relates to the use of said antibody or antigen-binding fragment thereof or said pharmaceutical composition for treatment in a subject in need of such treatment of a disease or disorder mediated by CD20.

In some embodiments, said antibody or antigen-binding fragment thereof is used for treatment of a disease or disorder, where the disease or disorder is selected from:
a) an oncological disease or disorder or
b) an autoimmune disease or disorder.

In some embodiments, said antibody or antigen-binding fragment thereof is used for treatment of an oncological disease or disorder that is selected from the group comprising: B cell lymphoma or leukemia.

In some embodiments, said antibody or antigen-binding fragment thereof is used for treatment of B cell lymphoma selected from: non-Hodgkin lymphoma (NHL) or Hodgkin's disease (Hodgkin's lymphoma).

In some embodiments, said antibody or antigen-binding fragment thereof is used for treatment of leukemia selected from: chronic lymphocytic leukemia (CLL) or small lymphocytic lymphoma (SLL).

In some embodiments, said antibody or antigen-binding fragment thereof is used for treatment of an autoimmune disease or disorder selected from the group comprising: rheumatoid arthritis, juvenile rheumatoid arthritis (Still's disease), systemic lupus erythematosus (SLE), lupus nephritis, ulcerative colitis, Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, ANCA vasculitis, rejection of graft of parenchymatous organs, graft-versus-host disease (GvHD), diabetes mellitus, Raynaud's syndrome, Sjorgen's syndrome and glomerulonephritis.

| BCD-132-L-028 |
|---|
| ● MabThera ■ BCD-132-L-028 ▼ BCD-132-L-077. |

Figure 27:
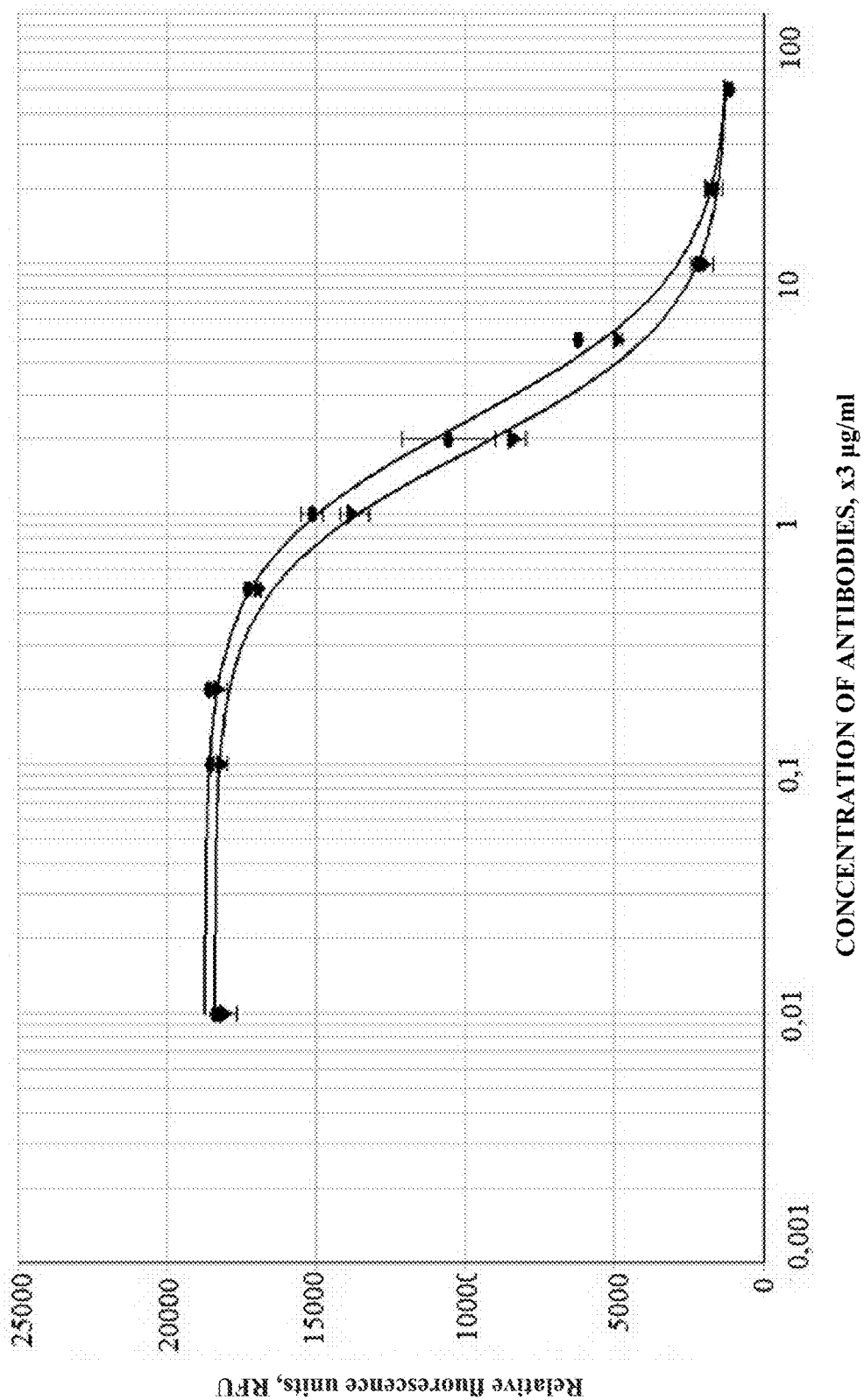

FIG. 27. Measurement of complement dependent cytotoxicity of BCD-132-L-028 and BCD-132-L-077 as compared to MabThera.

| BCD-132-L-077 |
|---|
| ● MabThera ■ BCD-132-L-028 ▼ BCD-132-L-077. |

Figure 28:
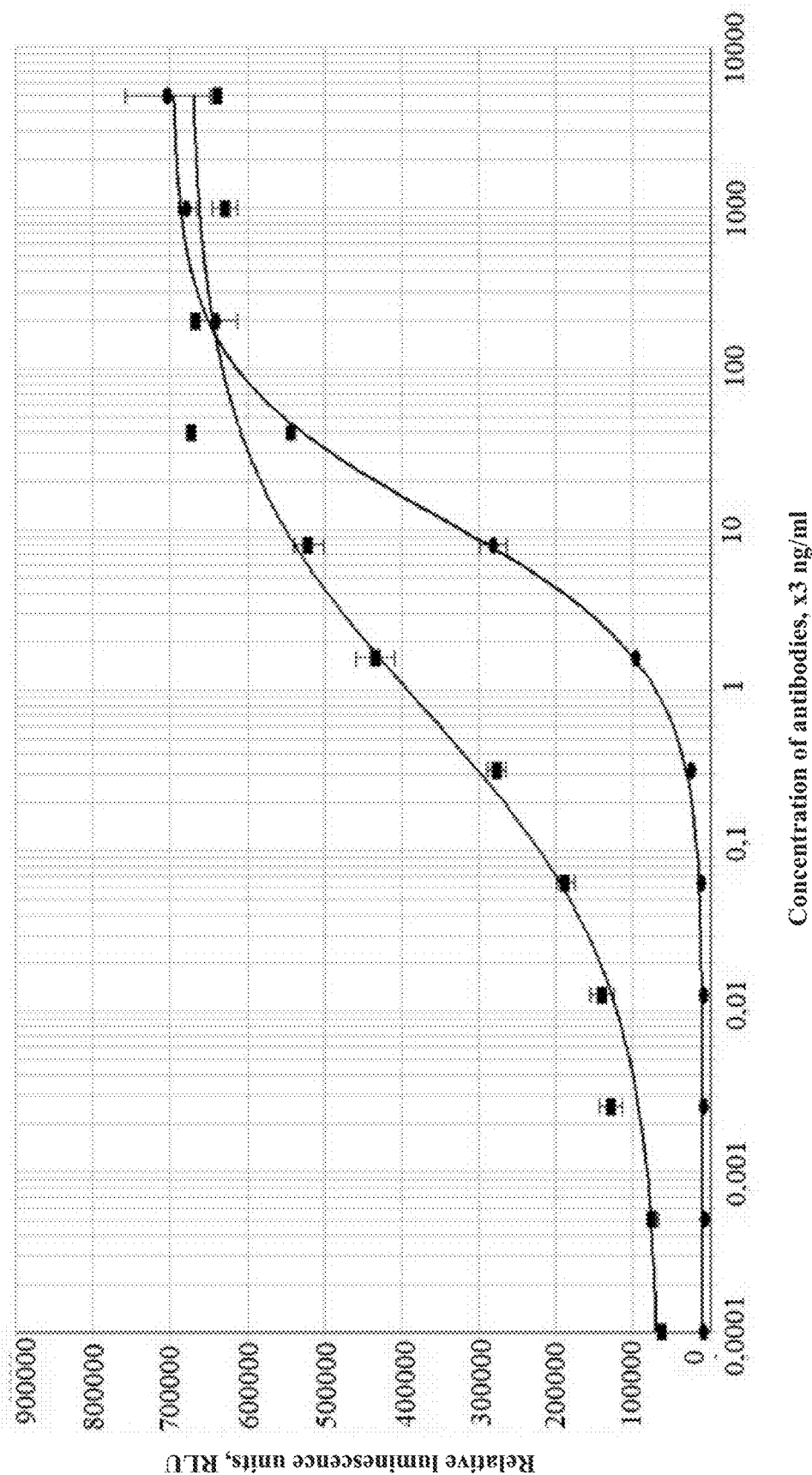

FIG. 28. Measurement of antibody dependent cellular cytotoxicity of BCD-132-L-028 and BCD-132-L-077 as compared to MabThera. Low affinity CD16 reporter cell line, target WIL2-S cell line.

| BCD-132-L-028 |
|---|
| ● MabThera ■ BCD-132-L-028 ▼ BCD-132-L-077. |

Figure 29:
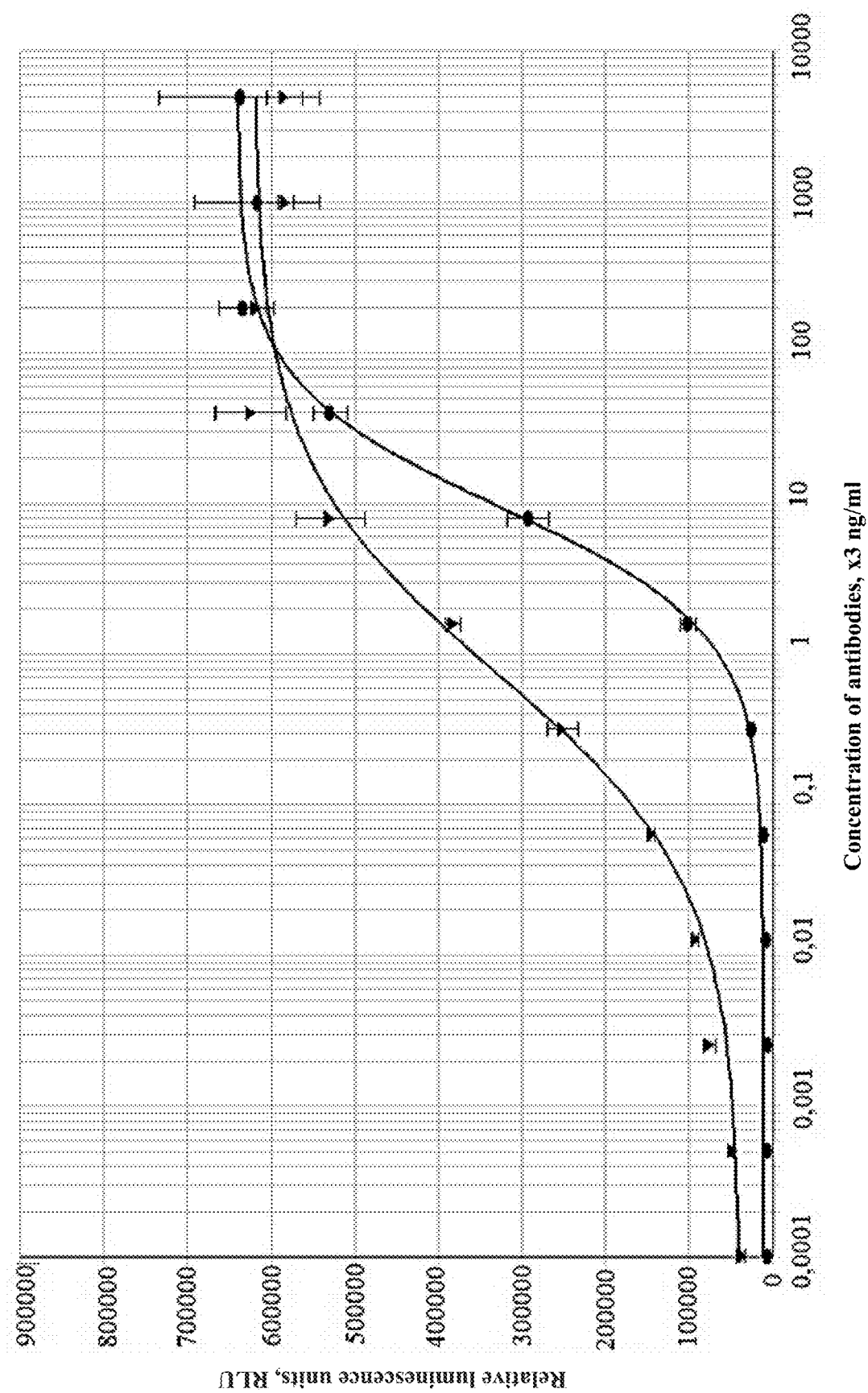

FIG. 29. Measurement of antibody dependent cellular cytotoxicity of BCD-132-L-028 and BCD-132-L-077 as compared to MabThera. Low affinity CD16 reporter cell line, target WIL2-S cell line.

| BCD-132-L-077 |
|---|
| ● MabThera ■ BCD-132-L-028 ▼ BCD-132-L-077. |

Figure 30:
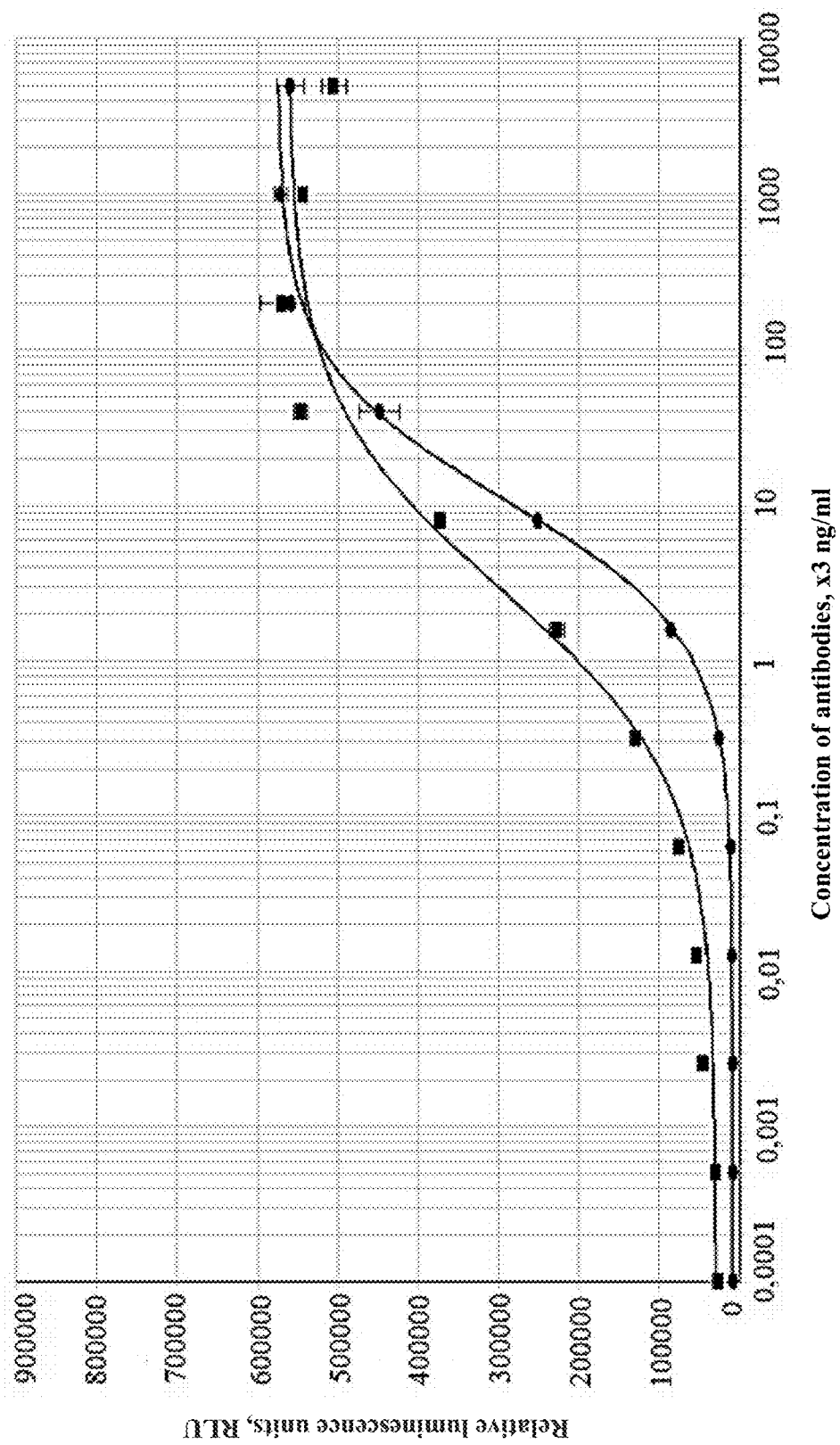

FIG. 30. Measurement of antibody dependent cellular cytotoxicity of BCD-132-L-028 and BCD-132-L-077 as compared to MabThera. Low affinity CD16 reporter cell line, target WIL2-S cell line.

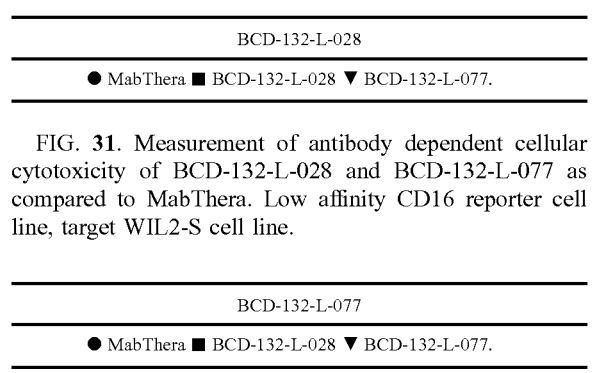

Figure 31:
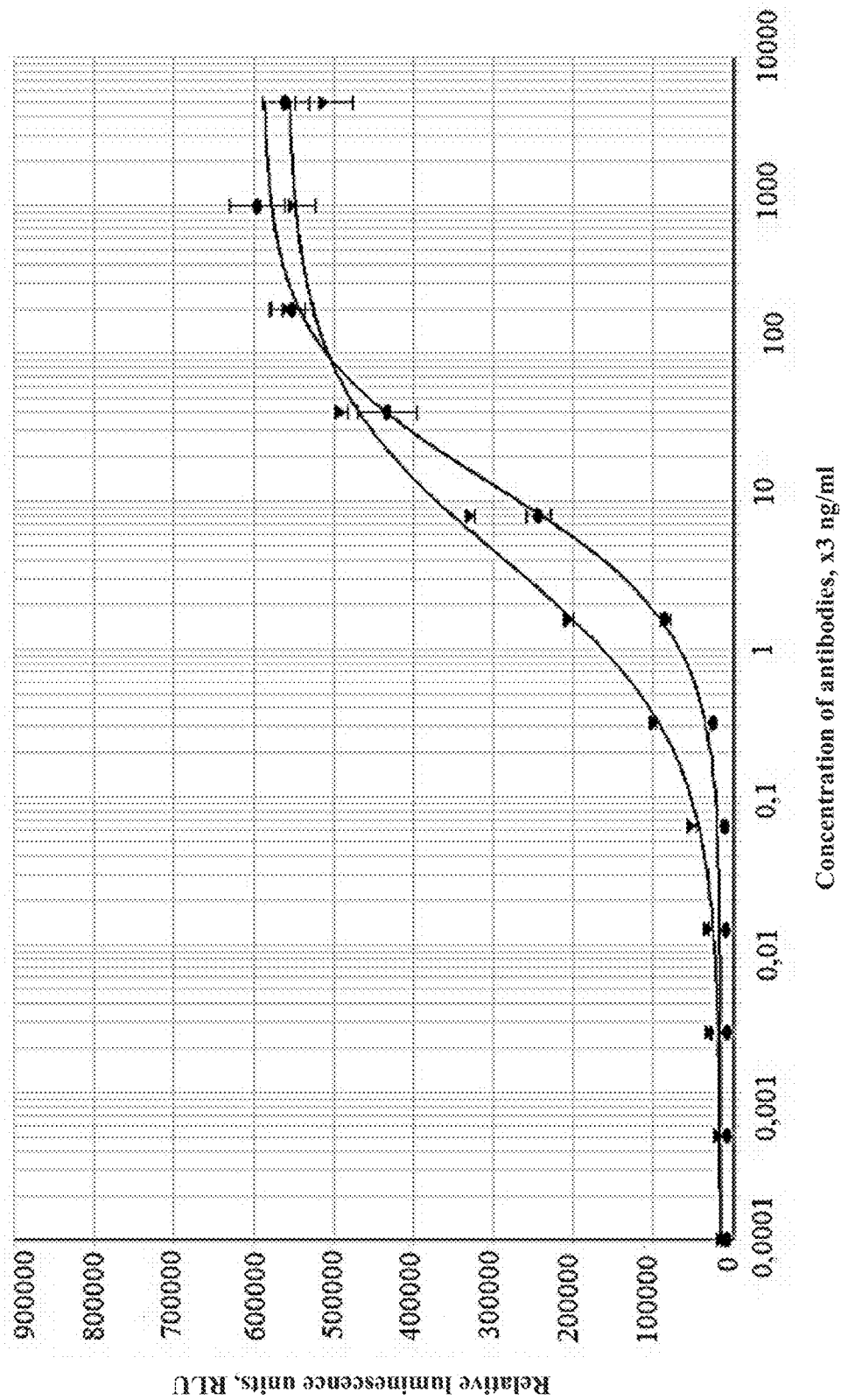

FIG. 31. Measurement of antibody dependent cellular cytotoxicity of BCD-132-L-028 and BCD-132-L-077 as compared to MabThera. Low affinity CD16 reporter cell line, target WIL2-S cell line.

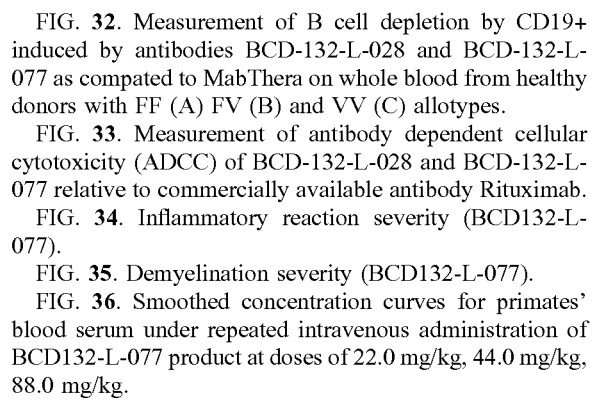

Figure 32:
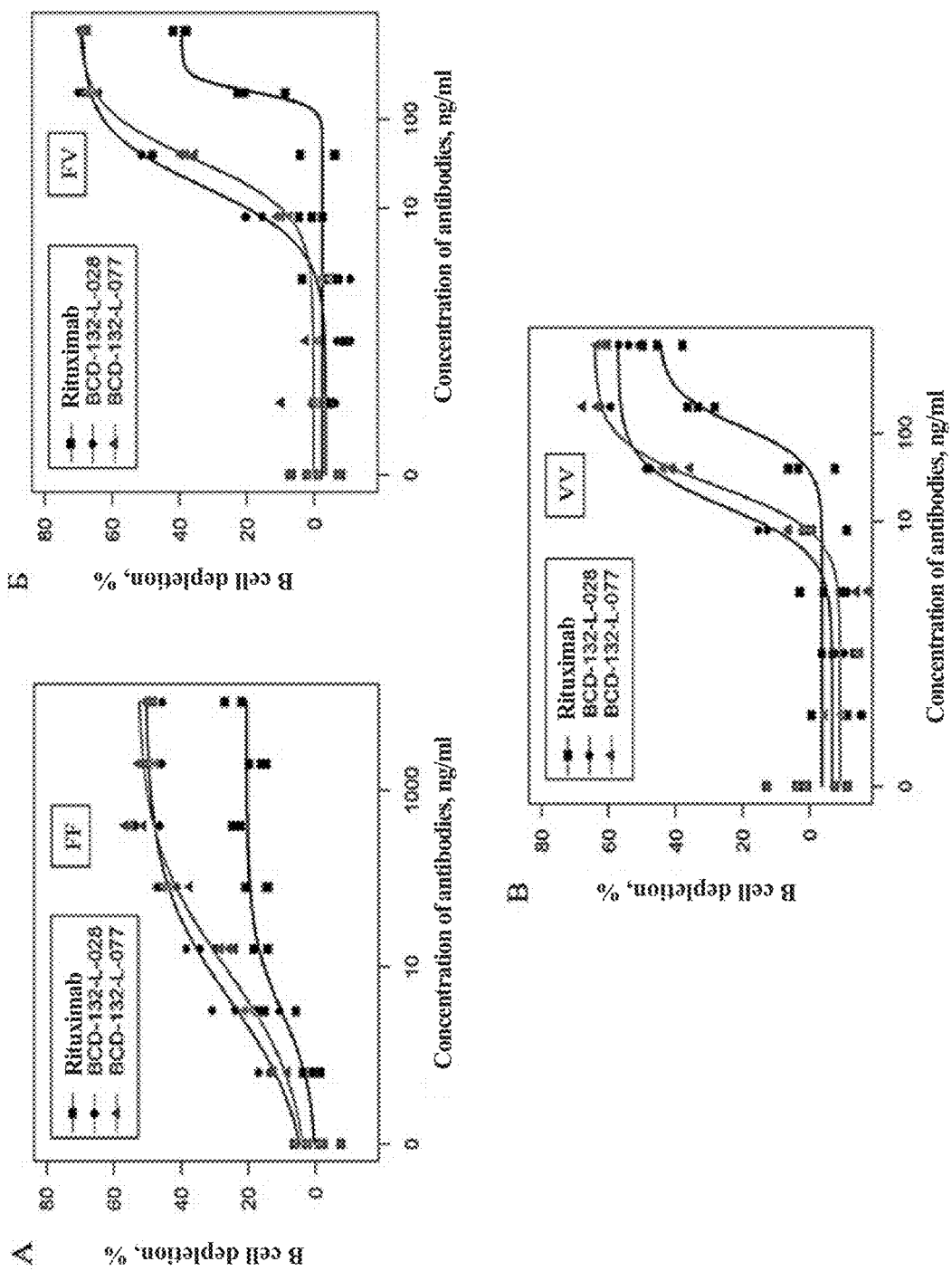

FIG. 32. Measurement of B cell depletion by CD19+ induced by antibodies BCD-132-L-028 and BCD-132-L-077 as compated to MabThera on whole blood from healthy donors with FF (A) FV (B) and VV (C) allotypes.

Figure 33:
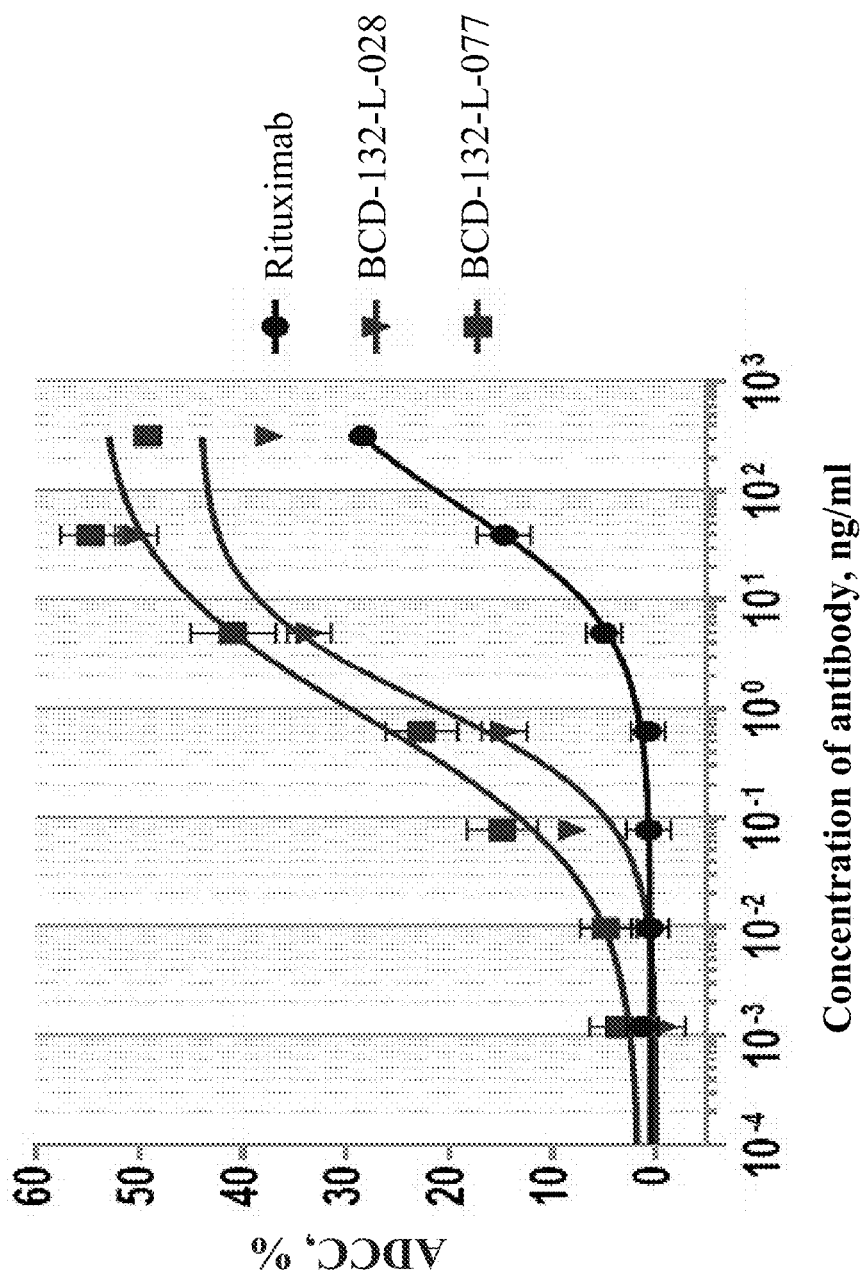

FIG. 33. Measurement of antibody dependent cellular cytotoxicity (ADCC) of BCD-132-L-028 and BCD-132-L-077 relative to commercially available antibody Rituximab.

Figure 34:
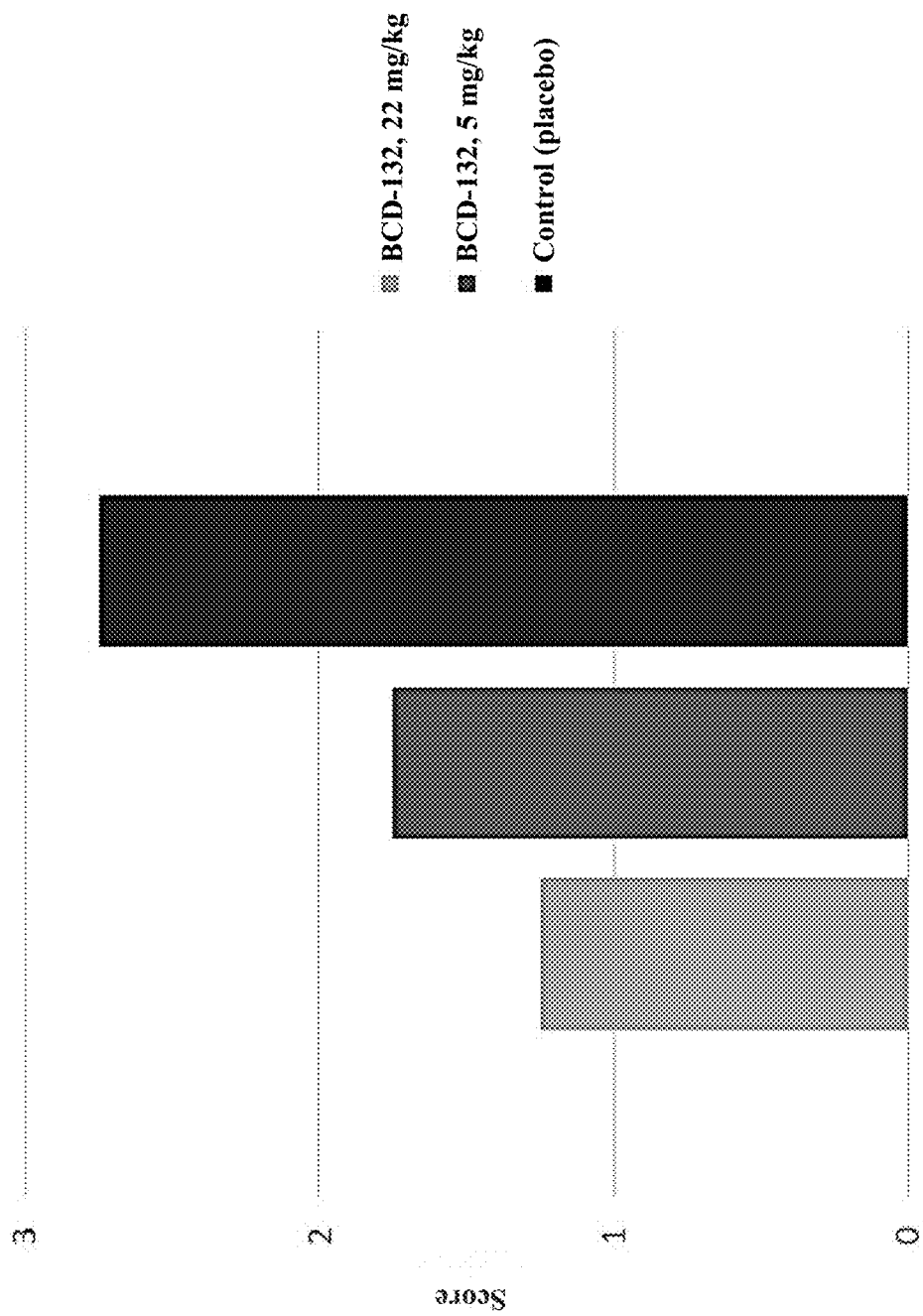

FIG. 34. Inflammatory reaction severity (BCD132-L-077).

Figure 35:
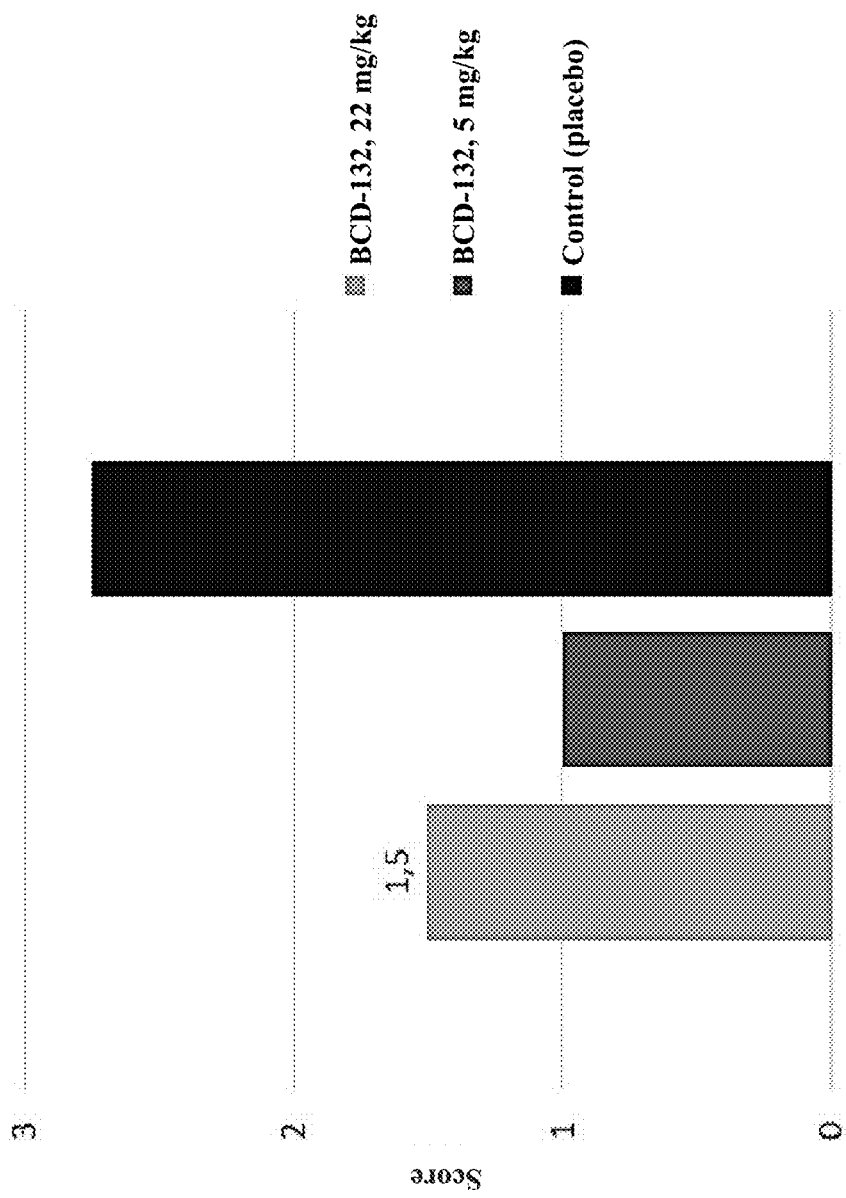

FIG. 35. Demyelination severity (BCD132-L-077).

Figure 36:
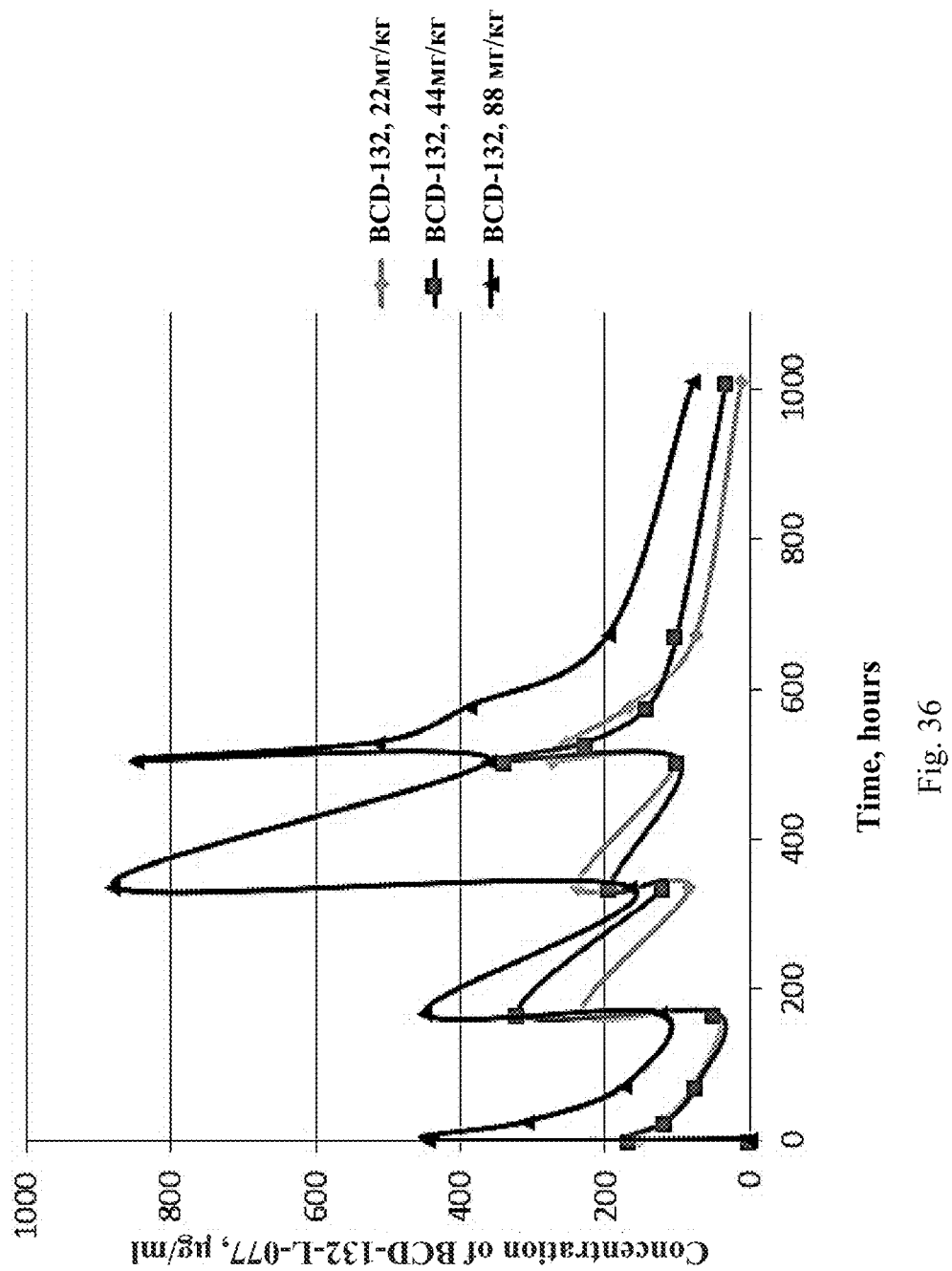

FIG. 36. Smoothed concentration curves for primates' blood serum under repeated intravenous administration of BCD132-L-077 product at doses of 22.0 mg/kg, 44.0 mg/kg, 88.0 mg/kg.

DESCRIPTION OF THE INVENTION

Definitions and General Methods

Unless defined otherwise, all technical and scientific terms used herein have the same meaning as is commonly understood by one of ordinary skill in the art.

Further, unless otherwise required by context, singular terms shall include pluralities and plural terms shall include the singular. Typically, the classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known and widely used by those skilled in the art. Enzyme reactions and purification methods are performed according to the manufacturer's instructions, as is common in the art, or as described herein.

Definitions Related to Antibody

CD20, or B-lymphocyte antigen CD20 is a protein, co-receptor found on the surface of B-lymphocytes. CD20 is a product of human MS4A1 gene. The exact function of this protein is still unknown, it is however contemplated that the protein plays a role in the activation and proliferation of B-lymphocytes.

MS4A1 gene is a member of the MS4A (membrane-spanning 4A) gene family that consists of at least 25 other genes. The genes of this family are clustered at human chromosome locus 11q12-13. The corresponding proteins are contemplated to have similar spatial structure: they have a tetraspanning membrane topology with an N- and C-terminal cytoplasmic domains (JANAS E. ET ALL., Functional role of lipid rafts in CD20 activity?, Biochem Soc Symp. 2005; (72):165-75).

Amplification of this gene and/or overexpression of protein thereof have been observed in many cancers or autoimmune diseases, including in:
a) oncological diseases or disorders from the group comprising: non-Hodgkin lymphoma (NHL), Hodgkin's disease (Hodgkin's lymphoma), chronic lymphocytic leukemia (CLL) or small lymphocytic lymphoma (SLL).
b) autoimmune diseases or disorders from the group comprising: rheumatoid arthritis, juvenile rheumatoid arthritis (Still's disease), systemic lupus erythematosus (SLE), lupus nephritis, ulcerative colitis, Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, ANCA vasculitis, rejection of graft of parenchymatous organs, graft-versus-host disease (GvHD), diabetes mellitus, Raynaud's syndrome, Sjorgen's syndrome and glomerulonephritis.

The term "binding molecule" includes antibodies and immunoglobulins.

The term "antibody" or "immunoglobulin" (Ig) as used herein includes whole antibodies and any antigen binding fragment (i.e., "antigen-binding portion") or single chains. The term "antibody" refers to a glycoprotein comprising at least two heavy (H) chains and two light (L) chains interconnected by disulfide bonds, or an antigen-binding portion. Each heavy chain comprises a heavy chain variable region (abbreviated referred to herein as VH) and a heavy chain constant region. Known are five types of mammalian Ig heavy chain denoted by Greek letters: α, δ, ε, γ and μ. The type of a heavy chain present defines the class of an antibody; these chains are found in IgA, IgD, IgE, IgG, and IgM antibodies, respectively. Distinct heavy chains differ in size and composition; α and γ contain approximately 450 amino acids, while μ and ε have approximately 550 amino acids. Each heavy chain has two regions, the constant region and the variable region. The constant region is identical in all antibodies of the same isotype, but differs in antibodies of different isotypes. Heavy chains γ, α and δ have a constant region composed of three constant domains CH1, CH2 and CH3 (in a line), and a hinge region for added flexibility (Woof J., Burton D., Nat Rev Immunol 4, 2004, cc. 89-99); heavy chains μ and ε have a constant region composed of four constant domains CH1, CH2, CH3 and CH4. In mammals, known are only two types of light chain denoted by lambda (λ) and kappa (κ). Each light chain consists of a light chain variable region (abbreviated referred to herein as VL) and light chain constant region. The approximate length of a light chain is 211 to 217 amino acids. Preferably, the light chain is a kappa (κ) light chain, and the constant domain CL is preferably C kappa (κ).

"Antibodies" according to the invention can be of any class (e.g., IgA, IgD, IgE, IgG, and IgM, preferably IgG), or subclass (e.g., IgG1, IgG2, IgG3, IgG4, IgA1 and IgA2, preferably IgG1).

VL and VH regions can be further subdivided into hypervariability regions called complementarity determining regions (CDRs), interspersed between regions that are more conserved, termed framework regions (FR). Each VH and VL is composed of three CDR and four FR, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody or "antigen-binding fragment" (or simply "antibody portion" or "antibody fragment"), as used herein, refers to one or more fragments of an antibody that retain the ability to specifically bind to an antigen. It has been shown that the antigen-binding function of an antibody can be performed by fragments of a full length antibody Examples of binding fragments which are included within the term "antigen-binding portion" of an antibody include (i) Fab-fragment monovalent fragment consisting of the VL, VH, CL and CH 1 domains; (ii) F(ab') 2 fragment, a bivalent fragment comprising two Fab-fragments linked by a disulfide bridge at the hinge region; (iii) Fd-fragment consisting of the VH and CH1 domains; (iv) Fv-fragment consisting of the VL and VH domains of a single arm of an antibody; (v) dAb-fragment (Ward et al., (1989) Nature 341:544-546), which consists of a VH/VHH domain; and (vi) extracted complementarity determining region (CDR). In addition, two regions of the Fv-fragment, VL and VH, are encoded by separate genes, they can be joined using recombinant methods using a synthetic linker that enables them to receive a single protein chain in which the VL and VH region are paired to form monovalent molecules (known as single chain Fv (scFv); see e.g., Bird et al. (1988) Science 242: 423-426; and Huston et al. (1988) Proc. Natl. Acad. Sci. USA 85:5879-5883). It is assumed that such single-stranded molecules are also included within the term "antigen-binding portion" of an antibody. These antibody fragments are obtained using conventional techniques known to those skilled in the art, and the fragments are screened in the same manner as are intact antibodies.

Preferably, the CDR of antigen-binding portion or the whole antibody antigen binding portion of the invention is derived from mouse, lama or human donor library or substantially of human origin with certain amino acid residues altered, e.g., substituted with different amino acid residues in order to optimize the properties of the specific antibodies, e.g., KD, koff, IC50, EC50, ED50. Preferably the framework regions of antibodies of the invention are of human origin or substantially of human origin (at least 80, 85, 90, 95, 96, 97, 98 or 99% of human origin).

In other embodiments, the antigen binding portion of the invention may be derived from other non-human species including mouse, lama, rabbit, rat or hamster, but not limited to. Alternatively, the antigen-binding region can be derived from the human species.

The term "variable domain" refers to the fact that certain portions of the variable domains greatly differ in sequence among antibodies. The V domain mediates antigen binding and determines specificity of each particular antibody for its particular antigen. However, the variability is not evenly distributed across the 110-amino acid span of the variable domains. Instead, the V regions consist of invariant fragments called framework regions (FRs) of 15-30 amino acids separated by shorter regions of extreme variability called "hypervariable regions" or CDR. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies. The constant domains are not involved directly in binding an antibody to an antigen, but exhibit various effector functions, such as participation of the antibody in antibody-dependent cellular cytotoxicity (ADCC).

The term "hypervariable region" as used herein refers to the amino acid residues of an antibody which are responsible for antigen binding. The hypervariable region generally comprises amino acid residues from a "complementarity determining region" or "CDR" and/or those residues from a "hypervariable loop".

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., Proc Natl Acad Sci USA, 94:412-417 (1997) and the stepwise in vitro affinity maturation method by Wu et al., Proc Natl Acad Sci USA 95:6037 6042 (1998).

"Framework regions" (FR) are those variable domain residues other than the CDR residues. Each variable domain typically has four FRs identified as FR1, FR2, FR3 and FR4. If the CDRs are defined according to Kabat, the light chain FR residues are positioned about at residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

The fragment crystallizable region ("Fc region, Fc") of an immunoglobulin is the "tail" region of an immunoglobulin molecule that interacts with cell surface Fc-receptor, as well as some proteins of the complement system. This property allows antibodies to activate the immune system. In IgG, IgA and IgD antibody isotypes, the Fc region is composed of two identical protein fragments, respectively, from the second and third constant domains of the two heavy chains; in IgM and IgE isotypes, the Fc region contains three heavy chain constant domains (CH domains 2-4) in each polypeptide chain.

An antibody of the present invention "which binds" a target antigen refers to an antibody capable of binding the antigen with sufficient affinity such that the antibody can be used as a diagnostic and/or therapeutic agent targeting a protein or cell expressing said antigen, and slightly cross-reacts with other proteins. According to analytical methods: fluorescence-activated cell sorting (FACS), radioimmunoassay (RIA) or ELISA, in such embodiments, the degree of antibody binding to a non-target protein is less than 10% of antibody binding to a specific target protein. With regard to the binding of an antibody to a target molecule, the term "specific binding" or "specifically binds to" or is "specific for" a particular polypeptide or an epitope on a particular polypeptide target means binding that is noticeably (measurably) different from a non-specific interaction (for example, in the case of bH1-44 or bH1-81, a non-specific interaction is binding to bovine serum albumin, casein, fetal bovine serum or neutravidin).

Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. As used herein, the term "specific binding" or "specifically binds to" or is "specific for" a particular polypeptide or an epitope on a particular polypeptide target can be described by a molecule having a Kd for the target of at least about 200 nM, or at least about 150 nM, or at least about 100 nM, or at least about 60 nM, or at least about 50 nM, or at least about 40 nM, or at least about 30 nM, or at least about 20 nM, or at least about 10 nM, or at least about 8 nM, or at least about 6 nM, or at least about 4 nM, or at least about 2 nM, or at least about 1 nM, or greater. In one embodiment, the term "specific binding" refers to binding where a molecule binds to a particular polypeptide or epitope on a particular polypeptide without substantially binding to any other polypeptide or polypeptide epitope.

The term "Ka" as used herein refers to the association (on) rate of a particular antibody-antigen interaction.

The term "Kd" as used herein refers to the dissociation (off) rate of a particular antibody-antigen interaction.

"Binding affinity" generally refers to the strength of the sum total of noncovalent interactions between a single binding site of a molecule (e.g., an antibody) and its binding partner (e.g., an antigen). Unless indicated otherwise, "binding affinity" refers to intrinsic (characteristic, true) binding affinity which reflects a 1:1 interaction between members of a binding pair (e.g., antibody and antigen). The affinity of a molecule X for its binding partner Y can generally be represented by the dissociation constant (Kd). The preferred Kd value is about 200 nM, 150 nM, 100 nM, 60 nM, 50 nM, 40 nM, 30 nM, 20 nM, 10 nM, 8 nM, 6 nM, 4 nM, 2 nM, 1 nM, or less. Affinity can be measured by common methods known in the art, including those described herein. Low-affinity antibodies generally bind an antigen slowly and tend to dissociate readily, whereas high-affinity antibodies generally bind an antigen faster and tend to remain bound longer. A variety of methods of measuring binding affinity are known in the art, any of which can be used for purposes of the present invention.

In one embodiment, "Kd" or "Kd value" is measured by using surface plasmon resonance assays using BIAcore™-2000 or BIAcore®-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. Antigen is diluted with 10 mM sodium acetate, pH 4.8, into 5 µg/ml (~0.2 µM) and then injected at a flow rate of 5 µl/minute to achieve approximately 10 response units (RU) of coupled protein. Following the administration of antigen, 1M ethanolamine solution is administered to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. On-rates (kon) and off-rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol. Biol. 293: 865-881. If the on rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody solution (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The term "koff" refers to the off rate constant of a particular interaction between a binding molecule and antigen. The off rate constant koff can be measured using bio-layer interferometry, for example, using Octet™ system.

"On-rate" or "kon" according to the present invention can be also measured by using the above surface plasmon resonance assays using BIAcore™-2000 or BIAcore®-3000 (BIAcore, Inc., Piscataway, N.J.) at 25° C. with immobilized antigen CM5 chips at ~10 relative units (response units, RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. Antigen is diluted with 10 mM sodium acetate, pH 4.8, into 5 µg/ml (~0.2 µM) and then injected at a flow rate of 5 µl/minute to achieve approximately 10 response units (RU) of coupled protein. Following the administration of antigen, 1M ethanolamine solution is administered to block unreacted groups.

Unless specified otherwise, the term "biologically active" and "biological activity" and "biological characteristics" with respect to a polypeptide of the invention means having the ability to bind to a biological molecule.

The term "biological molecule" refers to a nucleic acid, a protein, a carbohydrate, a lipid, and combinations thereof. In one embodiment, a biological molecule exists in nature.

Antibody fragments, such as Fab and F(ab')2 fragments, can be prepared from whole antibodies using conventional techniques, such as papain or pepsin digestion of whole antibodies. Moreover, antibodies, portions thereof and immunoadhesion molecules can be prepared using standard recombinant DNA techniques, for example, as described herein.

The term "recombinant antibody" is intended to refer to an antibody that is expressed in a cell or cell line comprising nucleotide sequence(s) encoding antibodies, wherein said nucleotide sequence(s) is not naturally associated with the cell.

As used herein, the term "variant antibody" is intended to refer to an antibody which has an amino acid sequence which differs from the amino acid sequence of a "parental" antibody thereof by virtue of adding, deleting and/or substituting one or more amino acid residues as compared to the sequence of a parental antibody. In a preferred embodiment, a variant antibody comprises at least one or more (e.g., one to twelve, e.g., two, three, four, five, six, seven, eight or nine, ten, eleven or twelve; in some embodiments, a variant antibody comprises from one to about ten) additions, deletions, and/or substitutions of amino acids as compared to a parental antibody. In some embodiments, such additions, deletions and/or substitutions are made in the CDRs of a variant antibody. Identity or homology with respect to the sequence of a variant antibody is defined herein as the percentage of amino acid residues in the variant antibody sequence that are identical to the parental antibody residues, after aligning the sequences and introducing gaps, if necessary, to achieve the maximum percent of sequence identity. A variant antibody retains the ability to bind to the same antigen, and preferably to an epytope, to which the parental antibody binds; and in some embodiments, at least one property or biological activity are superior to those of a parental antibody. For example, a variant antibody may have, e.g., a stronger binding affinity, longer half-life, lower IC50, or enhanced ability to inhibit antigen biological activity as compared to a parental antibody. The variant antibody of particular interest herein is one which displays at least 2 fold, (preferably at least 5 fold, 10 fold or 20 fold) enhancement in biological activity as compared to a parental antibody.

The term "bispecific antibody" refers to an antibody having an antigen-binding domain(s) that are capable of specific binding to two distinct epitopes on a single biological molecule or capable of specific binding to epitopes on two distinct biological molecules. A bispecific antibody is also referred to herein as having "dual specificity" or as being a "dual specificity" antibody.

In a broad sense, the term "chimeric antibody" is intended to refer to an antibody that comprises one or more regions of one antibody, and one or more regions of one or several other antibodies, typically, a partially human and partially non-human antibody, i.e. derived partially from a non-human animal, such as mice, rats, or the like vermin, or the Camelidae such as llama and alpaca. Chimeric antibodies are generally preferred over non-human antibodies in order to reduce the risk of a human anti-antibody immune response, e.g. a human anti-mouse antibody immune response in the case of a murine antibody. An example of a typical chimeric antibody is one in which the variable region sequences are murine sequences, while the constant region sequences are human. In the case of a chimeric antibody, the non-human parts may be subjected to further alteration in order to humanize the antibody.

The term "humanization" is intended to refer to the fact that when an antibody has a fully or partially non-human origin, for example, a mouse or llama antibody obtained by immunizing mice or lamas, respectively, with an antigen of interest, or is a chimeric antibody based on such an antibody of a mouse or llama, it is possible to substitute certain amino acids, in particular in the framework regions and constant domains of heavy and light chains, in order to avoid or minimize the immune response in humans. Antibodies interact with target antigens predominantly through amino acid residues that are located in the six heavy and light chain CDRs. For this reason, amino acid sequences within CDRs are far more variable between individual antibodies than those outside of CDRs. Because CDR sequences are responsible for most antibody-antigen interactions, it is possible to express recombinant antibodies that mimic the properties of a specific naturally occurring antibody, or more generally, of any specific antibody with said amino acid sequence, e.g., by constructing expression vectors that express CDR sequences from the specific antibody and framework sequences from a different antibody. As a result, it is possible to "humanize" a non-human antibody and, to a large extent, preserve binding specificity and affinity of the initial antibody. Although it is not possible to precisely predict the immunogenicity and thereby the human anti-antibody response of a particular antibody, non-human antibodies are typically more immunogenic than human antibodies. Chimeric antibodies, where the foreign (e.g. vermin or Camelidae) constant regions have been substituted with sequences of human origin, have shown to be generally less immunogenic than those of fully foreign origin, and the trend in therapeutic antibodies is towards humanized or fully human antibodies. Therefore, chimeric antibodies or other antibodies of non-human origin can be humanized to reduce the risk of a human anti-antibody response.

For chimeric antibodies, humanization typically involves modification of the framework regions of variable region sequences. Amino acid residues that are part of complementarity determining regions (CDRs) will be most often not modified by virtue of humanization, although in some cases it may be desirable in order to modify individual amino acid residues of a CDR, for example, in order to delete a glycosylation site, deamidation site, aspartate isomerization site, or undesired cysteine or methionine residues. N-linked glycosylation is made by virtue of attaching an oligosaccharide chain to an asparagine residue in a tripeptide sequence Asn-X-Ser or Asn-X-Thr, where X can be any amino acid except Pro. Removal of an N-glycosylation site may be achieved by mutating either the Asn or Ser/Thr residue by a different residue, preferably by way of conservative substitution. Deamidation of asparagine and glutamine residues can occur depending on such factors as pH and surface exposure. Asparagine residues are especially susceptible to deamidation, primarily when present in sequence Asn-Gly, and in a lesser degree in other dipeptide sequences such as Asn-Ala. Provided a CDR sequence comprises such a deamidation site, in particular Asn-Gly, it may be desirable to remove this site, typically by virtue of conservative substitution to delete one of the implicated residues.

Numerous methods for humanization of an antibody sequence are known in the art. One commonly used method is CDR grafting. CDR grafting may be based on the CDR definitions by Kabat, although the last edition (Magdelaine-Beuzelin et al., Crit Rev. Oncol Hematol. 64:210 225 (2007)) suggests that the IMGT® (the international ImMunoGeneTics information System®, www.imgt.org) definition may improve humanization results (see Lefranc et al., Dev. Comp Immunol. 27:55-77 (2003)). In some cases, CDR grafting may reduce the binding specificity and affinity, and thus the biological activity, of a CDR grafted non-human antibody, as compared to a parental antibody from which the CDRs were obtained. Back mutations (which are sometimes referred to as "framework region repair" may be introduced at selected positions of a CDR grafted antibody, typically in framework regions, in order to restore the binding specificity and affinity of a parental antibody. Identification of positions for possible back mutations can be performed using information available in the literature and in antibody databases. Amino acid residues that are candidates for back mutations are typically those that are located at the surface of an antibody molecule, whereas residues that are buried or that have a low degree of surface exposure will not normally be altered. An alternative humanization technique to CDR grafting and back mutation is resurfacing, in which non-surface exposed residues of non-human origin are retained, whereas surface residues are altered to human residues.

Fully human antibodies can be generated using two techniques: using in vitro collected phage libraries or in vivo immunization of humanized animals (mice, rats, etc.).

The Construction of combinatorial phage antibody libraries begins with selection of a source of gene repertoire, depending on which several antibody library types can be distinguished: naive, immune and synthetic. Naive and immune libraries are constructed using naturally reorganized genes, which encode the variable immunoglobulin domains of healthy donors or donors immunized with a certain antigen, respectively. The mRNA from the antibody-producing lymphoid cell line is isolated for this purpose. Peripheral blood lymphocytes are mainly used, but splenocytes have been used as well [Sheets M D, Amersdorfer P, Finnern R, Sargent P, Lindquist E, Schier R, et al. Efficient construction of a large nonimmune phage antibody library: the production of high-affinity human single-chain antibodies to protein antigens. Proc Natl Acad Sci USA 1998, 95:6157-6162 and de Haard H J, van Neer N, Reurs A, Hufton S E, Roovers R C, Henderikx P, et al. A large non-immunized human Fab fragment phage library that permits rapid isolation and kinetic analysis of high affinity antibodies. J Biol Chem 1999, 274:18218-18230.], tonsillar cells or bone marrow lymphocytes [Vaughan T J, Williams A J, Pritchard K, Osbourn J K, Pope A R, Earnshaw J C, et al. Human antibodies with sub-nanomolar affinities isolated from a large non-immunized phage display library. Nat Biotechnol 1996, 14:309-314.]. The cDNA is then synthesized on the base of mRNA, and both oligo-dT primers and statistically devised hexanucleotides can be used that yield cDNA copies of all the possible variants of genes encoding the variable domains of antibodies [Ulitin A B, Kapralova M V, Laman A G, Shepelyakovskaya A O, Bulgakova E B, Fursova K K, et al. The library of human miniantibodies in the phage display format: Designing and testing DAN: Izd-vo "Nauka"; 2005.].

One or several primers can be simultaneously used to limit the range of amplified genes to one or several variable domain gene families or antibody isotypes, now at cDNA level [Marks J D, Hoogenboom H R, Bonnert T P, McCafferty J, Griffiths A D, Winter G. Bypassing immunization. Human antibodies from V-gene libraries displayed on phage. J Mol Biol 1991, 222:581-597]. The primers used for amplification of genes encoding immunoglobulins are complementary to their most conservative regions. Their sequences are selected from gene collections that are organized into databases, such as Kabat or V BASE databases. The primer design also provides for internal restriction sites for cloning the PCR-products into the appropriate vectors.

The construction of synthetic libraries is based on replacement of natural CDRs with a set of random sequences. In this case, it is possible to generate a vast variety of antigen-binding sites.

The Phage display is one of the most powerful and widely used in vitro technique for search for antibodies. In 1985, Smith found that foreign DNA sequences could be cloned into filamentous bacteriophage M13 and that such cloned sequence can be expressed on the surface of phage particles as fusion proteins (Smith G P: Filamentous fusion phage: novel expression vectors that display cloned antigens on the virion surface. Science 1985, 228:1315-1317.). Thus, it is possible to select the fusion proteins of interest based on their ability to bind other proteins. This discovery was combined with PCR amplification methods, which made it possible to clone the cDNA repertoire of immunoglobulin genes to create a variety of phage libraries containing variable domains that can be used to quickly search for target-specific monoclonal antibodies. Phage library repertoire reflects B-cell antibody repertoire of each human or animal whose blood was used to create the library. In 1995, two papers reported the generation of genetically engineered mice that expressed fully human antibody repertoires that could be comparable to those produced by the hybridoma technology (Lonberg N, Taylor L D, Harding F A, Trounstine M, Higgins K M, Schramm S R, Kuo C C, Mashayekh R, Wymore K, McCabe J G et al.: Antigen-specific human antibodies from mice comprising four distinct genetic modifications. Nature 1994, 368:856-859). In these animals, their own endogenous heavy and k light immunoglobulin chain genes were deliberately destroyed, followed by introduction of transgenes, which are the segments of human heavy and k light chain genes. It turned out that human gene repertoire can be used by the mouse immune system to produce high specificity and high affinity antibodies against a greater variety of antigens. Despite the fact that transgenic mice express B-cell receptors that are essentially hybrids of mouse and human components (human immunoglobulin, mouse Igα, Igβ, and other signaling molecules), their B-cells develop and mature normally.

The term "monoclonal antibody" or "mAb" refers to an antibody that is synthesized and isolated by a separate clonal population of cells. A clonal population can be a clonal population of immortalized cells. In some embodiments, the immortalized cells in a clonal population are hybrid cells—hybridomas—typically produced by the fusion of individual B lymphocytes from immunized animals with individual cells from a lymphocytic tumour. Hybridomas are a type of constructed cells and do not exist in nature.

"Native antibodies" are usually heterotetrameric glycoproteins of about 150000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "isolated" used to describe various antibodies in this description refers to an antibody which has been identified and separated and/or regenerated from a cell or cell culture, in which the antibody is expressed. Impurities (contaminant components) from its natural environment are materials which would interfere with diagnostic or therapeutic uses of the polypeptide, and may include enzymes, hormones, and other proteinaceous or nonproteinaceous solutes. In preferred embodiments, an antibody is purified (1) to a degree sufficient to obtain at least 15 residues of N-terminal or internal amino acid sequence by use of a spinning cup sequenator (Edman sequenator), or (2) to homogeneity by SDS-PAGE under nonreducing or reducing conditions using Coomassie Brilliant Blue, or preferably silver stain. Isolated antibody includes the antibody in situ within recombinant cells since at least one component of the polypeptide's natural environment will not be present. Isolated polypeptide is typically prepared by at least one purification step.

An "isolated" nucleic acid molecule is one which is identified and separated from at least one nucleic acid molecule-impurity, which the former is bound to in the natural source of antibody nucleic acid. An isolated nucleic acid molecule is different from the form or set in which it is found under natural conditions. Thus, an isolated nucleic acid molecule is different from a nucleic acid molecule that exists in cells under natural conditions. An isolated nucleic acid molecule however includes a nucleic acid molecule located in cells in which the antibody is normally expressed, for example, if the nucleic acid molecule has a chromosomal localization that is different from its localization in cells under natural conditions.

The term "epitope" as used herein is intended to refer to a portion (determinant) of an antigen that specifically binds to a binding molecule (for example, an antibody or a related molecule, such as a bispecific binding molecule). Epitope determinants usually consist of chemically active surface groupings of molecules such as amino acids or carbohydrates or sugar side chains and tipically comprise specific three dimensional structural characteristics, as well as specific charge characteristics. Epitopes can be either "linear" or "conformational". In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope of an antigen is determined, it is possible to generate antibodies to that epitope using techniques well known in the art. In addition, generation and characterization of antibodies or other binding molecules may elucidate information about desirable epitopes. From this information, it is then possible to competitively screen antibodies for binding to the same or identical epitopes, e.g., by conducting competition studies to find binding molecules that compete with one another for binding to the antigen.

The term "peptide linker" as used herein is intended to mean any peptide having the ability to combine domains, with a length which depends on the domains which it binds to each other, and comprising any amino acid sequence. Preferably, the peptide linker has a length of more than 5 amino acids and consists of any set of amino acids selected from G, A, S, P, E, T, D, K.

The term "in vitro" refers to a biological entity, a biological process, or a biological reaction outside the body under artificial conditions. For example, a cell grown in vitro is to be understood as a cell grown in an environment outside the body, e.g., in a test tube, a culture vial, or a microtiter plate.

The term "$IC_{50}$" (inhibitory concentration 50%), as used herein, refers to concentrations of drug, at which a measurable activity or response, for example, growth/proliferation of cells such as tumor cells, is inhibited by 50%. $IC_{50}$ value can be calculated using appropriate dose-response curves, using special statistical software for curve fitting.

The term "$IC_{50}$" (50% inhibitory concentration or half-maximal inhibitory concentration) refers to drug concentration and indicates inhibitor volume required to inhibit a biological process by 50%. $IC_{50}$ value can be calculated using appropriate dose-response curves, using special statistical software for curve fitting.

The term GI50 (growth inhibition 500) refers to concentrations of drug, at which proliferation of cells, such as tumor cells, is inhibited by 50%.

The term "ED50" (EC50) (50% effective dose/concentration) refers to concentrations of drug producing 50% biological effect (which may include cytoxicity).

The term "antiproliferative activity" is intended to refer to stopping or inhibiting growth of cells, such as cancer cells.

The term antibody "effector function" refers to biological activities attributable to the Fc-region (native Fc-region sequence or Fc-region amino acid variants) of an antibody, which vary with the antibody isotype. Examples of antibody effector functions include: $Cl_q$ binding and complement dependent cytotoxicity; Fc receptor binding; antibody-dependent cell-mediated cytotoxicity (ADCC); phagocytosis; down regulation of cell surface receptors (e.g., B-cell receptor, BCR), and B-cell activation.

"Antibody-dependent cellular cytotoxicity" or "ADCC" refers to a cell-mediated response, in which nonspecific cytotoxic cells that express Fc receptors (FcR) (for example, natural killer (NK) cells, neutrophils, and macrophages) recognize bound antibody on a target cell and subsequently cause lysis or phagocytosis of the target cell. The primary cells for mediating ADCC, NK cells, express FcγRJII only, whereas monocytes express FcγRI, FcγRII and FcγRIII. FcR expression on hematopoietic cells is summarized in Table 3 on page 464 of Ravetch and Kinet, Annu. Rev. Immunol 9: 457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95: 652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g., from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA ("activating receptor") and FcγRIIB ("inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daeron, Annu. Rev. Immunol. 15: 203-234 (1997)). FcRs are reviewed in Ravetch and Kinet, Annu. Rev. Immunol 9: 457-92 (1991). Other FcRs, including those to be identified in the future, are encompassed by the term "FcR" herein. The term also includes the neonatal receptor, FcRn, which is responsible for the transfer of maternal IgGs to the fetus.

"Complement dependent cytotoxicity" and "CDC" refer to the ability of a molecule to lyse a target in the presence of complement. The complement activation pathway is initiated by the binding of the first component of the complement system (C1q) to a molecule {e.g., an antibody) complexed with a cognate antigen. To assess complement activation, a CDC assay, e.g., as described in Gazzano-Santoro et al., J. Immunol. Methods 202: 163 (1996).

The term "identity" or "homology" is construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions will be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, WI 53705). This software matches similar sequences by assigning a degree of homology to various substitutions, deletions (eliminations), and other modifications.

The term "homologous" with regard to a polypeptide sequence of an antibody should be construed as an antibody exhibiting at least 70%, preferably 80%, more preferably 90% and most preferably 95% sequence identity relative to a polypeptide sequence. The term in relation to a nucleic acid sequence should be construed as a sequence of nucleotides exhibiting at least 85%, preferably 90%, more preferably 95% and most preferably 97% sequence identity relative to a nucleic acid sequence.

Modification(s) of amino acid sequences of antibodies described herein are provided. For example, it may be desirable to improve the binding affinity and/or other biological properties of the antibody. Amino acid sequence variants of antibody are prepared by introducing appropriate nucleotide changes into the antibody nucleic acid, or by peptide synthesis. Such modifications include, for example, deletions, and/or insertions and/or substitutions of residues within the amino acid sequences of antibody. Any combination of deletion, insertion, and substitution is made to arrive at the final construct, provided that the final construct possesses the desired characteristics. The amino acid changes also may alter post-translational processes in the antibody, such as changing the number or position of glycosylation sites.

Variant of modification of amino acid sequences of antibodies using amino acid substitutions. Such a variant is substitution of at least one amino acid residue in the antibody molecule with a different residue. The sites of greatest interest for substitutional mutagenesis include hypervariable regions or CDRs, but FR or Fc alterations are also contemplated. Conservative substitutions are shown in Table A under "preferred substitutions". If such substitutions cause alteration of the biological activity, further substantial changes can be made, which are denoted as "exemplary substitutions" set forth in Table A, or alterations described in more detail below when describing amino acid classes, and also product screening may be performed.

TABLE A

| Original residue | Exemplary substitutions | Preferred substitutions |
| --- | --- | --- |
| Ala (A) | Val; Leu; Ile | Val |
| Arg (R) | Lys; Gin; Asn | Lys |

TABLE A-continued

| Original residue | Exemplary substitutions | Preferred substitutions |
| --- | --- | --- |
| Asn (N) | Gin; His; Asp, Lys; Arg | Gin |
| Asp (D) | Glu; Asn | Glu |
| Cys (C) | Ser; Ala | Ser |
| Gln (Q) | Asn; Glu | Asn |
| Glu (E) | Asp; Gin | Asp |
| Gly (G) | Ala | Ala |
| His (H) | Asn; Gin; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gin; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-strand DNA or RNA, a single-strand DNA or RNA, or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Thus, isolated nucleic acids obtained by recombinant genetics, by means, for example, of host cells, or obtained by chemical synthesis should also be mentioned here.

A reference to a nucleotide sequence encompasses the complement thereof unless otherwise specified. Thus, a reference to a nucleic acid having a particular sequence should be understood as one which encompasses the complementary strand thereof with the complementary sequence thereof.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader sequence is operably linked to DNA for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

The term "vector" as used herein means a nucleic acid molecule capable of transporting another nucleic acid to which it has been linked. In some embodiments, a vector is a plasmid, i.e., a circular double stranded piece of DNA into which additional DNA segments may be ligated. In some embodiments, a vector is a viral vector, wherein additional DNA segments may be ligated into the viral genome. In some embodiments, vectors are capable of autonomous replication in a host cell into which they are introduced (e.g., bacterial vectors having a bacterial origin site of replication and episomal mammalian vectors). In further embodiments, vectors (e.g., non-episomal mammalian vectors) can be integrated into the genome of a host cell upon introduction into a host cell, and thereby are replicated along with the host gene. Moreover, certain vectors are capable of directing the expression of genes to which they are operably linked. Such vectors are referred to herein as "recombinant expression vectors" (or simply, "expression vectors").

The term "recombinant host cell" (or simply "host cell") as used herein is intended to refer to a cell into which a recombinant expression vector has been introduced. The present invention relates to host cells, which may include, for example, a vector according to the invention described above. The present invention also relates to host cells that comprise, for example, a nucleotide sequence encoding a heavy chain or antigen-binding portions thereof, a light chain-encoding nucleotide sequence or antigen-binding portions thereof, or both, of the first binding domain and/or second binding domain of a binding molecule of the invention. It should be understood that "recombinant host cell" and "host cell" are intended to refer not only to a particular subject cell but to the progeny of such a cell as well. Since modifications may occur in succeeding generations due to either mutation or environmental influences, such progeny may not, in fact, be identical to a parental cell, however, such cells are still included within the scope of the term "host cell" as used herein.

The term "excipient" is used herein to describe any ingredient other than the compound(s) of the invention.

The term "disease or disorder mediated by CD20" refers to any disease or disorder that is either directly, or indirectly associated with CD20, including etiology, development, progression, persistence or pathology of a disease or disorder. "Treat", "treating" and "treatment" refer to a method of alleviating or abrogating a biological disorder and/or at least one of attendant symptoms thereof. As used herein, to "alleviate" a disease, disorder or condition means reducing the severity and/or occurrence frequency of the symptoms of a disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

The term "disorder" means any condition that would benefit from treatment with the compound of the present invention. This means chronic and acute disorders or diseases including those pathological conditions that predispose the mammal to the disorder in question.

The terms "cancer" and "cancerous" refer to a physiological condition or describe a physiological condition in mammals that is typically characterized by unregulated growth/proliferation of cells. The definition encompasses both benign and malignant cancerous diseases. Examples of cancerous diseases include, but are not limited to, carcinoma, lymphoma, blastoma, sarcoma, and leukemia. More particular examples of such cancerous diseases include squamous cell cancer, small-cell lung cancer, non-small cell lung cancer, adenocarcinoma of the lung and squamous carcinoma of the lung, peritoneal cancer, hepatocellular cancer, stomach cancer including gastrointestinal cancer, pancreatic cancer, glioblastoma, glioma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, and various head and neck cancers.

The terms "immune response", "autoimmune response" and "autoimmune inflammation" refer, for example, to the action of lymphocytes, antigen-presenting cells, phagocytic cells, granulocytes and soluble macromolecules produced by said cells or liver cells (including antibodies, cytokines and complement produced in the result of selective damage, destruction or elimination of invasive pathogens, cells or tissues infected with pathogens, cancer cells or, in cases of autoimmunity or pathological inflammation, normal cells or tissues from the human body).

The terms "immune response", "autoimmune response" and "autoimmune inflammation" refer, for example, to the action of lymphocytes, antigen-presenting cells, phagocytic cells, granulocytes and soluble macromolecules produced by said cells or liver cells (including antibodies, cytokines and complement produced in the result of selective damage, destruction or elimination of invasive pathogens, cells or tissues infected with pathogens, cancer cells or, in cases of autoimmunity or pathological inflammation, normal cells or tissues from the human body).

As used herein, the term "autoantibodies" refers to antibodies directed against self-antigens. Self-antigens include but are not limited to nucleic acids (e.g., double-stranded DNA or RNA, single-stranded DNA or RNA, or a combination thereof), nuclear proteins (e.g., SS-A (Ro), SS-B(La), Scl-70, centromeres, Jo-1, histadyl-tRNA synthetase, threonyl-tRNA synthetase, PM-1, Mi-2, histones, and chromatin), cellular receptors (e.g., acetylcholine receptor, thyroid-stimulating hormone receptor), cellular proteins (e.g., cardiolipin, β2GP1), cell membrane proteins (e.g., aquaporin, desmoglein), RNA protein complexes (e.g., RNP and Sm), erythrocytes and platelet receptor glycoproteins.

The term "autoimmune disease" as used herein refers to a non-malignant disease or disorder arising from and directed against an individual's own (self) antigens and/or tissues.

The term encompasses, but is not limited to, rheumatoid arthritis, juvenile chronic arthritis, septic arthritis, Lyme osteoarthritis, psoriatic arthritis, reactive arthritis, spondyloarthropathy, systemic lupus erythematosus, Crohn's disease, ulcerative colitis, inflammatory bowel disease, diabetes mellitus, thyroiditis, asthma, allergic diseases, psoriasis, atopic dermatitis, scleroderma, reaction "graft versus host", organ transplant rejection, acute or chronic immune disease associated with organ transplantation, sarcoidosis, Kawasaki disease, Graves disease, nephrotic syndrome, chronic fatigue syndrome, Wegener's granulomatosis, Henoch-Schonlein purpura, microscopic renal vasculitis, chronic active hepatitis, uvenita, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, adult (acute) respiratory distress syndrome, alopecia, alopecia areata, seronegative arthropathy, arthropathy, Reiter's disease, psoriatic arthropathy associated with ulcerative colitis arthropathy, atopic allergy, autoimmune bullous diseases, pemphigus vulgaris, sheet-like pemphigus, pemphigoid disease, linear IgA, IgG-associated diseases, autoimmune hemolytic anemia, Coombs-positive hemolytic anemia, pernicious anemia, juvenile pernicious anemia, cranial giant arteritis, arthritis, primary sclerosing hepatitis A, cryptogenic autoimmune hepatitis, fibrosis lung diseases, cryptogenic fibrosis alveolitis, post-inflammatory interstitial lung diseases, interstitial pneumonitis, chronic eosinophilic pneumonia, post-infectious interstitial lung diseases, gouty arthritis, autoimmune hepatitis, autoimmune hepatitis type I (classical autoimmune hepatitis or lupoid), autoimmune hepatitis type II, osteoarthritis, primary sclerosing cholangitis, psoriasis, idiopathic leucopenia, autoimmune neutropenia, renal NOS-disease, glomerulonephritis, microscopic renal vasculitis, discoid lupus erythematosus, idiopathic or NOS-male infertility [autoimmunity to sperm], multiple sclerosis (all subtypes), sympathetic ophthalmia, pulmonary hypertension secondary to connective tissue disease, Goodpasture syndrome, pulmonary manifestations of polyarthritis nodosa, acute rheumatic fever, rheumatoid spondylitis, ankylosing spondylitis, Still's disease, systemic scleroderma, localized scleroderma, Sjögren syndrome, Sjögren disease, Behcet's disease, ankylosing spondylitis, spondylarthritis, axial enthesitis, relapsing polychondritis, Takayasu's disease, autoimmune thrombocytopenia, idiopathic thrombocytopenia, autoimmune thyroid disease, autoimmune gastritis, polyglandular autoimmune syndrome, hyperthyroidism, Hashimoto's disease, autoimmune atrophic hypothyroidism, primary myxedema, phacogenic uveitis, primary vasculitis, vitiligo, acute liver disease, chronic liver disease, allergies, asthma, psychiatric disorders (including depression and schizophrenia), type Th2/type Th1-mediated diseases, conjunctivitis, allergic contact dermatitis, allergic rhinitis, deficiency of alpha-1-antitrypsin, amyotrophic lateral sclerosis, anemia, cystic fibrosis, disorders associated with cytokine therapy, demyelinating disease, dermatitis, iridocyclitis/uveitis/optic neuritis, ischemia-reperfusion injury, ischemic stroke, juvenile rheumatoid arthritis, autoimmune enteropathy, autoimmune hearing loss, autoimmune lymphoproliferative syndrome, autoimmune myocarditis, autoimmune cardiomyopathy, Coxsackie myocarditis, Dressler's syndrome, lupus nephritis, angioedema, including hereditary angioedema, urticaria, hidradenitis suppurativa, lichen planus, lichen sclerosis, *pityriasis* lichenoides, vitiligo, Addison's disease, autoimmune polyendocrine syndrome, autoimmune pancreatitis, celiac disease, microscopic colitis, antiphospholipid syndrome, autoimmune lymphoproliferative syndrome, cold agglutinin disease, essential cryoglobulinemia, Evans syndrome, pernicious anemia, red cell aplasia, CREST syndrome, eosinophilic fasciitis, Felty syndrome, overlap syndrome, chronic Lyme disease, Parry-Romberg syndrome, palindromic rheumatism, rheumatism, acute rheumatic fever, retroperitoneal syndrome, sarcoidosis, Schnitzler's syndrome, undifferentiated connective tissue disease, dermatomyositis, polymyositis, fibromyalgia, myasthenia gravis, neuromyotonia, acute disseminated encephalomyelitis, Guillain-Barré syndrome, Devic's disease, Hashimoto encephalopathy, Lambert-Eaton myasthenic syndrome, eosinophilic granulomatosis with polyangiitis leukocytoclastic vasculitis, lupus vasculitis, rheumatoid vasculitis, polyangitis nodosa, autoimmune premature ovarian failure and blepharitis. The antibody can also treat any combination of the above disorders.

"Therapeutically effective amount" is intended to refer to that amount of the therapeutic agent being administered which will relieve to some extent one or more of the symptoms of the disorder being treated.

The term "chronic" use refers to continued (uninterrupted) use of agent(s) as opposed to acute (transient) route of administration so as to sustain the initial therapeutic effect (activity) for a long period of time.

"Intermittent" use refers to treatment that is not carried out consistently without interruptions, but which is rather periodic in nature.

As used herein, the words "comprise," "have," "include," or variations such as "comprises," "comprising," "has," "having," "includes" or "including", and all grammatical variations thereof will be understood to imply the inclusion of a stated integer or group of integers but not the exclusion of any other integer or group of integers.

DISCLOSURE OF THE INVENTION

Antibody

The present invention relates to a monoclonal antibody that specifically binds to CD20.

In one aspect, the present invention relates to a monoclonal antibody or antigen-binding fragment thereof that specifically binds to CD20 and comprises:

```
1) a heavy chain variable domain comprising the
amino acid sequence
                                     (SEQ ID NO: 2)
EVQLVQPGAEVVKPGASVKVSCKASGYTFTSYNMHWVRQAPGRGLEWM

GAIYPGNGDTSYNQKFKGRVTMTRDKSTSTVYMELSSLRSEDTAVYYC

ARSTYYGGDWYFNVWGQGTLVTVSS;
or
                                     (SEQ ID NO: 6)
QVQLVQSGAEVKKPGASVKVSCKASGYTFTSYNMHWVRQAPGRGLEWM

GAIYPGNGDTSYNQKFKGRATLTRDTSTSTVYMELSSLRSEDTAVYYC

ARSTYYGGDWYFNVWGQGTLVTVSS;

2) a light chain variable domain comprising the
amino acid sequence
                                     (SEQ ID NO: 4)
QIVLSQSPAILSASPGERVTLTCRASSSVSYIHWFQQKPGKAPKPLIY

ATSNLASGVPSRFSGSGSGTDFSLTISRVEPEDFAVYYCQQWTSNPPT

FGGGTKVEIK
or
                                     (SEQ ID NO: 8)
QIVLSQSPATLSASPGERATMTCRASSSVSYIHWFQQKPGKAPKPLIY

ATSNLASGVPSRFSGSGSGTDFTLTISRLEPEDFATYYCQQWTSNPPT

FGGGTKVEIK.
```

In some embodiments, a monoclonal antibody or antigen-binding fragment thereof comprise:

```
1) a heavy chain variable domain comprising the
amino acid sequence
                                     (SEQ ID NO: 2)
EVQLVQPGAEVVKPGASVKVSCKASGYTFTSYNMHWVRQAPGRGLEWM

GAIYPGNGDTSYNQKFKGRVTMTRDKSTSTVYMELSSLRSEDTAVYYC

ARSTYYGGDWYFNVWGQGTLVTVSS;
```

2) a light chain variable domain comprising the amino acid sequence (SEQ ID NO: 4)
QIVLSQSPAILSASPGERVTLTCRASSSVSYIHWFQQKPGKAPKPLIY

ATSNLASGVPSRFSGSGSGTDFSLTISRVEPEDFAVYYCQQWTSNPPT

FGGGTKVEIK.

In some embodiments, a monoclonal antibody or antigen-binding fragment thereof comprise:

1) a heavy chain variable domain comprising the amino acid sequence (SEQ ID NO: 6)
QVQLVQSGAEVKKPGASVKVSCKASGYTFTSYNMHWVRQAPGRGLEWM

GAIYPGNGDTSYNQKFKGRATLTRDTSTSTVYMELSSLRSEDTAVYYC

ARSTYYGGDWYFNVWGQGTLVTVSS;

2) a light chain variable domain comprising the amino acid sequence (SEQ ID NO: 8)
QIVLSQSPATLSASPGERATMTCRASSSVSYIHWFQQKPGKAPKPLIY

ATSNLASGVPSRFSGSGSGTDFTLTISRLEPEDFATYYCQQWTSNPPT

FGGGTKVEIK.

In some embodiments, a monoclonal antibody comprises:

1) a heavy chain comprising the amino acid sequence (SEQ ID NO: 1)
EVQLVQPGAEVVKPGASVKVSCKASGYTFTSYNMHWVRQAPGRGLEWM

GAIYPGNGDTSYNQKFKGRVTMTRDKSTSTVYMELSSLRSEDTAVYYC

ARSTYYGGDWYFNVWGQGTLVTVSSASTKGPSVFPLAPSSKSTSGGTA

ALGCLVKDYFPEPVTVSWNSGALTSGVHTFPAVLQSSGLYSLSSVVTV

PSSSLGTQTYICNVNHKPSNTKVDKRVEPKSCDKTHTCPPCPAPELLG

GPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVM

HEALHNHYTQKSLSLSPGK
or (SEQ ID NO: 5)
QVQLVQSGAEVKKPGASVKVSCKASGYTFTSYNMHWVRQAPGRGLEWM

GAIYPGNGDTSYNQKFKGRATLTRDTSTSTVYMELSSLRSEDTAVYYC

ARSTYYGGDWYFNVWGQGTLVTVSSASTKGPSVFPLAPSSKSTSGGTA

ALGCLVKDYFPEPVTVSWNSGALTSGVHTFPAVLQSSGLYSLSSVVTV

PSSSLGTQTYICNVNHKPSNTKVDKRVEPKSCDKTHTCPPCPAPELLG

GPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVM

HEALHNHYTQKSLSLSPGK;

2) a light chain comprising the amino acid sequence (SEQ ID NO: 3)
QIVLSQSPAILSASPGERVILTCRASSSVSYIHWFQQKPGKAPKPLIY

ATSNLASGVPSRFSGSGSGTDFSLTISRVEPEDFAVYYCQQWTSNPPT

FGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC
or (SEQ ID NO: 7)
QIVLSQSPATLSASPGERATMTCRASSSVSYIHWFQQKPGKAPKPLIY

ATSNLASGVPSRFSGSGSGTDFTLTISRLEPEDFATYYCQQWTSNPPT

FGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC.

In some embodiments, a monoclonal antibody that specifically binds to CD20 is BCD132-077.

The monoclonal antibody BCD132-077 comprises:

1) a heavy chain comprising the amino acid sequence (SEQ ID NO: 1)
EVQLVQPGAEVVKPGASVKVSCKASGYTFTSYNMHWVRQAPGRGLEWM

GAIYPGNGDTSYNQKFKGRVTMTRDKSTSTVYMELSSLRSEDTAVYYC

ARSTYYGGDWYFNVWGQGTLVTVSSASTKGPSVFPLAPSSKSTSGGTA

ALGCLVKDYFPEPVTVSWNSGALTSGVHTFPAVLQSSGLYSLSSVVTV

PSSSLGTQTYICNVNHKPSNTKVDKRVEPKSCDKTHTCPPCPAPELLG

GPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVM

HEALHNHYTQKSLSLSPGK;

2) a light chain comprising the amino acid sequence (SEQ ID NO: 3)
QIVLSQSPAILSASPGERVILTCRASSSVSYIHWFQQKPGKAPKPLIY

ATSNLASGVPSRFSGSGSGTDFSLTISRVEPEDFAVYYCQQWTSNPPT

FGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC.

In some embodiments, a monoclonal antibody that specifically binds to CD20 is BCD132-L-028.

The monoclonal antibody BCD132-L-028 comprises:

1) a heavy chain comprising the amino acid sequence (SEQ ID NO: 5)
QVQLVQSGAEVKKPGASVKVSCKASGYTFTSYNMHWVRQAPGRGLEWM

GAIYPGNGDTSYNQKFKGRATLTRDTSTSTVYMELSSLRSEDTAVYYC

ARSTYYGGDWYFNVWGQGTLVTVSSASTKGPSVFPLAPSSKSTSGGTA

-continued

```
ALGCLVKDYFPEPVTVSWNSGALTSGVHTFPAVLQSSGLYSLSSVVTV

PSSSLGTQTYICNVNHKPSNTKVDKRVEPKSCDKTHTCPPCPAPELLG

GPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVM

HEALHNHYTQKSLSLSPGK;

2) a light chain comprising the amino acid
sequence
                                         (SEQ ID NO: 7)
QIVLSQSPATLSASPGERATMTCRASSSVSYIHWFQQKPGKAPKPLIY

ATSNLASGVPSRFSGSGSGTDFTLTISRLEPEDFATYYCQQWTSNPPT

FGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC.
```

In some embodiments, a monoclonal antibody that specifically binds to CD20 is a full-length IgG antibody.

In some embodiments, a monoclonal antibody is of human IgG1, IgG2, IgG3, IgG4 isotype.

In some embodiments, a monoclonal antibody is of human IgG1 isotype.

Nucleic Acid Molecules

The present invention also relates to nucleic acid molecules, in particular to sequences encoding a monoclonal antibody that specifically binds to CD20 according to the invention, as described herein, optionally including any peptide linker sequence, which are connected therewith.

A reference to a nucleotide sequence encompasses the complement thereof unless otherwise specified. Thus, a reference to a nucleic acid having a particular sequence should be understood as one which encompasses the complementary strand thereof with the complementary sequence thereof. The term "polynucleotide" as used herein means a polymeric form of either nucleotides that are at least 10 bases in length, or ribonucleotides, or deoxyribonucleotides or a modified form of either type of nucleotide. The term includes single and double stranded forms.

In one aspect, the present invention relates to a nucleic acid molecule comprising a nucleotide sequence encoding an amino acid sequence selected from SEQ ID NOs: 1-8. A nucleic acid molecule can also comprise any combination of said nucleotide sequences.

In one aspect, the present invention relates to a nucleic acid molecule comprising a nucleotide sequence that encodes a monoclonal antibody or antigen-binding fragment thereof that specifically binds to CD20 and comprises:
1) a heavy chain variable domain comprising an amino acid sequence shown in SEQ ID NO: 2 or SEQ ID NO: 6;
2) a light chain variable domain comprising an amino acid sequence shown in SEQ ID NO: 4 or SEQ ID NO: 8.

In some embodiments, a nucleic acid molecule comprises a nucleotide sequence that encodes a monoclonal antibody or antigen-binding fragment thereof that comprise:
1) a heavy chain variable domain comprising an amino acid sequence shown in SEQ ID NO: 2;
2) a light chain variable domain comprising an amino acid sequence shown in SEQ ID NO: 4.

In some embodiments, a nucleic acid molecule comprises a nucleotide sequence that encodes a monoclonal antibody or antigen-binding fragment thereof that comprise:
1) a heavy chain variable domain comprising an amino acid sequence shown in SEQ ID NO: 6;
2) a light chain variable domain comprising an amino acid sequence shown in SEQ ID NO: 8.

In some embodiments, a nucleic acid molecule comprises a nucleotide sequence that encodes a monoclonal antibody that comprises:
1) a heavy chain comprising an amino acid sequence shown in SEQ ID NO: 1 or SEQ ID NO: 5;
2) a light chain comprising an amino acid sequence shown in SEQ ID NO: 3 or SEQ ID NO: 7.

In some embodiments, a nucleic acid molecule comprises a nucleotide sequence that encodes a monoclonal antibody that comprises:
1) a heavy chain comprising an amino acid sequence shown in SEQ ID NO: 1;
2) a light chain comprising an amino acid sequence shown in SEQ ID NO: 3.

In some embodiments, a nucleic acid molecule comprises a nucleotide sequence that encodes a monoclonal antibody that comprises:
1) a heavy chain comprising an amino acid sequence shown in SEQ ID NO: 5;
2) a light chain comprising an amino acid sequence shown in SEQ ID NO: 7.

In any of the above embodiments, nucleic acid molecules can be isolated.

A nucleic acid molecule of the invention can be isolated from any source that produces a monoclonal antibody that specifically binds to CD20. In certain embodiments, a nucleic acid molecule of the invention can be synthesized, rather than isolated.

In one embodiment, nucleic acid molecules encoding VH (SEQ ID NO: 2 or SEQ ID NO: 6) or VL (SEQ ID NO: 4 or SEQ ID NO: 8) domains are transformed into antibody genes along the entire length by virtue of insertion into an expression vector already encoding heavy chain constant (CH) or light chain constant (CL) domains, respectively, such that the VH segment is operably linked to the CH segment(s) within the vector, and/or the VL segment is operably linked to the CL segment within the vector. In another embodiment, nucleic acid molecules encoding the VH and/or VL domains are transformed into genes along the entire length of antibody by virtue of linking, e.g. ligating, a nucleic acid molecule encoding VH and/or VL domains to a nucleic acid molecule encoding CH and/or CL domains using standard molecular biological techniques. Nucleic acid molecules encoding heavy and/or light chains along the entire length may then be expressed from a cell into which they have been introduced.

The nucleic acid molecules may be used to express a large quantity of recombinant monoclonal antibody that specifically binds to CD20.

Vector

In another aspect, the present invention relates to a vector suitable for the expression of any of nucleotide sequences described herein.

The present invention relates to vectors comprising nucleic acid molecules that encode any of the amino acid sequences of monoclonal antibody that specifically binds to CD20 or portions thereof (e.g. heavy chain sequences of a first binding domain and/or heavy and/or light chain sequences of a second binding domain), as described herein.

The invention further provides vectors comprising nucleic acid molecules encoding fusion proteins, modified antibodies, antibody fragments.

In some embodiments, a monoclonal antibody that specifically binds to CD20 according to the invention is expressed by inserting a DNA partially or fully encoding the sequence of a first or second binding domain (e.g. light and heavy chain sequences where a binding domain comprises light and heavy chain sequences), obtained as described above, in expression vectors such that the genes are operably linked to necessary expression control sequences, such as transcriptional and translational control sequences. The expression vectors include plasmids, retroviruses, adenoviruses, adeno-associated viruses (AAV), plant viruses, such as cauliflower mosaic virus, tobacco mosaic virus, cosmids, YACs, EBV derived episomes, and the like. DNA molecules may be ligated into a vector such that transcriptional and translational control sequences within the vector serve their intended function of regulating the transcription and translation of the DNA. An expression vector and expression control sequences may be chosen to be compatible with the expression host cell used. DNA molecules partially or fully encoding the sequences of first and second binding domains (for example, heavy and light chain sequences where a binding domain comprises a heavy and light chain sequence) can be introduced into individual vectors. In one embodiment, any combination of said DNA molecules is introduced into the same expression vector. DNA molecules can be introduced into an expression vector by standard methods (e.g., ligation of complementary restriction sites on an antibody gene fragment and vector, or blunt end ligation if no restriction sites are present).

A suitable vector is one that encodes functionally complete human CH or CL immunoglobulin sequences, with appropriate restriction site engineering so that any VH or VL sequence can easily be inserted and expressed, as described above. HC- and LC-encoding genes in such vectors may contain intron sequences that results in enhanced overall antibody protein yields by stabilizing the corresponding mRNA. The intron sequences are flanked by splice donor and splice acceptor sites, which determine where RNA splicing will occur. The location of intron sequences can be either in variable or constant regions of antibody chains, or in both variable and constant regions when multiple introns are used. Polyadenylation and transcription termination may occur at a native chromosomal site downstream of coding regions. A recombinant expression vector can also encode a signal peptide that facilitates secretion of an antibody chain from a host cell. An antibody chain gene may be cloned into a vector such that the signal peptide is linked in-frame to the amino terminus of an immunoglobulin chain. The signal peptide can be an immunoglobulin signal peptide or a heterologous signal peptide (i.e., a signal peptide from a non-immunoglobulin protein).

In addition to antibody chain genes, the recombinant vector expression of the invention can carry regulatory sequences that control the expression of antibody chain genes in a host cell. It will be understood by those skilled in the art that the design of an expression vector, including the selection of regulatory sequences, may depend on such factors as the choice of a host cell to be transformed, the level of expression of a desired protein, and so forth. Preferred control sequences for an expression host cell in mammals include viral elements that ensure high levels of protein expression in mammalian cells, such as promoters and/or enhancers derived from a retroviral LTR, cytomegalovirus (CMV) (such as a CMV promoter/enhancer), simian virus 40 (SV40) (such as a SV40 promoter/enhancer), adenovirus, (e.g., the major late promoter adenovirus (AdMLP)), polyomavirus and strong mammalian promoters such as native immunoglobulin promoter or actin promoter. For further description of viral control elements and sequences thereof, see, e.g., U.S. Pat. Nos. 5,168,062, 4,510,245 and 4,968,615. Methods for expressing binding molecules, such as antibodies in plants, including a description of promoters and vectors, as well as transformation of plants are known in the art. See, e.g., U.S. Pat. No. 6,517,529. Methods for expressing polypeptides in bacterial cells or fungal cells, e.g., yeast cells, are also well known in the art.

In addition to antibody chain genes and regulatory sequences, recombinant expression vectors of the invention may carry additional sequences, such as sequences that regulate replication of a vector in host cells (e.g. origins of replication) and selectable marker genes. The selectable marker gene facilitates the selection of host cells into which a vector has been introduced (see e.g. U.S. Pat. Nos. 4,399,216, 4,634,665 and 5,179,017). For example, typically the selectable marker gene confers resistance to medicinal agents, such as G418, hygromycin or methotrexate, on a host cell into which a vector has been introduced. For example, selectable marker genes include a dihydrofolate reductase (DHFR) gene (for use in dhfr-host cells during methotrexate selection/amplification), a neo gene (for G418 selection), and a glutamate synthetase gene.

The term "expression control sequence" as used herein is intended to refer to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of ribosome binding site, and transcription termination sequences; in eukaryotes, typically, such control sequences include promoters and transcription termination sequences. The term "control sequences" is intended to include at least all components, the presence of which is essential for expression and processing, and can also include additional components, the presence of which is advantageous, for example, leader sequences and fusion partner sequences.

Host Cells

A further aspect of the present invention relates to methods for producing a monoclonal antibody that specifically binds to CD20 according to the invention. One embodiment of the invention relates to a method for producing a monoclonal antibody that specifically binds to CD20, as defined herein, which comprises the production of a recombinant host cell capable of expressing a monoclonal antibody that specifically binds to CD20, culturing of said host cell under conditions suitable for expression/production of a monoclonal antibody that specifically binds to CD20, and isolation of a resulting monoclonal antibody that specifically binds to CD20. A monoclonal antibody that specifically binds to CD20 produced by such expression in such recombinant host cells is referred to herein as "a recombinant monoclonal antibody that specifically binds to CD20". The invention also relates to the progeny of cells from such host cells, and a monoclonal antibody that specifically binds to CD20 produced analogously.

Nucleic acid molecules encoding a monoclonal antibody that specifically binds to CD20 according to the invention and vectors comprising these nucleic acid molecules can be used for transfection of a suitable mammalian or cell thereof, plant or cell thereof, bacterial or yeast host cell. Transformation can be by any known technique for introducing polynucleotides into a host-cell. Methods for administration of heterologous polynucleotides into mammalian cells are well known in the art and include dextran-mediated transfection, cationic polymer-nucleic acid complex transfection, calcium phosphate precipitation, polybrene-mediated transfection, protoplast fusion, encapsulation of the polynucleotide(s) in liposomes, and direct microinjection of DNA into nuclei. In addition, nucleic acid molecules may be introduced into mammalian cells by viral vectors. Methods for transfecting cells are well known in the art. See, e.g., U.S. Pat. Nos. 4,399,216, 4,912,040, 4,740,461 and 4,959,455. Methods for transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines used as hosts for transformation are well known in the art and include a plurality of immortalized cell lines available. These include, e.g., Chinese hamster ovary (CHO) cells, NS0 cells, SP2 cells, HEK-293T cells, FreeStyle 293 cells (Invitrogen), NIH-313 cells, HeLa cells, baby hamster kidney (BHK) cells, African green monkey kidney cells (COS), human hepatocellular carcinoma cells (e.g., Hep G2), A549 cells, and a number of other cell lines. Cell lines are selected by determining which cell lines have high expression levels and provide for necessary characteristics of protein produced. Other cell lines that may be used are insect cell lines, such as Sf9 or Sf21 cells. When recombinant expression vectors encoding a monoclonal antibody that specifically binds to CD20 are introduced into mammalian host cells, the antibodies are produced by culturing the host cells for a period of time sufficient to allow for expression of the antibodies in host cells or, more preferably, secretion of the antibodies into the culture medium in which the host cells are grown. A monoclonal antibody that specifically binds to CD20 can be reconstituted from the culture medium using standard protein purification techniques. Plant host cells include, e.g., *Nicotiana, Arabidopsis*, duckweed, corn, wheat, potato, etc. Bacterial host cells include *Escherichia* and *Streptomyces* species. Yeast host cells include *Schizosaccharomyces pombe, Saccharomyces cerevisiae* and *Pichia pastoris*.

Furthermore, level of production of a monoclonal antibody that specifically binds to CD20 according to the invention from production cell lines can be enhanced using a number of known techniques. For example, the glutamine synthetase gene expression system (the GS system) is a common approach for enhancing expression under certain conditions. The GS system is discussed in whole or part in connection with EP Nos. 0216846, 0256055, 0323997 and 0338841.

It is likely that a monoclonal antibody that specifically binds to CD20 expressed by various cell lines or in transgenic animals will have a different glycosylation profile as compared to each other. However, monoclonal antibody that specifically binds to CD20 encoded by nucleic acid molecules described herein, or comprising amino acid sequences provided herein are part of the present invention, regardless of the glycosylation of the binding molecules, and, in general, regardless of the presence or absence of post-translational modifications.

Preparation of Antibodies

The invention also relates to methods and processes for producing a monoclonal antibody that specifically binds to CD20 and antigen-binding fragments thereof.

Monoclonal Antibodies

Monoclonal antibodies may be prepared using the hybridoma method first described by Kohler, et al. Nature 256, 1975, p. 495, or may be prepared using recombinant DNA methods (U.S. Pat. No. 4,816,567).

In a hybridoma method, a mouse, or other appropriate host animal, such as a hamster, is immunized according to the above method to elicit lymphocytes that produce or are capable of producing antibodies that will specifically bind to protein used for immunization. According to another embodiment, lymphocytes can be produced by in vitro immunization. After immunization, the lymphocytes are fused with a myeloma cell line using a suitable fusing agent, such as polyethylene glycol, to produce a hybridoma cell.

The hybridoma cells, produced in the above manner, may be cultured in a suitable culture medium that preferably contains one or more substances that inhibit the growth or survival of the unfused parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), i.e. substances which prevent the growth of HGPRT-deficient cells.

Preferred cells, used as component for myeloma cell fusion, are those that fuse efficiently, support stable high level production of antibodies by the selected antibody-producing cells, and are sensitive to a medium where the unfused parental cells are selected. The preferred myeloma cell lines are murine myeloma lines, such as those derived from MOPC-21 and MPC-11 mouse tumors available from the Salk Institute Cell Distribution Center, San Diego, California, USA, and SP-2 or X63-Ag8-653 cells available from the American Type Culture Collection, Rockville, Maryland, USA. Human myeloma and mouse-human heteromyeloma cell lines also have been described for the production of monoclonal antibodies (Kozbor, J. Immunol., 133, 1984, p. 3001).

Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal e.g, by intraperitoneal (i.p.) injection of the cells into mice.

The monoclonal antibodies secreted by the subclones can be separated from the culture medium, ascites fluid, or serum by conventional antibody purification techniques such as, for example, affinity chromatography (e.g., using protein A- or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of specific binding to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not produce antibody protein without being transfected, to obtain the synthesis of monoclonal antibodies in the recombinant host cells.

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992), as well as combinatorial infection and in vivo recombination as a strategy for constructing very large phage libraries (Waterhouse et al., Nucl. Acids. Res. 21:2265-2266 (1993). Thus, these techniques are viable alternatives to traditional monoclonal antibody hybridoma techniques for isolation of monoclonal antibodies.

The DNA that encodes an antibody may be modified, for example, so as to produce chimeric or fusion antibody polypeptides, for example, by substituting heavy chain and light chain (CH and CL) constant region sequences for the homologous murine sequences (U.S. Pat. No. 4,816,567 and Morrison, et al., Proc. Natl. Acad. Sci. USA: 81:6851 (1984), or by covalently fusing the immunoglobulin coding sequence with all or part of the coding sequence of a non-immunoglobulin polypeptide (heterologous polypeptide). The non-immunoglobulin polypeptide sequences can be substituted for the constant regions of antibody, or they can be substituted for the variable domains of antigen-binding center of antibody to create a chimeric bivalent antibody comprising one antigen-binding site having specificity for an antigen and another antigen-binding site having specificity for a different antigen.

Human Antibodies and Methodology Based on Phage Display Library

It is now possible to produce transgenic animals (e.g. mice) that are capable, after immunization, of producing a full range of human antibodies without endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice results in the production of human antibodies after antigen challenge (U.S. Pat. Nos. 5,545,806, 5,569,825, 5,591,669 (all of GenPharm); 5545807; and WO 97/17852).

Alternatively, phage display technology (McCafferty et al., Nature, 348:552-553 (1990) can be used to produce human antibodies and antibody fragments in vitro from immunoglobulin variable (V) region gene repertoire from immunized donor bodies. According to this technique, antibody V-region genes are cloned in-frame with either a major or minor coat protein gene of a filamentous bacteriophage, such as M13 or fd, and displayed as functional antibody fragments on the surface of a phage particle. Because the filamentous particle contains a single-stranded DNA copy of the phage genome, selections based on the functional properties of the antibody also result in selection of a gene encoding an antibody exhibiting said properties. Thus, the phage mimics some of B cell properties. Phage display can be performed in a variety of formats. Several sources of V-gene segments can be used for phage display. Clackson et al., Nature, 352:624-628 (1991) isolated various arrays of anti-oxazolone antibodies from a small random combinatorial library of V genes derived from the spleen of immunized mice. A repertoire of V genes from unimmunized human donors can be constructed and antibodies against a diverse array of antigens (including self-antigens) can be isolated essentially following the techniques described by Marks et al., J. Mol. Biol. 222:581-597 (1991).

As described above, human antibodies may also be generated by in vitro activated B cells (see U.S. Pat. Nos. 5,567,610 and 5,229,275).

Antibody Fragments

In certain circumstances, it is advisable to use antibody fragments rather than whole antibodies. The small sizes of the fragments contributes to rapid clearance thereof and may contribute to better penetration into dense tumors.

Various techniques have been developed for the production of antibody fragments. Traditionally, these fragments were derived via proteolytic digestion of intact antibodies. However, these fragments can now be produced directly by recombinant host cells. Fab, Fv and ScFv antibody fragments can be expressed in and secreted from E. coli, thus allowing to facilitate the production of large amounts of these fragments. Antibody fragments can be isolated from the antibody phage libraries described above. According to another embodiment, Fab'-SH fragments can be directly isolated from E. coli and chemically coupled to form F(ab')$_2$ fragments (Carter et al., Bio/Technology 10:163-167 (1992). According to another approach, F(ab')$_2$ fragments can be isolated directly from recombinant host cell culture. Fab and F(ab')$_2$ with increased in vivo half-life retaining epitope binding receptor residues are described in U.S. Pat. No. 5,869,046. Other techniques for the production of antibody fragments will be apparent to those skilled in the art. In other embodiments, the antibody of choice is a single chain Fv fragment (scFv) (see WO 93/16185; U.S. Pat. Nos. 5,571, 894 and 5,587,458). Fv and scFv are the only species with intact binding sites that are devoid of constant regions; as a result, they are suitable for reduced nonspecific binding during in vivo use. scFv fusion proteins may be constructed to yield fusion of an effector protein at either N- or C-terminus of an scFv. The antibody fragment may also be a "linear antibody", e.g., as described in U.S. Pat. No. 5,641, 870. Such linear antibody fragments may be monospecific or bispecific.

Pharmaceutical Compositions

In another aspect, the invention provides a pharmaceutical composition comprising a monoclonal antibody that specifically binds to CD20 as an active ingredient (or as the only active ingredient).

A pharmaceutical composition may include at least one monoclonal antibody that specifically binds to CD20 and at least one of components selected from the group consisting of pharmaceutically acceptable and pharmacologically compatible excipients.

A pharmaceutical composition may include at least one monoclonal antibody that specifically binds to CD20 and one or more additional binding molecules (e.g., antibodies) that target one or more of the corresponding surface receptors. In some embodiments, compositions are intended to improve, prevent, or treat disorders that may be associated with CD20.

"Pharmaceutical composition" means a composition comprising a monoclonal antibody that specifically binds to CD20 according to the invention and at least one of components selected from the group consisting of pharmaceutically acceptable and pharmacologically compatible excipients, such as fillers, solvents, diluents, carriers, auxiliary, distributing agents, delivery agents, preservatives, stabilizers, emulsifiers, suspending agents, thickeners, prolonged delivery controllers, the choice and proportions of which depend on the type and route of administration and dosage. Pharmaceutical compositions of the present invention and methods of preparation thereof will be undoubtedly apparent to those skilled in the art. The pharmaceutical compositions should preferably be manufactured in compliance with the GMP (Good Manufacturing Practice) requirements. A composition may comprise a buffer composition, tonicity agents, stabilizers and solubilizers. Prolonged action of a composition may be achieved by agents slowing down absorption of active pharmaceutical ingredient, for example, aluminum monostearate and gelatine. Examples of suitable carriers, solvents, diluents and delivery agents include water, ethanol, polyalcohols and their mixtures, oils, and organic esters for injections.

"Medicament (drug)"—is a compound or a mixture of compounds as a pharmaceutical composition in the form of tablets, capsules, powders, lyophilisates, injections, infusion, ointments and other ready forms intended for restoration, improvement or modification of physiological functions in humans and animals, and for treatment and preventing of diseases, for diagnostics, anesthesia, contraception, cosmetology and others. Any method for administering peptides, proteins or antibodies which is accepted in the art may be suitably employed for a monoclonal antibody that specifically binds to CD20 according to the invention.

The term "pharmaceutically acceptable" refers to one or more compatible liquid or solid components that are suitable for administration in a mammal, preferably a human.

The term "excipient" is used herein to describe any ingredient other than the above ingredients of the invention. These are substances of inorganic or organic nature which are used in the pharmaceutical manufacturing in order to give drug products the necessary physicochemical properties.

The terms "buffer", "buffer composition", "buffering agent" refers to a solution, which is capable of resisting changes in pH by the action of its acid-base conjugate components, and which allows the drug of a monoclonal antibody that specifically binds to CD20 to resist changes in pH. Generally, the pharmaceutical composition preferably has a pH in the range from 4.0 to 8.0. Examples of buffers used include, but are not limited to, acetate, phosphate, citrate, histidine, succinate, etc. buffer solutions.

The terms "tonic agent", "osmolyte" or "osmotic agent", as used herein, refer to an excipient that can increase the osmotic pressure of a liquid antibody formulation. "Isotonic" drug is a drug that has an osmotic pressure equivalent to that of human blood. Isotonic drugs typically have an osmotic pressure from about 250 to 350 mOsm/kg. Isotonic agents used include, but are not limited to, polyols, saccharides and sucrose, amino acids, metal salts, for example, sodium chloride, etc.

"Stabilizer" refers to an excipient or a mixture of two or more excipients that provide the physical and/or chemical stability of the active agent. Stabilizers include amino acids, for example, but are not limited to, arginine, histidine, glycine, lysine, glutamine, proline; surfactants, for example, but are not limited to, polysorbate 20 (trade name: Tween 20), polysorbate 80 (trade name: Tween 80), polyethylene-polypropylene glycol and copolymers thereof (trade names: Poloxamer, Pluronic, sodium dodecyl sulfate (SDS); antioxidants, for example, but are not limited to, methionine, acetylcysteine, ascorbic acid, monothioglycerol, sulfurous acid salts, etc.; chelating agents, for example, but are not limited to, ethylenediaminetetraacetic acid (EDTA), diethylenetriaminepentaacetic acid (DTPA), sodium citrate, etc.

A pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition of the invention can be manufactured, packaged, or widely sold in the form of a single unit dose or a plurality of single unit doses in the form of a ready formulation. The term "single unit dose", as used herein, refers to discrete quantity of a pharmaceutical composition containing a predetermined quantity of an active ingredient. The quantity of the active ingredient typically equals the dose of the active ingredient to be administered in a subject, or a convenient portion of such dose, for example, half or a third of such dose.

Pharmaceutical compositions according to the present invention are typically suitable for parenteral administration as sterile formulations intended for administration in a human body through the breach in skin or mucosal barriers, bypassing the gastrointestinal tract by virtue of injection, infusion and implantation. For example, parenteral administration includes, inter alia, subcutaneous, intraperitoneal, intramuscular, intrasternal, intravenous, intraarterial, intrathecal, intraventricular, intraurethral, intracranial, intrasynovial, transdermal injection or infusions; and kidney dialytic infusion techniques. Intra-tumor delivery, for example, intra-tumor injection, can also be employed. Regional perfusion is also provided. Preferred embodiments include intravenous and subcutaneous routes. Any method for administering peptides or proteins, which is accepted in the art, may be suitably employed for a monoclonal antibody that specifically binds to CD20 according to the invention.

Injectable formulations may be prepared, packaged, or sold, without limitation, in unit dosage form, such as in ampoules, vials, in plastic containers, pre-filled syringes, autoinjection devices. Formulations for parenteral administration include, inter alia, suspensions, solutions, emulsions in oily or aqueous bases, pastes, and the like.

In another embodiment, the invention provides a composition for parenteral administration comprising a pharmaceutical composition which is provided in dry (i.e. powder or granular) form for reconstitution with a suitable base (e.g., sterile pyrogen-free water) prior to administration. Such formulation may be prepared by, for example, lyophilisation process, which is known in the art as freeze drying, and which involves freezing a product followed by removal of solvent from frozen material.

A monoclonal antibody that specifically binds to CD20 according to the invention can also be administered intranasally or by inhalation, either alone, as a mixture with a suitable pharmaceutically acceptable excipient from an inhaler, such as a pressurised aerosol container, pump, spray, atomiser, or nebuliser, wherein a suitable propellant is used or not used, or as nasal drops, or spray.

Dosage forms for parenteral administration may be formulated to be immediate or modified release. Modified release formulations include delayed-, sustained-, pulsed-, controlled-, targeted and programmed release.

Therapeutic Use of a Monoclonal Antibody that Specifically Binds to CD20 According to the Invention In one aspect, a monoclonal antibody that specifically binds to CD20 according to the invention is useful in the treatment of disorders that are associated with (mediated by) CD20 activity.

In one aspect, the subject is a mammal, preferably a human subject. Said subject may be either male or female, of any age.

In the case of a tumor (for example, cancer), the therapeutically effective amount of antibody or fragment thereof (for example, an antibody or fragment thereof that specifically binds to CD20) may reduce the number of cancer cells; reduce the initial tumor size; inhibit (i.e., slow to some extent and preferably stop) cancer cell infiltration into peripheral organs; inhibit (i.e., slow to some extent and preferably stop) tumor metastasis; inhibit to some extent tumor growth; and/or relieve to some extent one or more of the symptoms associated with the disorder. The antibody or fragment thereof may to some extent prevent growth and/or kill existing cancer cells, it may be cytostatic and/or cytotoxic. For cancer therapy, in vivo efficacy can, for example, be measured by assessing survival, time to tumor progression (TTP), tumor response rate to treatment (RR), duration of response and/or quality of life.

As used herein, the terms "co-administration", "co-administered" and "in combination with", referring to a monoclonal antibody that specifically binds to CD20 and one or more different therapeutic agents, are intended to mean, refer to or include the following:

1) simultaneous administration of such combination of a monoclonal antibody that specifically binds to CD20 according to the invention and therapeutic agent to a patient in need of treatment, when such components are formulated together into a single dosage form which releases said components at substantially the same time to said patient, 2) simultaneous administration of such combination of a monoclonal antibody that specifically binds to CD20 according to the invention and therapeutic agent to a patient in need of treatment, when such components are formulated apart from each other into separate dosage forms which are taken at substantially the same time by said patient, whereupon said components are released at substantially the same time to said patient, 3) sequential administration of such combination of a monoclonal antibody that specifically binds to CD20 according to the invention and therapeutic agent to a patient in need of treatment, when such components are formulated apart from each other into separate dosage forms which are taken at consecutive times by said patient with a significant time interval between each administration, whereupon said components are released at substantially different times to said patient; and 4) sequential administration of such combination of a monoclonal antibody that specifically binds to CD20 according to the invention and therapeutic agent to a patient in need of treatment, when such components are formulated together into a single dosage form which releases said components in a controlled manner, whereupon they are concurrently, consecutively, or jointly released at the same and/or different times to said patient, where each portion may be administered by either the same or different routes.

A monoclonal antibody that specifically binds to CD20 according to the invention can be administered without further therapeutic treatment, i.e., as an independent therapy. Furthermore, treatment by a monoclonal antibody that specifically binds to CD20 according to the invention may comprise at least one additional therapeutic treatment (combination therapy). In some embodiments, a monoclonal antibody that specifically binds to CD20 may be administered jointly or formulated with another medication/preparation for the treatment of a cancer or autoimmune disease.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiiylenethiophosphoramide and trimethylolomelamine; acetogenins (e.g., bullatacin and bullatacinone); delta-9-tetrahydrocannabinol (dronabinol MARINOL®); beta-lapachone; lapachol; colchicines; betulinic acid; camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (e.g., cryptophycin 1 and cryptophycin 8); dolastatin; duocarmycin (including the synthetic analogues, KW-2189 and CB1-TM1); eleutherobin; pancratistatin; sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, e.g., calicheamicin gamma II and calicheamicin omega II (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXOL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamideglycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (e.g., T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®), FILDESIN®), and vinorelbine (NAVELBINE®); etoposide (VP16); ifosfamide; mitoxantrone; leucovorin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN®); bisphosphonates such asclodronate (for example, BONEFOS® or OSTAC®), etidronate (DIDROCAL®), NE-58095, zoledronic acid/zoledronate (ZOMETA®), alendronate (FOSAMAJX®), pamidronate (AREDIA®), tiludronate (SKELID®), or risedronate (ACTONEL®); troxacitabine (1,3-dioxolane nucleoside cytosine analog); antisense oligonucleotides, particularly those that inhibit expression of genes in signaling pathways implicated in aberrant cell proliferation, such as for example, PKCalpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g., celecoxib or etoricoxib), proteosome inhibitor (e.g., PS341); bortezomib (VELCADE®); CCI-779; tipifarnib (Rl 1577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate or inhibit hormone action on tumors, such as anti-estrogens with mixed agonist/antagonist profile, including, tamoxifen (NOLVADEX®), 4-hydroxytamoxifen, toremifene (FARESTON®), idoxifene, droloxifene, raloxifene (EVTSTA®), trioxifene, keoxifene, and selective estrogen receptor modulators (SERMs), such as SERM3; pure anti-estrogens without agonist properties, such as fulvestrant) (FASLODEX®), and EM800 (such agents may block estrogen receptor (ER) dimerization, inhibit DNA binding, increase ER turnover, and/or suppress ER levels); aromatase inhibitors, including steroidal aromatase inhibitors, such as formestane and exemestane (AROMASIN®), and nonsteroidal aromatase inhibitors, such as anastrazole) (AREVIIDEX®), letrozole (FEMAPA®) and aminoglutethimide, and other aromatase inhibitors including vorozole (RIVISOR®), megestrol acetate) (MEGASE®), fadrozole, imidazole; lutenizing hormone-releasing hormone agonists, including leuprolide (LUPRON® and ELIGARD®), goserelin, buserelin, and tripterelin; sex steroids, including progestines, such as megestrol acetate and medroxyprogesterone acetate, estrogens, such as diethylstilbestrol and premarin, and androgens/retinoids such as fluoxymesterone, all transretionic acid and fenretinide; onapristone; anti-progesterones; estrogen receptor down-regulators (ERDs); anti-androgens, such as flutamide, nilutamide and bicalutamide; testolactone; and pharmaceutically acceptable salts, acids or derivatives of any of the above; as well as combinations of two or more of the above.

In treatment of the above autoimmune diseases or related autoimmune conditions, a monoclonal antibody that specifically binds to CD20 as provided herein in combination with a different therapeutic agent such as an immunosuppressor, anti-inflammatory drug, systemic hormone drug, antineoplastic and immunomodulatory drug or others may be administered in a patient, using a multidrug regimen. A monoclonal antibody that specifically binds to CD20 can be administered simultaneously, sequentially or alternately with a different therapeutic agent or after showing resistance to a different therapy. A different therapeutic agent may be administered in the same or lower dosages as compared to those used in the art. Many factors, including type of disease to be treated and patient's medical record, should be taken into account when choosing a preferred different therapeutic agent.

As used herein, the term "immunosuppressor" used in add-on therapy refers to substances directed to suppress or mask a patient's immune system. Such agents can be substances that inhibit cytokine production, down-regulate or suppress self-antigen expression or mask major histocompatibility complex (MHC) antigens. Examples of such agents include steroids, such as glucocorticoids, for example prednisone, methylprednisolone and dexamethasone; 2-amino-6-aryl-5-substituted pyrimidines (see U.S. Pat. No. 4,665,077), azathioprine (or cyclophosphamide, in case of adverse reaction to azathioprine); bromocryptine; glutaraldehyde (which masks MHC antigens, as described in U.S. Pat. No. 4,120,649); anti-idiotypic antibodies against MHC antigens and MHC fragments; cyclosporine A; cytokine and cytokine receptor antagonists including interferon-gamma, -beta, or -alpha antibodies; anti-tumor necrosis factor antibodies; anti-interleukine-2 antibodies and anti-IL-2 receptor antibodies; anti-L3T4 antibodies, heterologous anti-lymphocyte globulin, pan-T antibodies, preferably anti-CD3 or anti-CD4/CD4a antibodies; soluble peptide containing a LFA-3 binding domain (WO 90/08187, published Jun., 26, 1990); streptokinase; TGF-p; streptodomase; host DNA/RNA; FK506; RS-61443; deoxyspergualin; rapamycin; T cell receptor (U.S. Pat. No. 5,114,721); T cell receptor fragments (Offner et al, Science 251:430-432 (1991); WO 90/11294; and WO 91/01133); and T cell receptor antibodies (EP 340109), such as T10B9.

In treatment of rheumatoid arthritis, a patient may be administered a monoclonal antibody that specifically binds to CD20 according to the invention, alone or in combination with one or more of the following drugs: DMARDs (basic anti-inflammatory drugs (e.g. methotrexate, leflunomide, sulfasalazine), NSAIDs (nonsteroidal anti-inflammatory drugs, e.g. cyclooxygenase inhibitors), corticosteroids (e.g. prednisolone, budesonide). Typical DMARDs that are used in treatment of RA are hydroxychloroquine, sulfasalazine, methotrexate, leflunomide, azathioprine, D-penicillamine, gold-based preparations (oral), gold-based preparations (intramuscular), minocycline, cyclosporine, Staphylococcal obtained by protein A immunoadsorption. Conventional methods for treatment of RA are described, for example, in J. A. Singh et al., 2015 American College of Rheumatology Guideline for the Treatment of Rheumatoid Arthritis. Arthritis Care Res (Hoboken) 68, 1-25 (2016).

It is meant that a monoclonal antibody that specifically binds to CD20 according the invention may be used in the methods of treatment as described above, may be used in the treatment as described above, and/or may be used in the manufacture of a medication for treatment as described above.

Doses and Routes of Administration

A monoclonal antibody that specifically binds to CD20 according to the invention will be administered in an amount that is effective in treatment of the condition in question, i.e. in doses and during the periods of time required to achieve the desired result. A therapeutically effective amount may vary according to factors such as the particular condition being treated, the age, sex and weight of the patient, and whether the monoclonal antibody that specifically binds to CD20 is being administered as a stand-alone treatment or in combination with one or more additional drugs or treatments.

Dosage regimens may be adjusted to provide the optimum response. For example, a single bolus may be administered, several divided doses may be administered over time or the dose may be proportionally reduced or increased as indicated by the exigencies of the therapeutic situation. It is especially advantageous to formulate parenteral compositions in a unit dosage form for ease of administration and uniformity of dosage. A unit dosage form as used herein is intended to refer to physically discrete units suited as unitary dosages for patients/subjects to be treated; each unit contains a predetermined quantity of active compound calculated to produce the desired therapeutic effect in association with the desired pharmaceutical carrier. Specification for the unit dosage forms of the invention is typically dictated by and directly dependent on (a) the unique characteristics of a chemotherapeutic agent and particular therapeutic or prophylactic effect to be achieved, and (b) the limitations inherent in the art of compounding such an active compound for the treatment of sensitivity in the subjects.

Thus, a skilled artisan would appreciate, based upon the disclosure provided herein, that the doses and dosage regimen are adjusted in accordance with methods well-known in the therapeutic arts. That is, the maximum tolerable dose can be readily established, and the effective amount providing a detectable therapeutic effect to a patient may also be determined, as can the temporal requirements for administering each agent to provide a detectable therapeutic effect to a patient. Thus, while certain dose and administration regimens are exemplified herein, these examples in no way limit the doses and administration regimen that may be provided to a patient in practicing the embodiments of the invention.

It is to be noted that dosage values may vary with the type and severity of the condition to be alleviated, and may include single or multiple doses. Furthermore, it is to be understood that for any particular subject, specific dosage regimens should be adjusted over time according to the individual need and the judgment of a medical professional administering or supervising the administration of the compositions, and that dosage ranges set forth herein are exemplary only and are not intended to limit the scope or practice of the claimed compositions. Further, the dosage regimen with the compositions of this invention may be based on a variety of factors, including the type of disease, the age, weight, sex, medical condition of the patient, the severity of the condition, the route of administration, and the particular monoclonal antibody that specifically binds to CD20 employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the person skilled in the art. Methods for determining appropriate dosages and regimens are well-known in the art and would be understood by a skilled artisan once provided the ideas disclosed herein.

Examples of suitable administration methods are provided above.

It is believed that a suitable dose of a monoclonal antibody that specifically binds to CD20 according to the invention will be in the range of 0.1-200 mg/kg, preferably 0.1-100 mg/kg, including about 0.5-50 mg/kg, for example about 1-20 mg/kg. The monoclonal antibody that specifically binds to CD20 may be administered, e.g. in a dose of at least 0.25 mg/kg, such as at least 0.5 mg/kg, including at least 1 mg/kg, e.g., at least 1.5 mg/kg, such as at least 2 mg/kg, e.g., at least 3 mg/kg, including at least 4 mg/kg, e.g., at least 5 mg/kg; and for example up to a maximum of 50 mg/kg, including up to a maximum of 30 mg/kg, e.g., up to a maximum of 20 mg/kg, including up to a maximum of 15 mg/kg. The administration will typically be repeated in appropriate time intervals, such as once a week, once every two weeks, once every three weeks or once every four weeks, and for as long as deemed appropriate by a responsible physician, who may, in some cases, increase or reduce the dose if necessary.

Diagnostic Use and Compositions

A monoclonal antibody that specifically binds to CD20 according to the invention is also used in diagnostic processes (e.g., in vitro, ex vivo). For example, the present monoclonal antibody that specifically binds to CD20 according to the invention can be used for detecting or measuring the level of CD20 in samples obtained from a patient (e.g., tissue sample or a sample of body fluid, such as an inflammatory exudate, blood, serum, intestinal fluid, saliva or urine). Suitable methods for detection and measurement include immunoassays, such as flow cytometry, enzyme-linked immunosorbent assay (ELISA), chemiluminescent assay, radioimmunoassay, and immunohistology. The invention further includes kits, for example, diagnostic kits comprising a monoclonal antibody that specifically binds to CD20 described herein.

The following examples are provided for better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

EXAMPLES

The following examples are provided for better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

Materials and General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to EU numbering (Edelman, G. M., et al., Proc. Natl. Acad. Sci. Natl. Acad. Sci. USA 63 (1969) 78-85; Kabat, E. A., et al., Sequences of Proteins of Immunological Interest, 5th ed., Public Health Service, National Institutes of Health, Bethesda, MD, (1991).

Recombinant DNA Techniques

Standard methods were used to manipulate DNA as described in Sambrook, J. et al, Molecular cloning: A laboratory manual; Cold Spring Harbor Laboratory Press, Cold Spring Harbor, New York, 1989. The molecular biological reagents were used according to the manufacturer's instructions.

Gene Synthesis

Desired gene segments were prepared from oligonucleotides made by chemical synthesis. The gene segments of 300-4000 kb long, which were flanked by singular restriction sites, were assembled by annealing and ligation of oligonucleotides including PCR amplification and subsequently cloned via the indicated restriction sites. The DNA sequences of the subcloned gene fragments were confirmed by DNA sequencing.

DNA Sequence Determination

DNA sequences were determined by Sanger sequencing.

DNA and Protein Sequence Analysis and Sequence Data Management

The Infomax's Vector NT1 Advance suite version 8.0 was used for sequence creation, mapping, analysis, annotation and illustration.

Expression Vectors

For the expression of the described antibodies and antigens, variants of expression plasmids intended for expression in prokaryotic cells (*E. coli*), transient expression in eukaryotic cells (e.g., in CHO cells) were applied. Beside the antibody expression cassette the vectors contained: an origin of replication which allows replication of said plasmid in *E. coli*, genes which confer resistance in *E. coli* to various antibiotics (e.g., to ampicillin and kanamycin).

The fusion genes comprising the described antibody chains as described below were generated by PCR and/or gene synthesis and assembled with known recombinant methods and techniques by connection of the according nucleic acid segments, e.g., using unique restriction sites in the corresponding vectors. The subcloned nucleic acid sequences were verified by DNA sequencing. For transient transfections, larger quantities of the plasmids were prepared by plasmid preparation from transformed *E. coli* cultures.

Example 1. Production of Recombinant Control Antibodies in Suspension Culture of Mammalian Cells Rituximab, an antibody with published sequence, was used as a control. The genes of heavy/light chain variable domains of antibody were synthesized and cloned into SalI/NheI and SalI/BstWI restriction sites of vectors pEE-HC, pEE-CK, respectively (FIGS. 1, 2), that are intended for production of protein in mammalian cells.

The required quantities of plasmids were cultured in *E. coli* cells and purified using Qiagen kit.

Control antibodies were produced in established cell line cells obtained from Chinese hamster ovary cells (CHO-T line). Suspension culture was conducted in flasks on orbital incubator shaker using serum-free media (HyCell TransFx-C) supplemented with 8 mM L-glutamine and 1 g/l of pluronic 68. For transient expression, cells (2-2, $2 \times 10^6$ cells/ml) were transfected by means of linear polyethyleneimine (PEI MAX, Polysciences). DNA/PEI ratio was 1:3-1:10. In 9 days after transfection, culture liquid was separated from cells by filtration through a 0.5/0.22 μm deep-bed filter. Target proteins were isolated from culture liquid by affine HPLC with Protein A, a bacterial protein.

The purity of protein solution obtained was evaluated by reducing and non-reducing SDS gel electrophoresis.

Example 2. Construction of a Naive Human Antibody FAB-Library MeganLib™

Total RNA of B lymphocytes from blood samples from more than one thousand individual human donors was isolated using RNeasy Mini Kit according to the suggested protocol (QIAGEN). RNA concentration assay was performed using Nanovue kit (GE Healthcare), the quality of isolated RNA was examined by means of 1.5% agarose gel electrophoresis.

Reverse transcription reaction was conducted using MMLV RT kit (Evrogen) according to the recommended protocol with MMuLV reverse transcriptase and random hexamer oligonucleotides as primers.

Reverse transcription products were used as a matrix in a two-stage polymerase chain reaction to produce the genes of variable domains flanked with restriction sites; reaction was performed using oligonucleotide kit according to protocols by [J Biol Chem. 1999 Jun. 25; 274(26): 18218-30].

Figure 4:
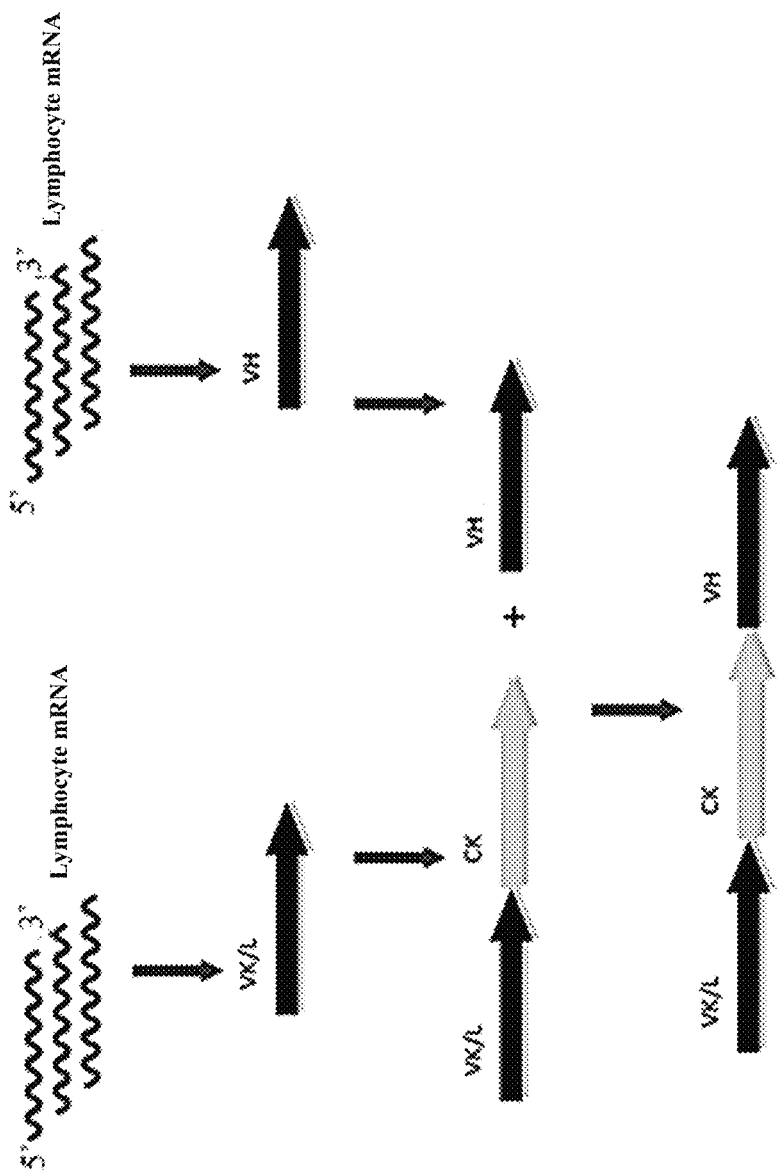
FIG. 4. Scheme of synthesis of a human naive combinatorial library.
Figure 5:
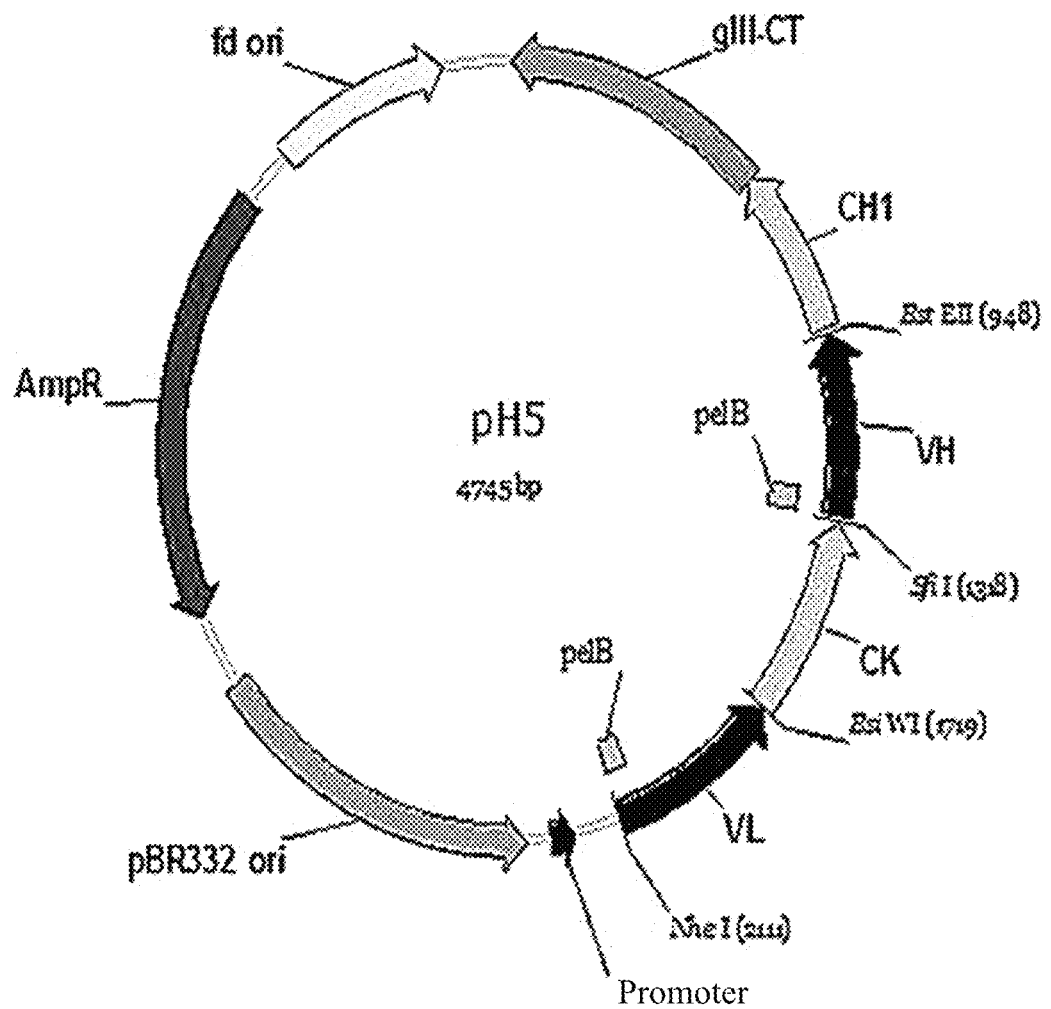
FIG. 5. Map of phagemid for cloning of Fab phage display libraries.

The resulting DNA preparation VL-CK-VH (FIG. 4) was treated with NheI/Eco91I restriction endonucleases and ligated into the original phagemid pH5 (FIG. 5). Ligation products were transformed into SS320 electrocompetent cells prepared in accordance with protocols [Methods Enzymol. 2000; 328: 333-63.]. Repertoire of combinatorial phage Fab display library MeganLib™ was 1011 transformants. Fab library phage products were prepared in accordance with the earlier described procedure [J Mol Biol. 1991 Dec. 5; 222(3): 581-97].

Example 3. Selection of FAB-Library by Phage Display

Specific anti-CD20 human phage Fab antibodies were obtained from the combinatorial phage Fab display library MeganLib™. Biopanning was performed on human CD20-expressing eukaryotic cells by phage display [Nat Biotechnol. 1996 March; 14(3):309-14; J Mol Biol. 1991 Dec. 5; 222(3): 581-97], but using magnetic beads and KingFisher Flex device, because this technique allows to perform up to 96 different biopanning schemes and variants simultaneously.

During biopanning, biotinylated eukaryotic cells were immobilized on the surface of streptavidin magnetic beads by incubating the cells with beads for 20 minutes on a rotator. The beads were then washed with PBS (pH 7.4), beads were then blocked with a solution of 2% fat-free milk in PBS (pH 7.4) for 1 hour. Then, a solution of phages that were preincubated with antigen-negative cells in PBS (pH 7.4) supplemented with 2% skim milk was added to the magnetic beads with bound cells. The mixture was incubated for 40 min under stirring. Unbound phages were removed by several cycles of washing of magnetic beads with a solution of PBS (pH 7.4) supplemented with 0.1% Tween-20. Number of washing cycles was increased from round to round (10 washing cycles in a first round, 30 washing cycles in second and third rounds). Phages that bound to antigen on the surface of magnetic beads were eluted from beads with 100 mM Gly-HCl solution (pH 2.2) for 15 min under stirring, and then the solution was neutralized with 1M Tris-HCl (pH 7.6). *E. coli* TG1 bacteria were infected with the resulting phages, the phages were cultured in the bacteria, isolated and used in the next cycle of selection. After three-four rounds, DNA (phagemids) were isolated from the phages, and antibody variable domain genes were cloned into expression vectors (FIG. 6) for production of Fabs in *E. coli* cells.

Example 4. Library Screening

Initial Screening

Fabs were produced according to the standard technique: bacterial cells were transformed with expression vectors containing Fab genes, whereas the subsequent addition of inducer, which triggers transcription of lac operon, into the medium during culturing of the resulting transformants induces expression of Fabs.

We then conducted ELISA for binding of Fab to substrate-immobilized CD20 peptide. Antigen-bound Fabs were detected using anti-human Fab HRP-conjugated secondary antibody (Pierce-ThermoScientific).

Figure 6:
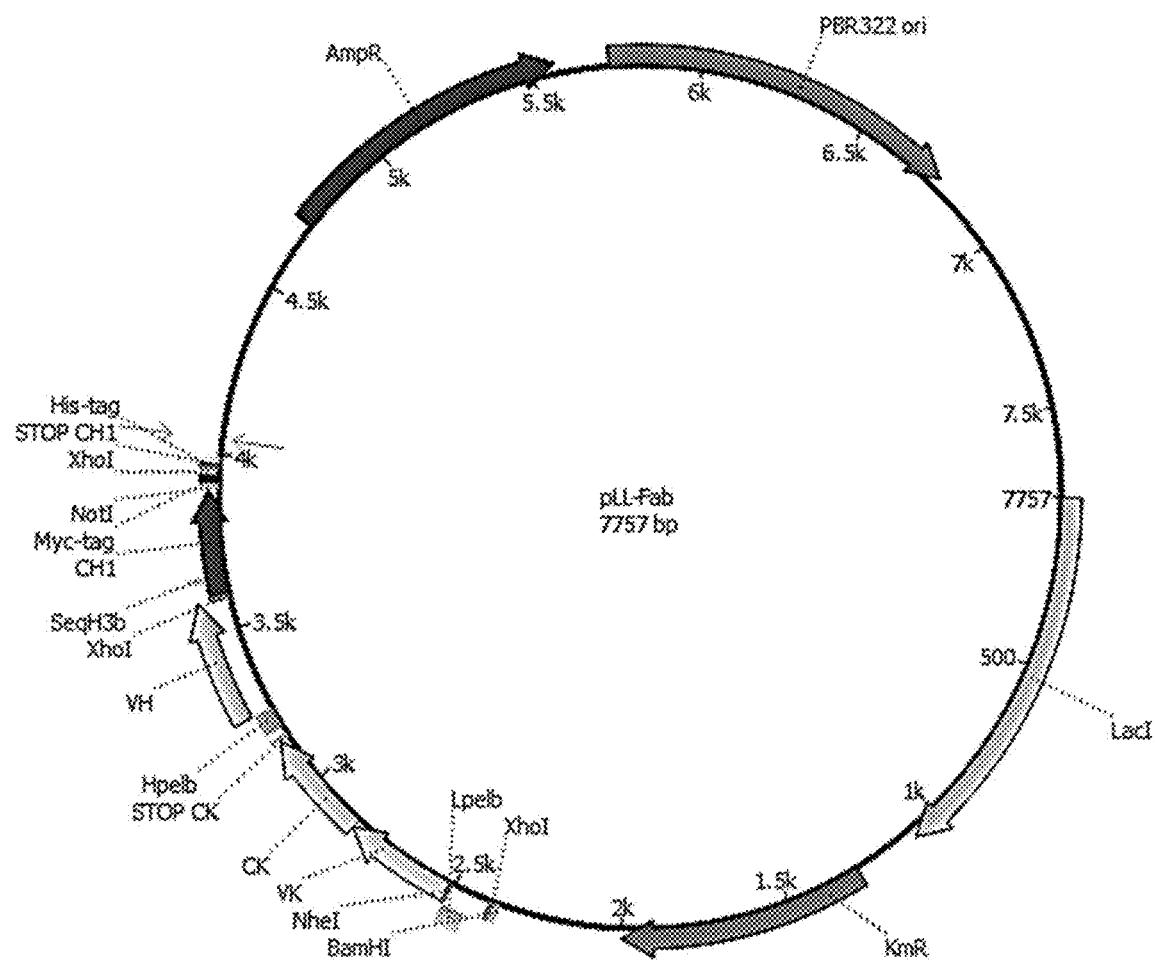
FIG. 6. Map of expression plasmid pLL for culturing of Fabs.

Rituximab Fab sequence inserted into the expression plasmid pLL was used as a positive control (FIG. 6).

As a result of initial screening, we selected clones that are capable of binding to target CD20 peptide. The material was transfered for secondary screening.

Secondary Screening

Secondary screening aimed at selection of Fab-producing clones which interact with CD20 peptide and do not interact with other antigens IL6R-Fc, PCSK9-VG-FE, PD-1-Fc.

Fabs were produced according to the standard technique. We then conducted ELISA for binding of Fabs to various substrate-immobilized antigens according to standard procedure.

As a result of secondary screening, Fab-producing clones that specifically bind only the target CD20 peptide were selected.

Example 5. Optimization of Leader Candidates

Selected candidates were optimized to increase humanization. Substitution points were selected using Humanizer tool from YLab software package (developed by Biocad). Germline Functional V, D, J segments from various biological species were obtained from the IMGT database and used as a data source. Human segments were used as positive references, whereas those from rats and mice were used as negative ones. Based on this data, the tool suggested positions to be substituted.

For further selection, we generated 1000 candidates with a plurality of subsets of the selected set of substitutions. The resulting candidates were modeled on the basis of crystal structure of initial candidate-target CD20 complex. Models were generated using BENDER (developed by Biocad) and BioLuminate (from Schrodinger Suite software, developed by Schrodinger) software. The resulting models were evaluated by calculating the average value MM-GBSA using OPLS 2005 force field along 100 ns molecular dynamics trajectories. Molecular dynamics trajectories were obtained using Desmond (Schrodinger Suite, developed by Schrodinger). In the obtained results, we clearly distinguished a cluster of 133 candidates, which were suggested for further synthesis, along with the control candidate.

Example 6. Preparation of Full-Length Antibodies in IgG1 Format

Figure 1:
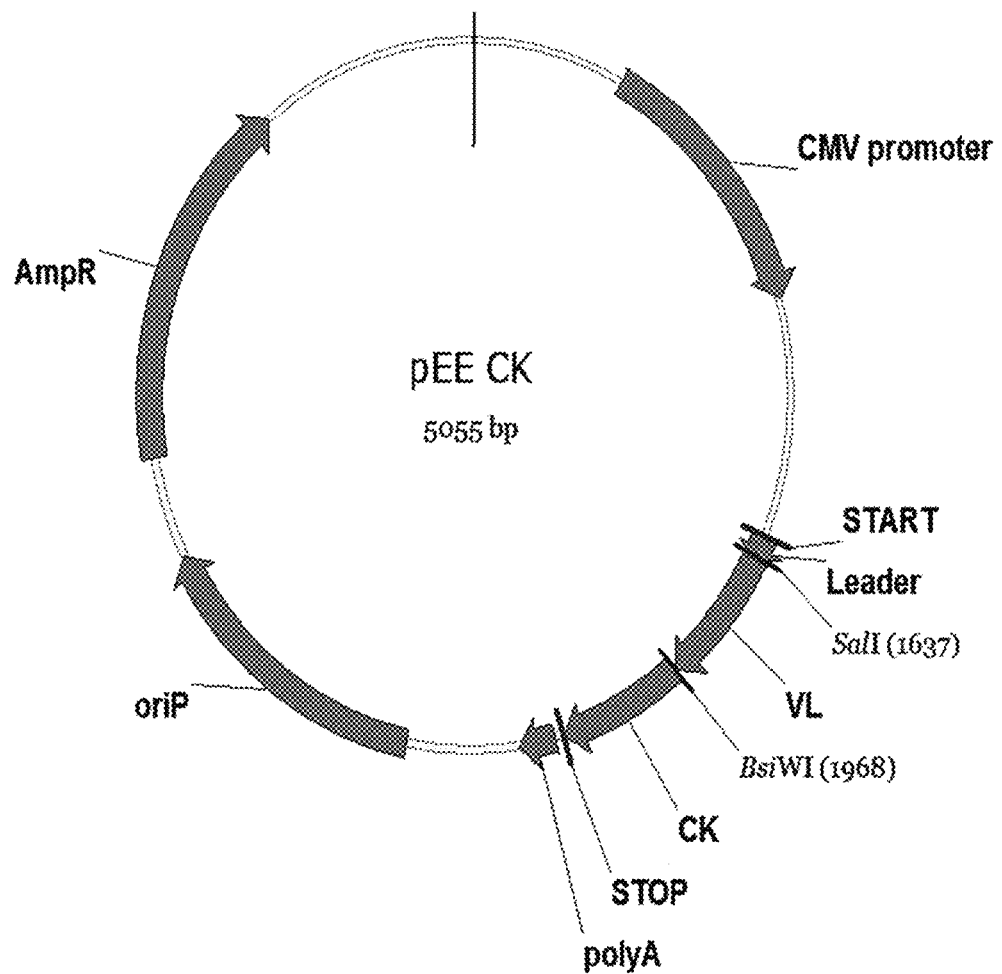
FIG. 1. Map of expression vector pEE CK.
Figure 2:
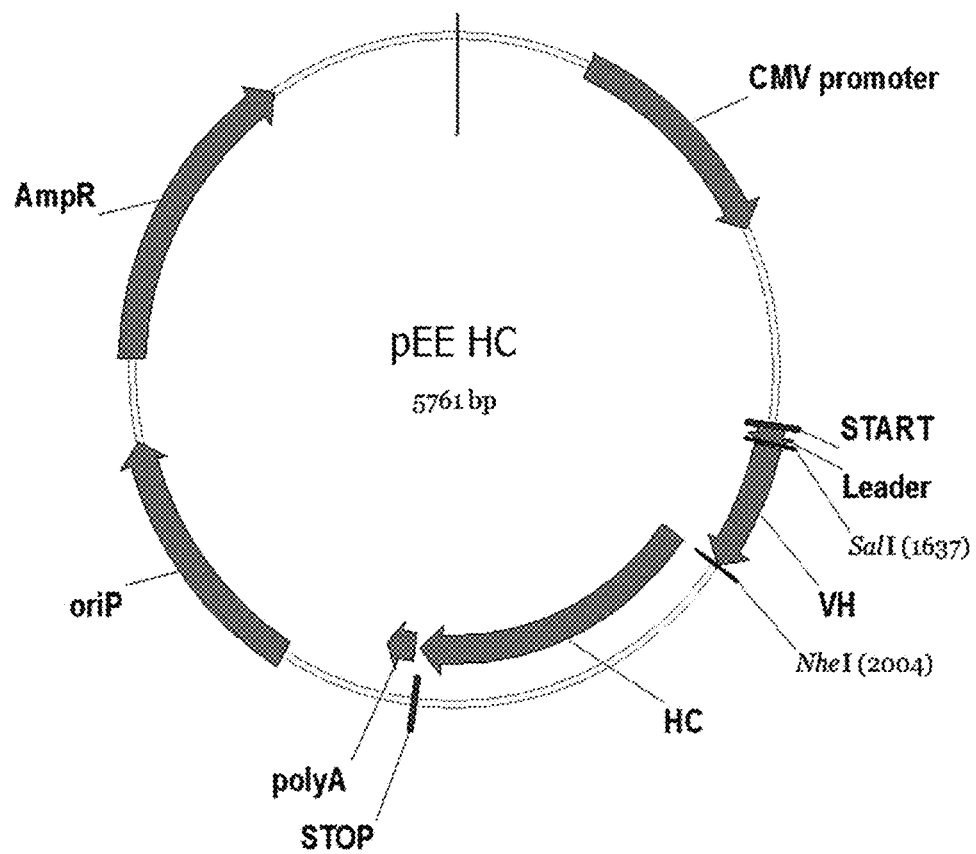
FIG. 2. Map of expression vector pEE HC.
Figure 3:
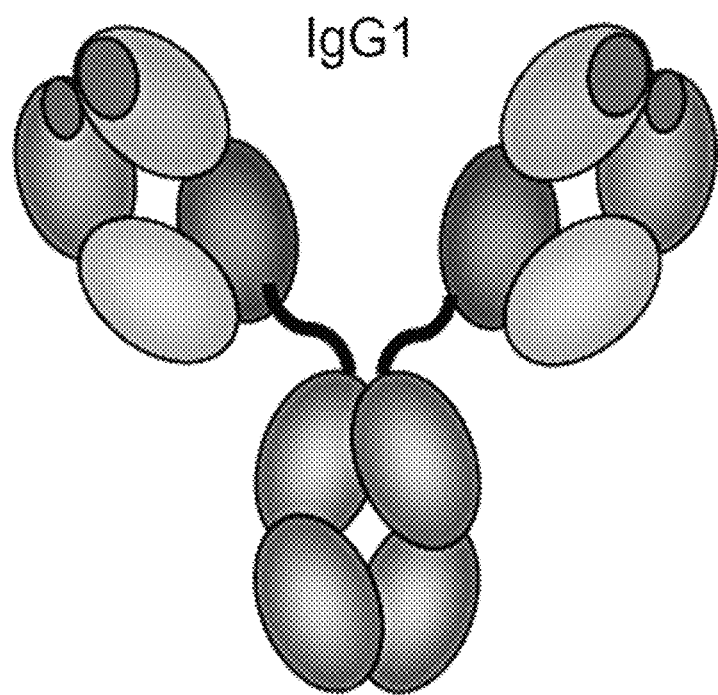
FIG. 3. Schematic diagram of IgG1 format.

CHO cells were codon optimized for the prepared 133 candidates using OligoDesigner tool from Ylab software package (BIOCAD). The optimized sequences of heavy/light chain variable domains were synthesized de novo and cloned into vectors pEE-HC, pEE-CK (IgG1 format) at Sal1/Nhe1 and Sal1/BsiW1 restriction sites, respectively (FIG. 1, 2). The schematic representation of the IgG1 format is given in FIG. 3.

The resulting genetic constructs were used to transform CHO-T cell line. Proteins were isolated and purified according to standard methods by affinity chromatography on bacterial Protein A as described in Example 1. Electrophoresis was performed in denaturing 7.5% PAGE. The production performance of 22 candidates was below the threshold level (50 mg/l); therefore, they were not isolated and purified.

Example 7. Sequencing of High Affinity Clones

Variable domain genes of positive clones were sequenced according to standard protocols on Applied Biosystems 3130 Genetic Analyzer (Applied Biosystems) and analyzed.

Example 8. Determination of Affinity of Full-Length Antibodies on Forte Bio Octert RED 384

KD values of the resulting full-length candidates were determined on Forte Bio Octet RED 384.

SAX biosensors and biotin-modified CD20 peptide (Sigma Aldrich) were used for the study. Antibody Rituximab was used as a control. SAX biosensors were steeped into a solution containing biotinylated CD20 peptide at a concentration of 20 µg/ml, where the peptide was immobilized. Further analysis was conducted at 30° C. using PBS containing 0.1% Tween 20 and 0.1% BSA as a working buffer.

After baseline recording in buffer solution, the sensors were immersed into wells containing antibody solution at a concentration of 10 µg/ml for 150 seconds, where the complex was associated. Complex dissociation in buffer solution was then detected for 300 seconds.

Binding curves, after subtracting a reference signal, were analyzed using Octet Data Analysis software (Version 9.0) in accordance with the standard procedure using 1:1 interaction model.

Figure 7:
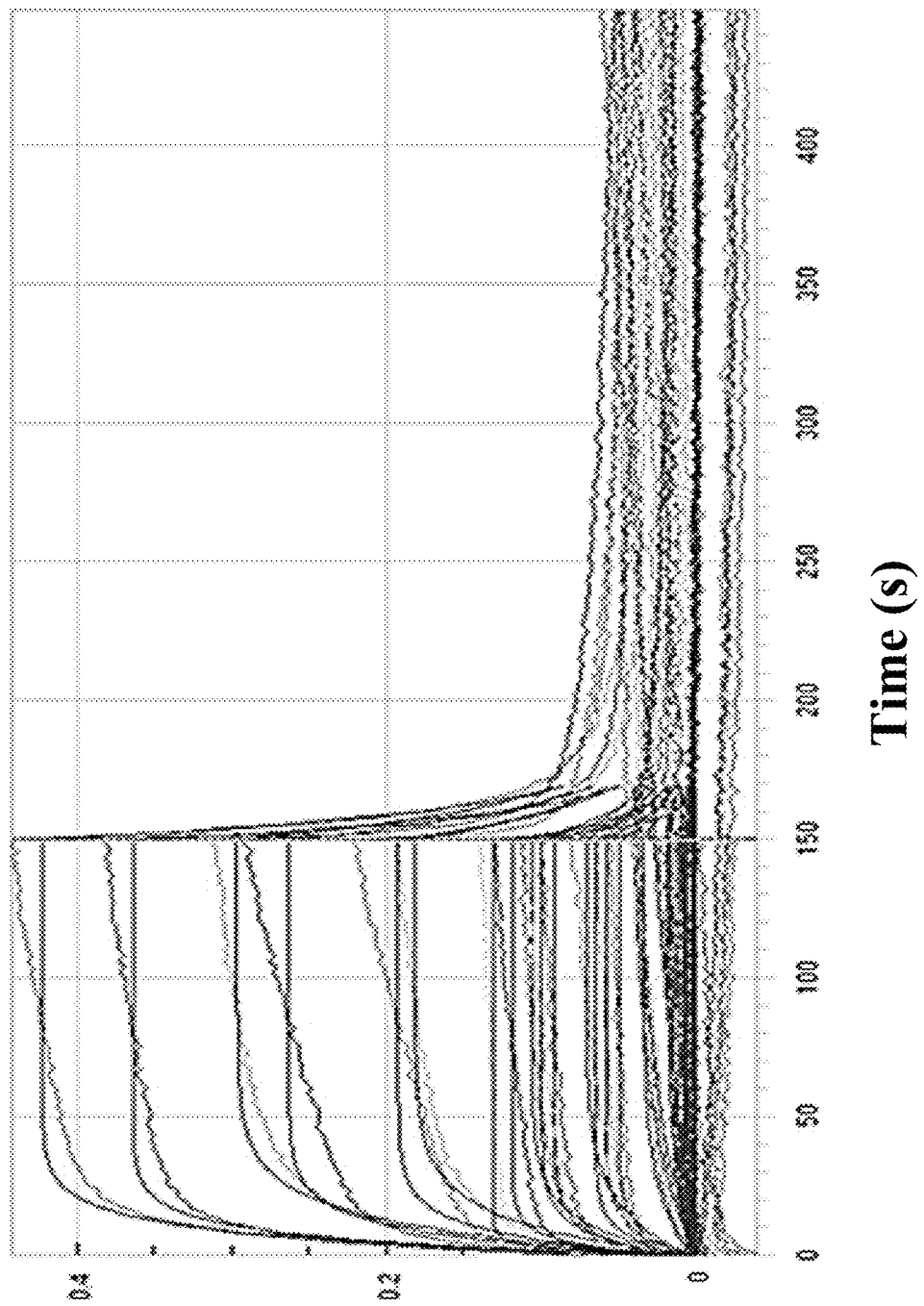
FIG. 7. Analysis of BCD132L candidate-biotinylated CD20 peptide interactions on Forte Bio Octet RED 386.
Figure 8:
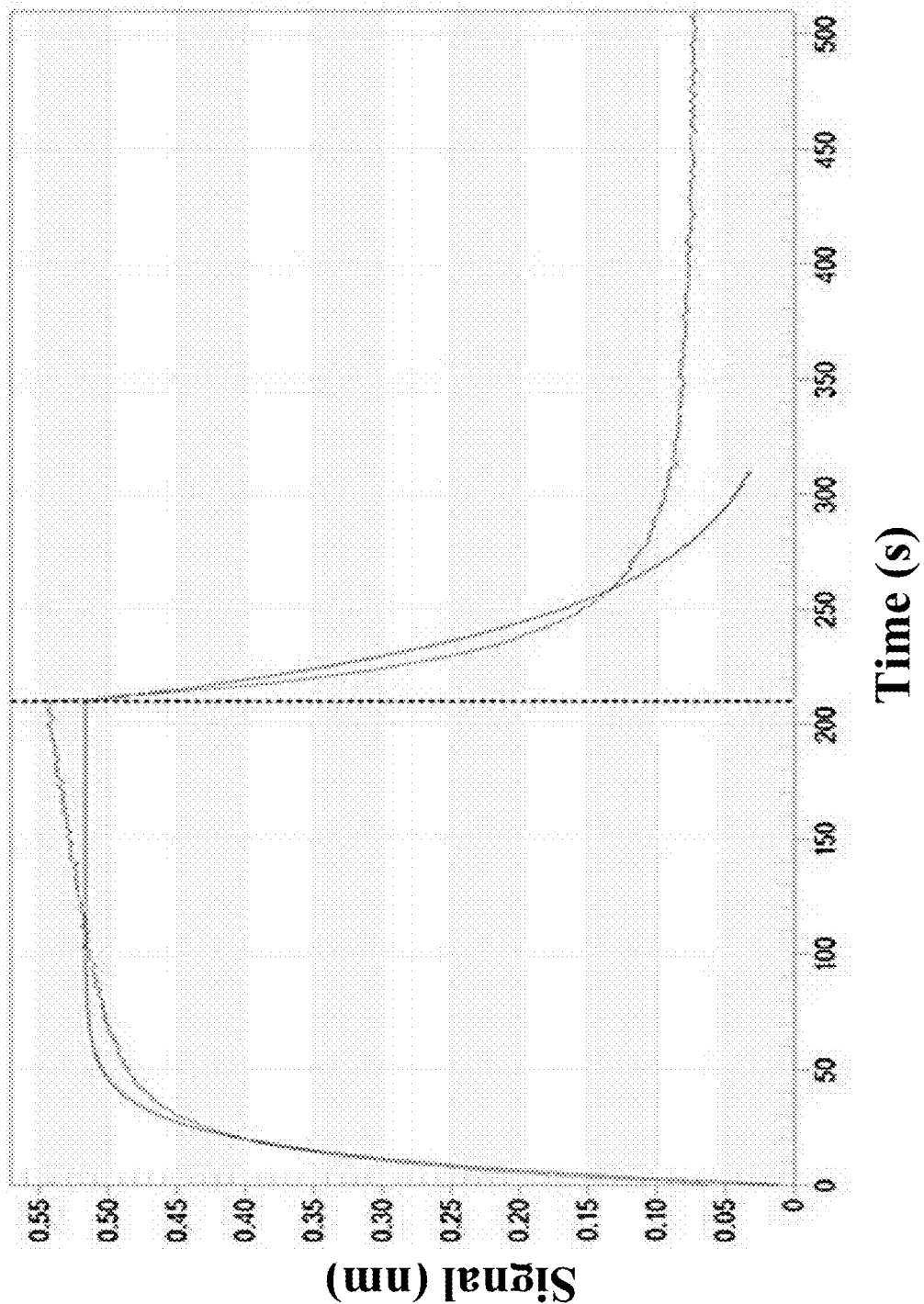
FIG. 8. Analysis of BCD132L-026 candidate-biotinylated CD20 peptide interactions on Forte Bio Octet RED 386.
Figure 9:
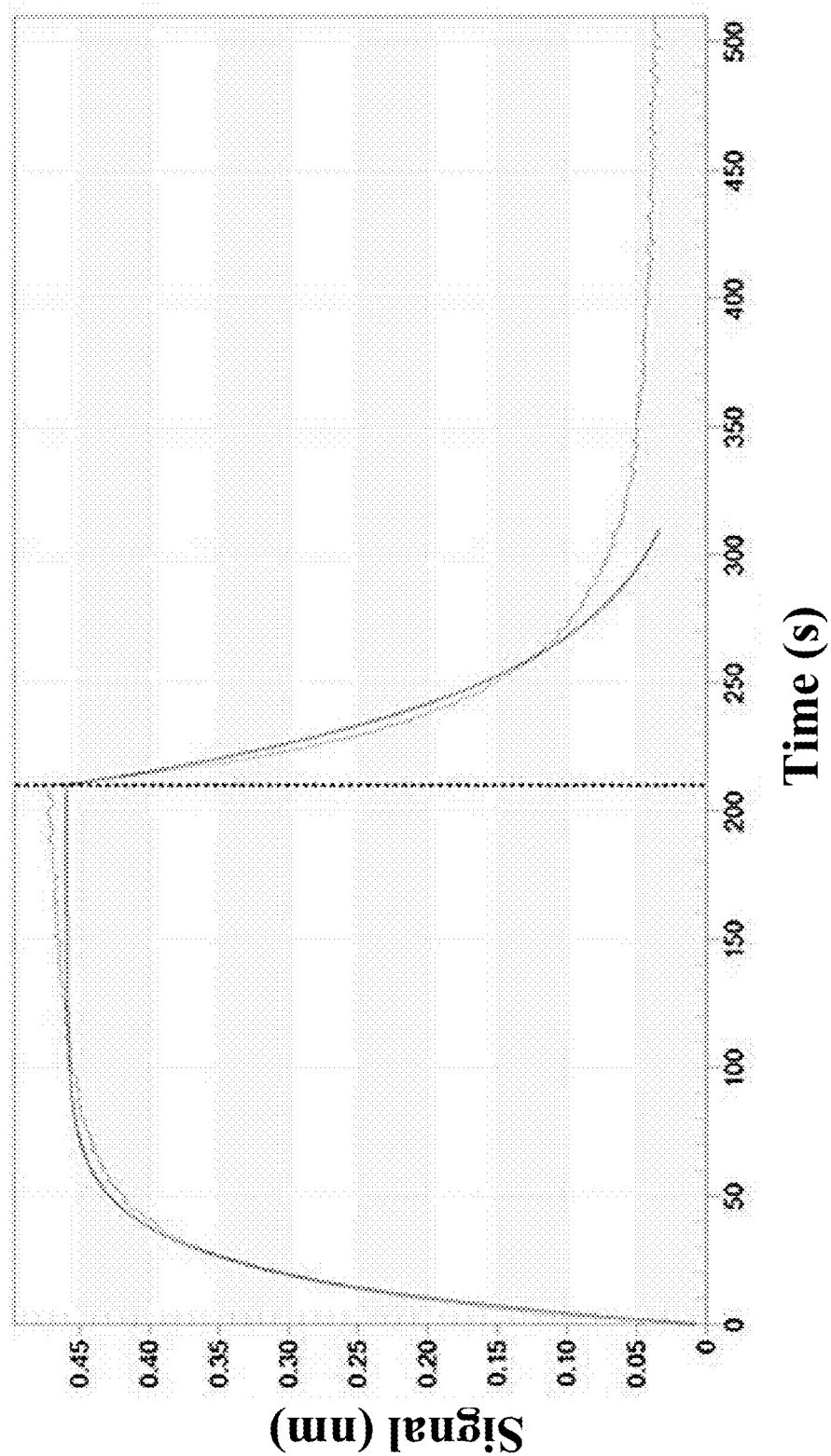
FIG. 9. Analysis of BCD132L-028 candidate-biotinylated CD20 peptide interactions on Forte Bio Octet RED 386.
Figure 10:
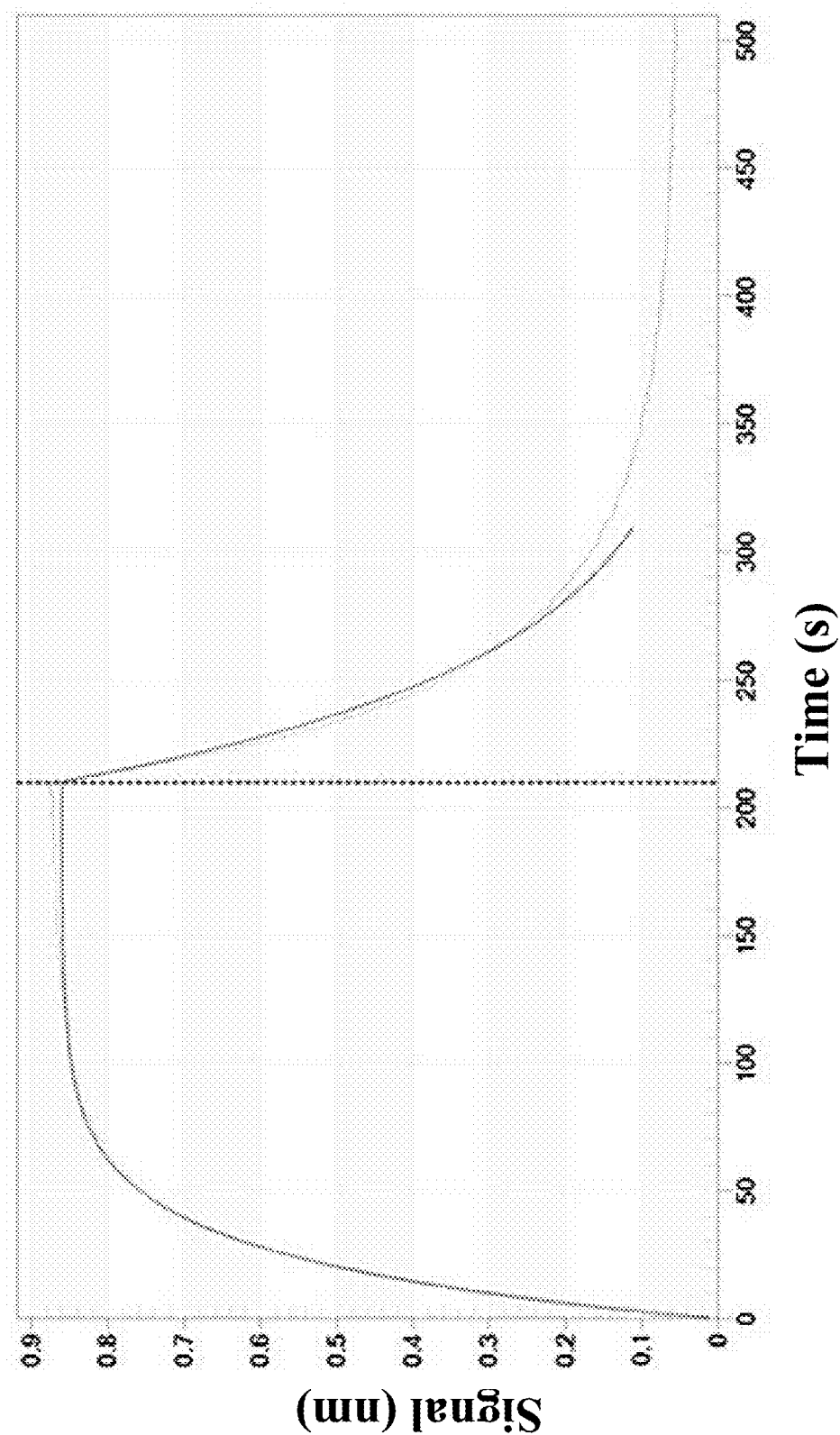
FIG. 10. Analysis of BCD132L-075 candidate-biotinylated CD20 peptide interactions on Forte Bio Octet RED 386.
Figure 11:
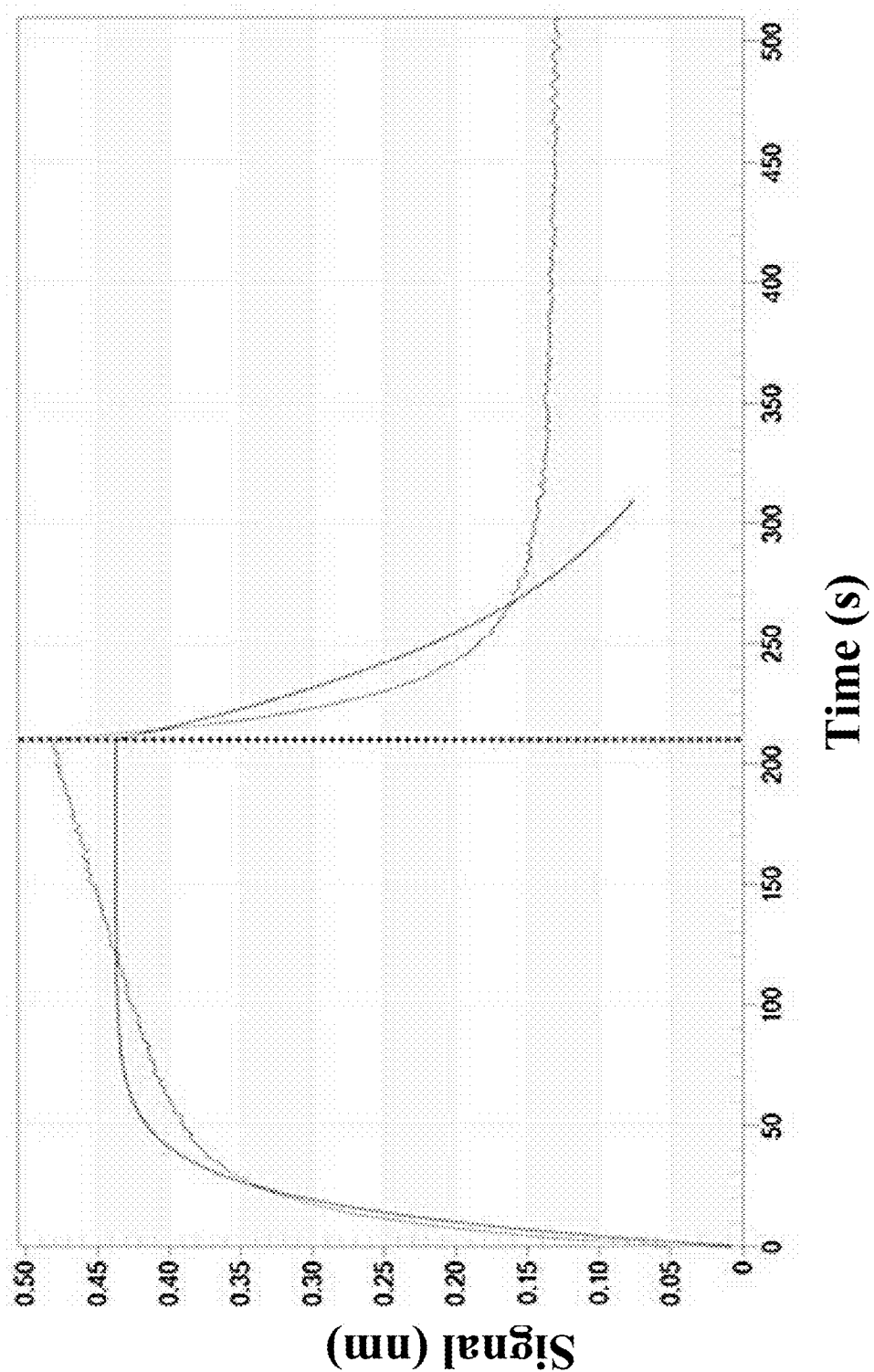
FIG. 11. Analysis of BCD132L-077 candidate-biotinylated CD20 peptide interactions on Forte Bio Octet RED 386.
Figure 12:
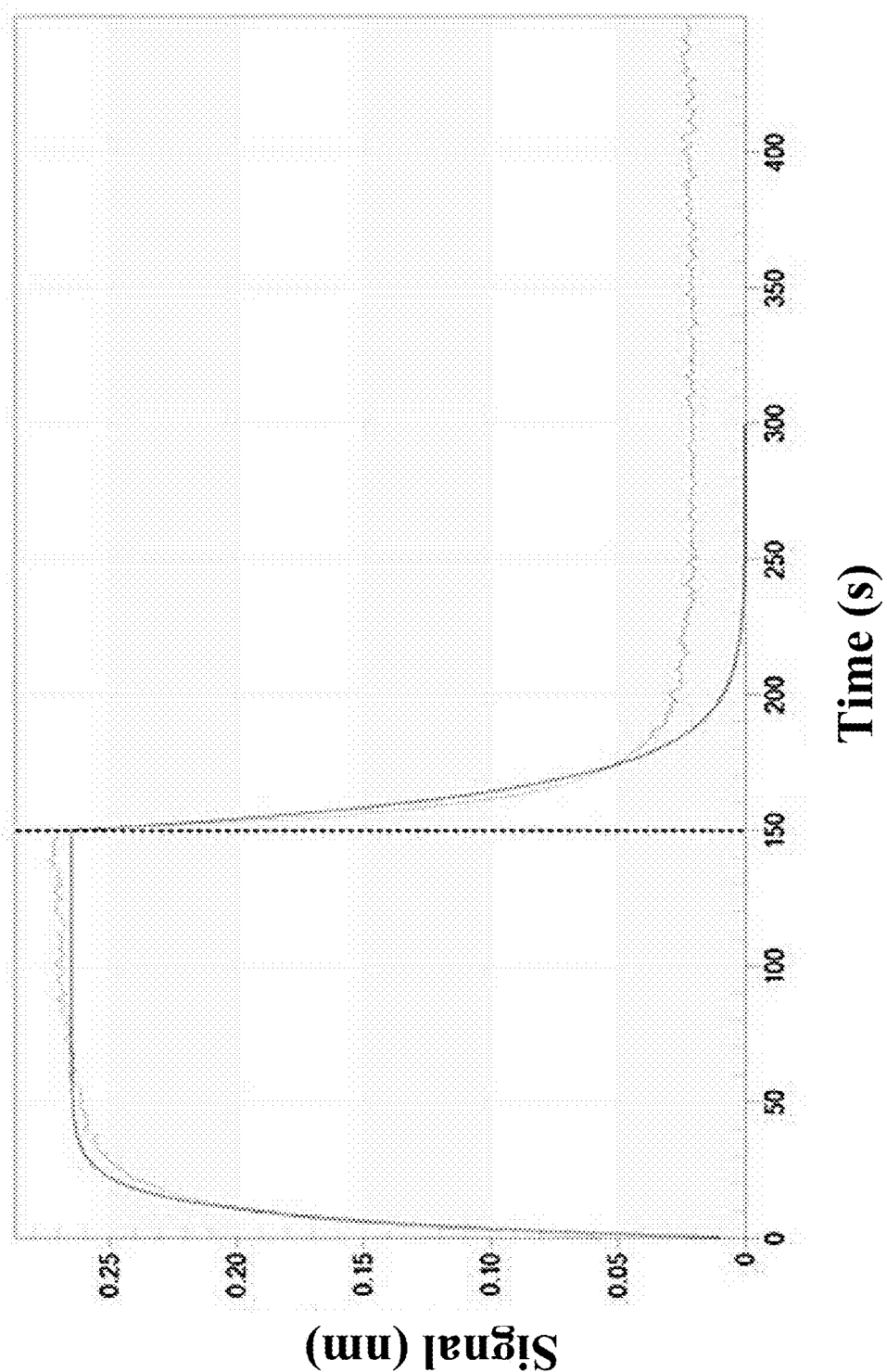
FIG. 12. Analysis of BCD132L-028 candidate-biotinylated CD20 peptide interactions on Forte Bio Octet RED 386.
Figure 13:
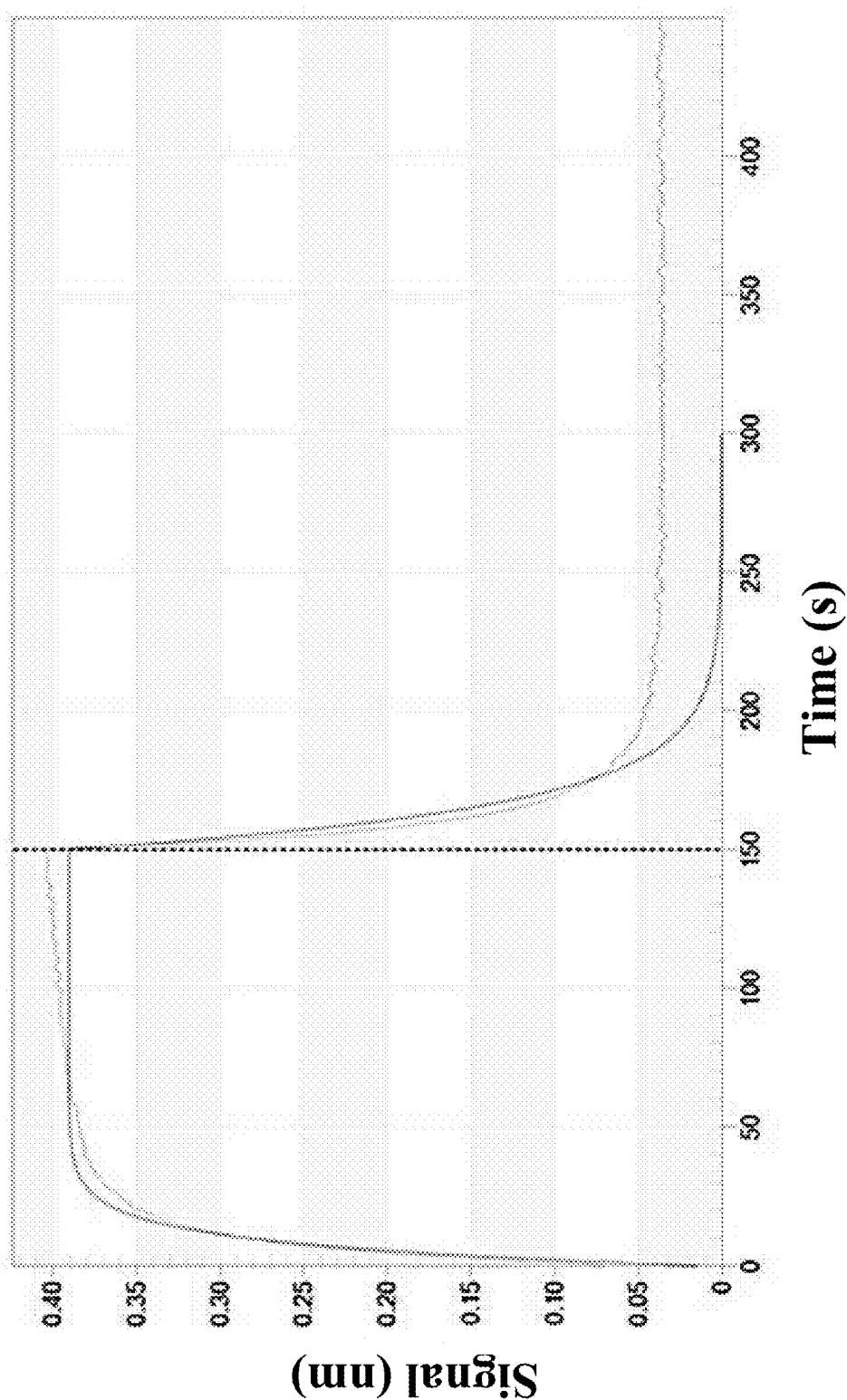
FIG. 13. Analysis of BCD132L-077 (1,2) candidate-biotinylated CD20 peptide interactions on Forte Bio Octet RED 386.
Figure 14:
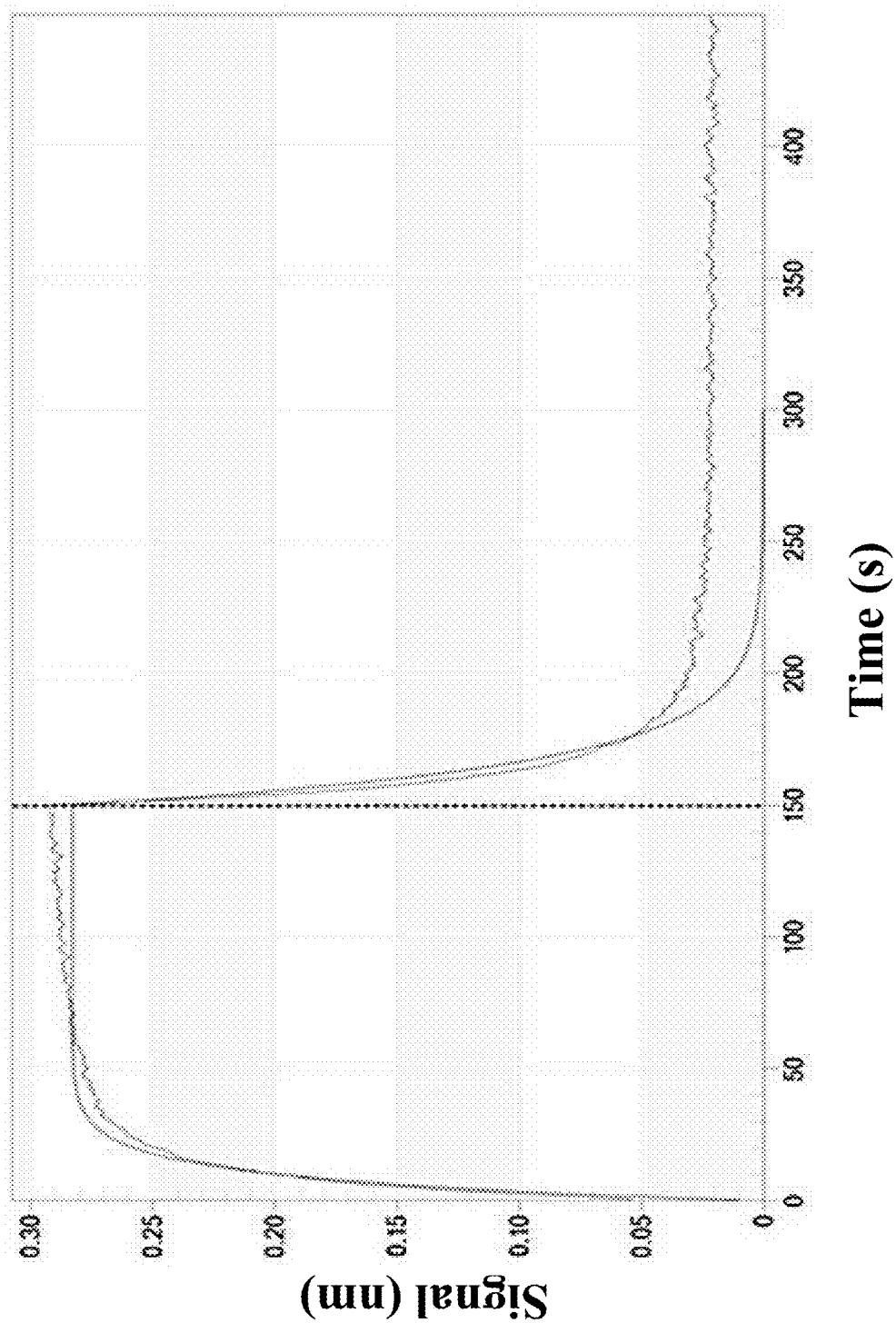
FIG. 14. Analysis of BCD132L-077 (3,4) candidate-biotinylated CD20 peptide interactions on Forte Bio Octet RED 386.
Figure 15:
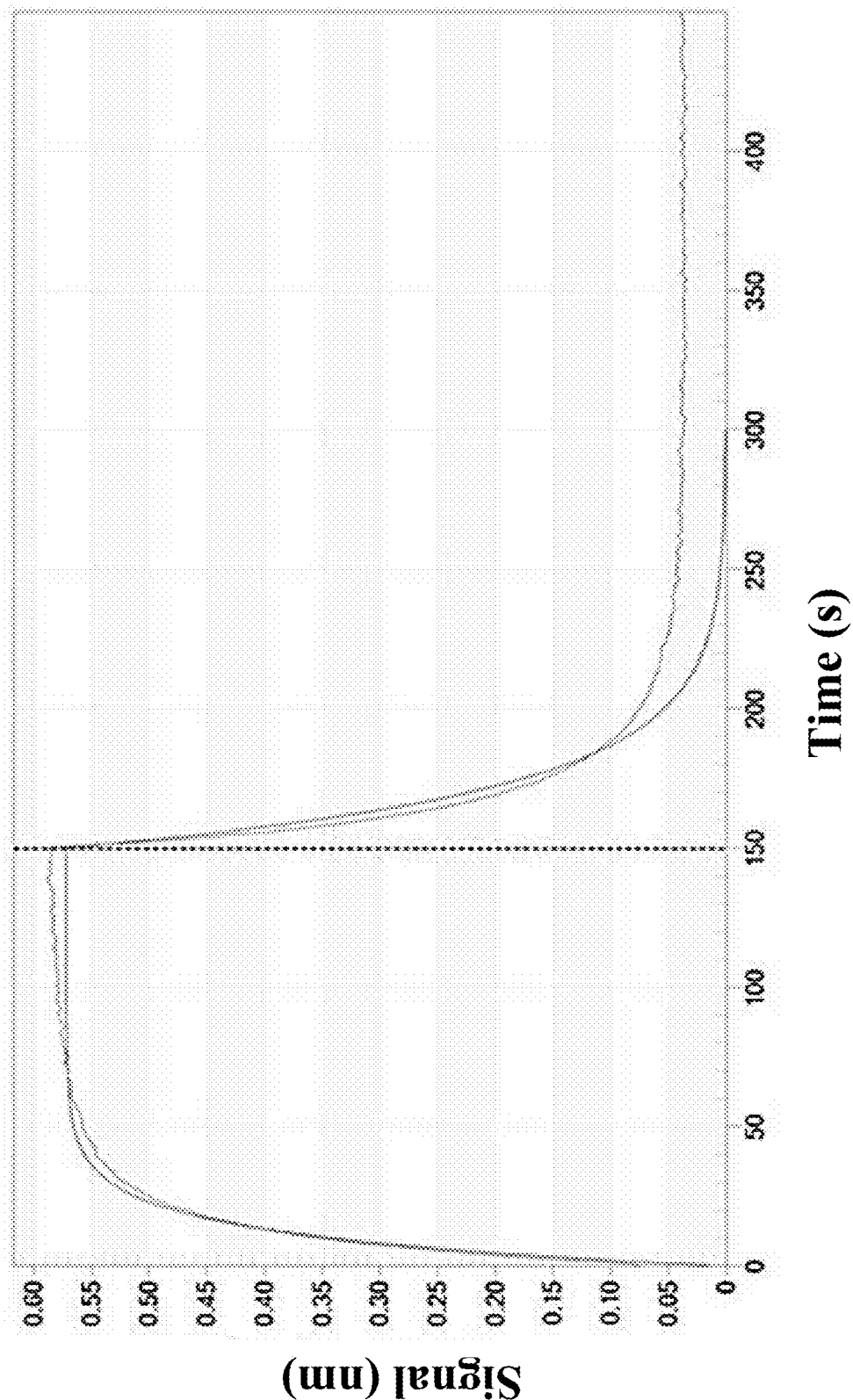
FIG. 15. Analysis of BCD132L-077 (5,6) candidate-biotinylated CD20 peptide interactions on Forte Bio Octet RED 386.
Figure 16:
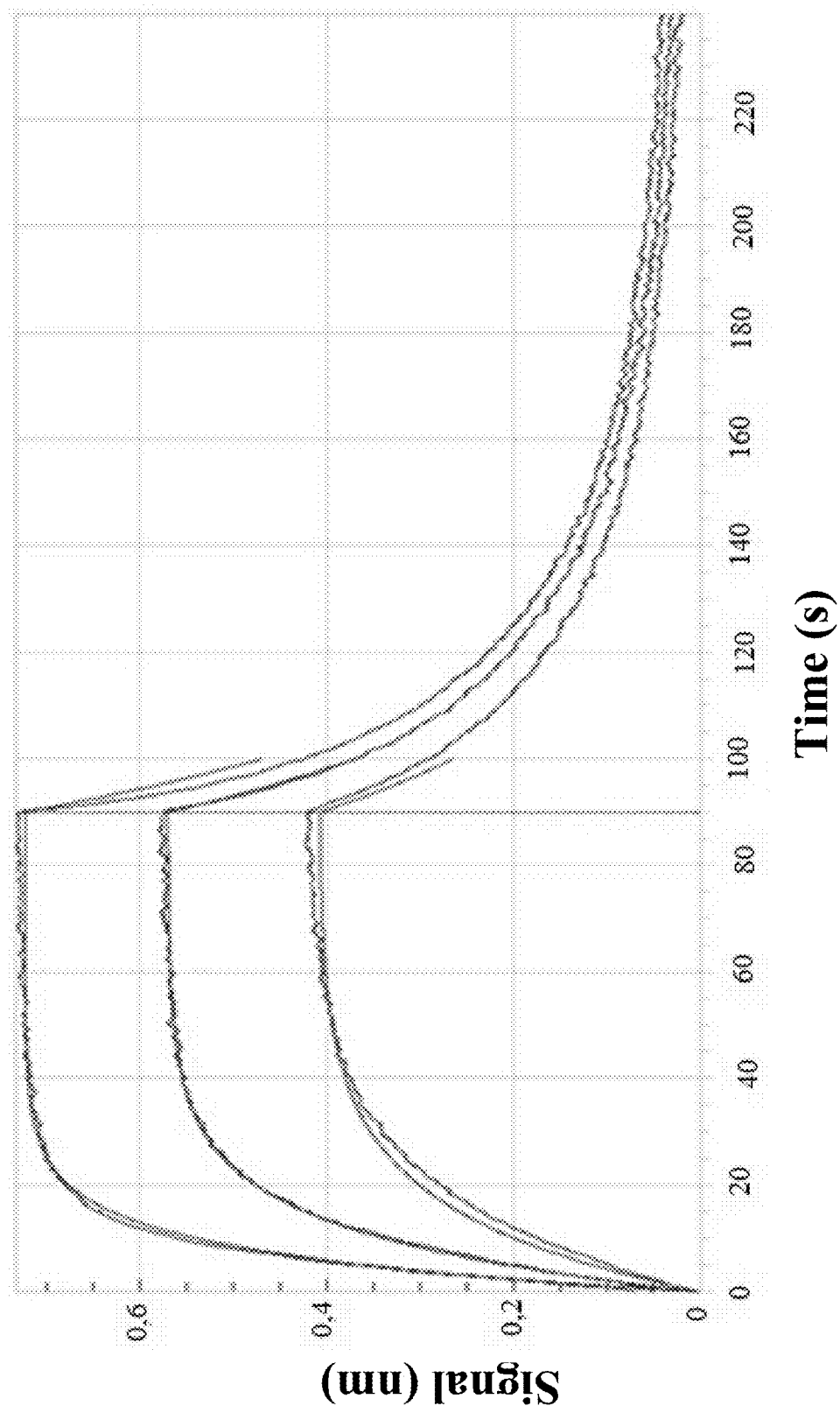
FIG. 16. Analysis of BCD132L-028 candidate-FcγRIIIa-158F interactions on Forte Bio Octet RED 386.
Figure 17:
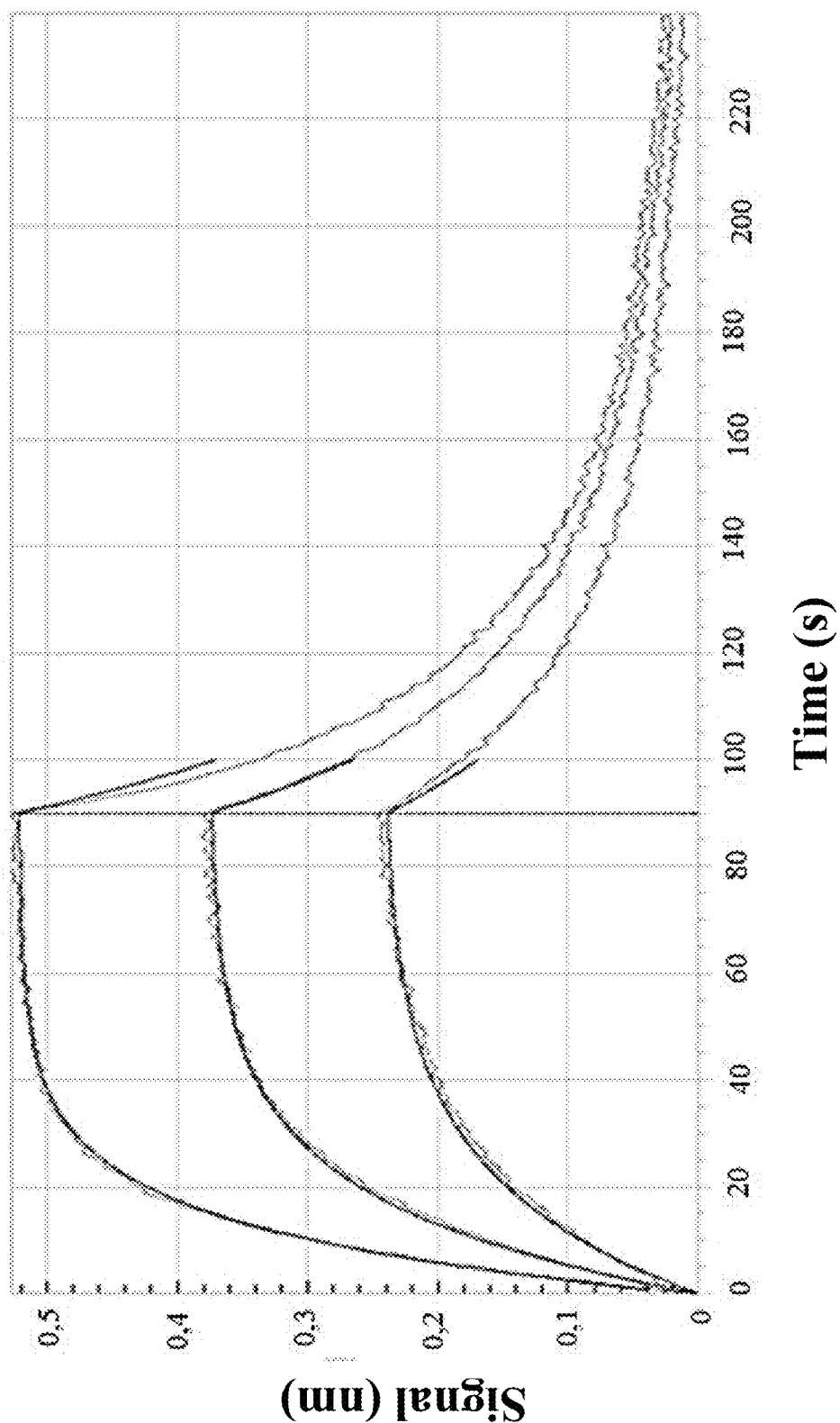
FIG. 17. Analysis of BCD132L-077 (1,2) candidate-FcγRIIIa-158F interactions on Forte Bio Octet RED 386.
Figure 18:
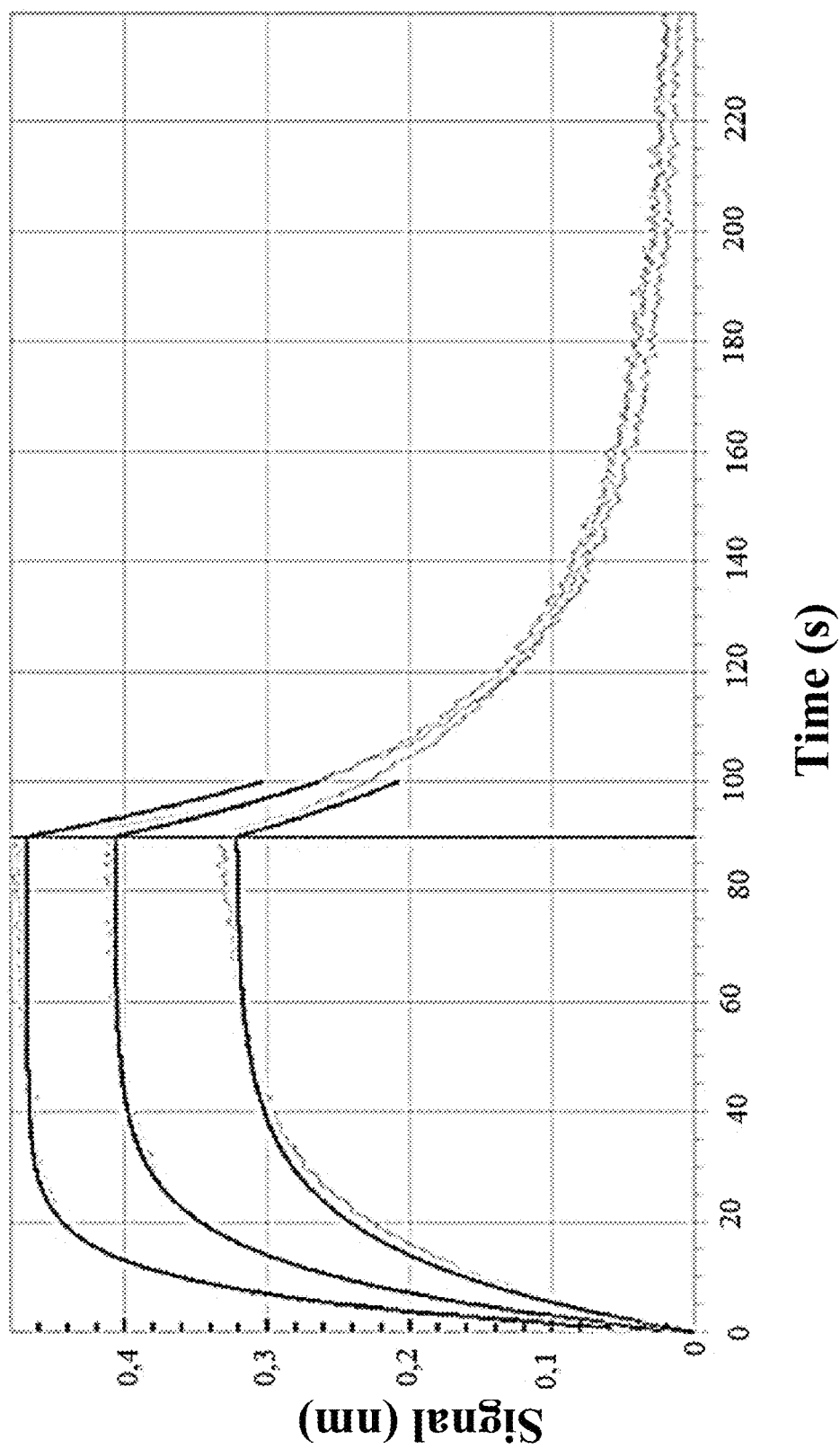
FIG. 18. Analysis of BCD132L-077 (3,4) candidate-FcγRIIIa-158F interactions on Forte Bio Octet RED 386.
Figure 19:
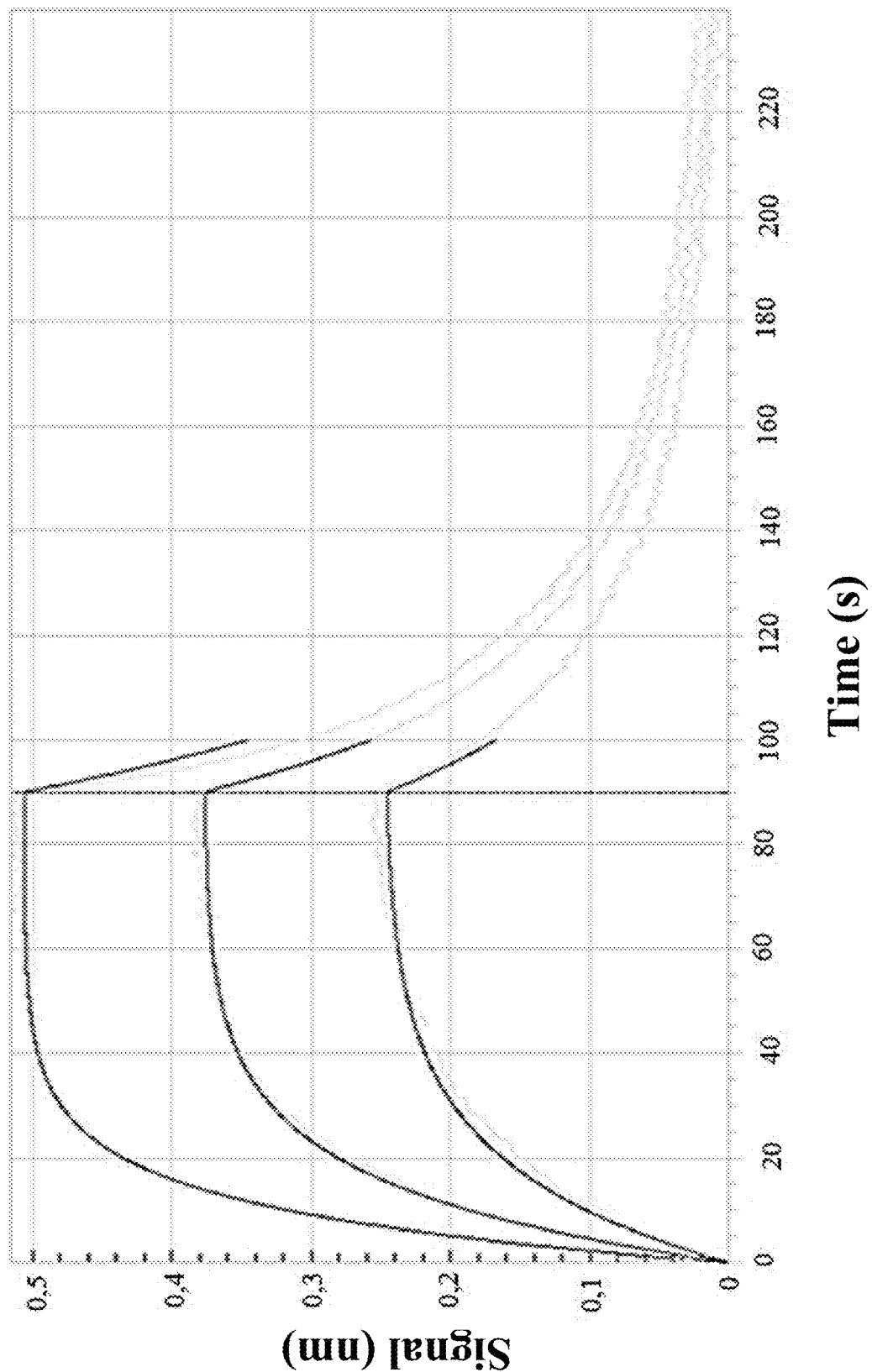
FIG. 19. Analysis of BCD132L-077 (5,6) candidate-FcγRIIIa-158F interactions on Forte Bio Octet RED 386.
Figure 20:
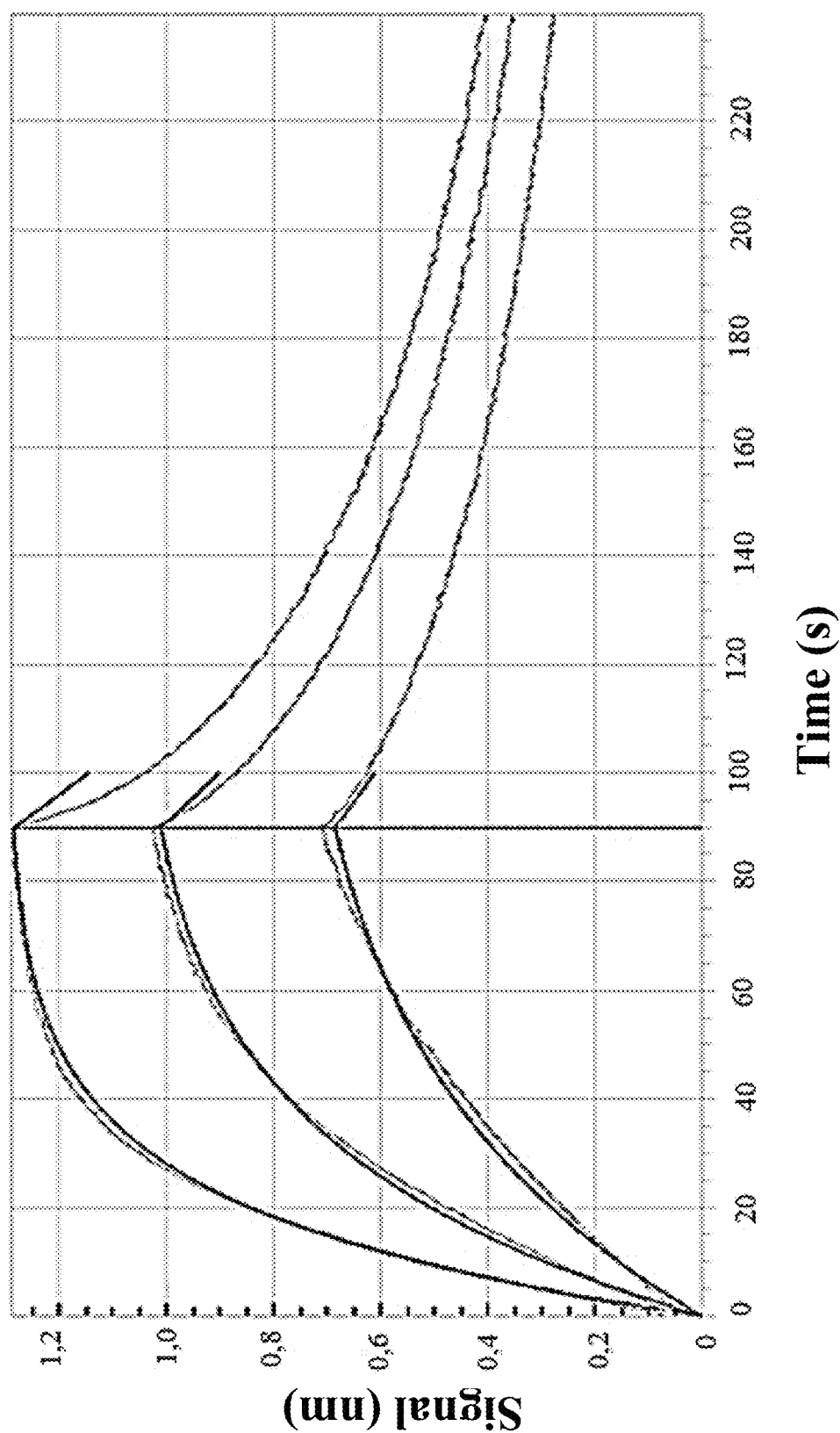
FIG. 20. Analysis of BCD132L-028 candidate-FcγRIIIa-158V interactions on Forte Bio Octet RED 386.
Figure 21:
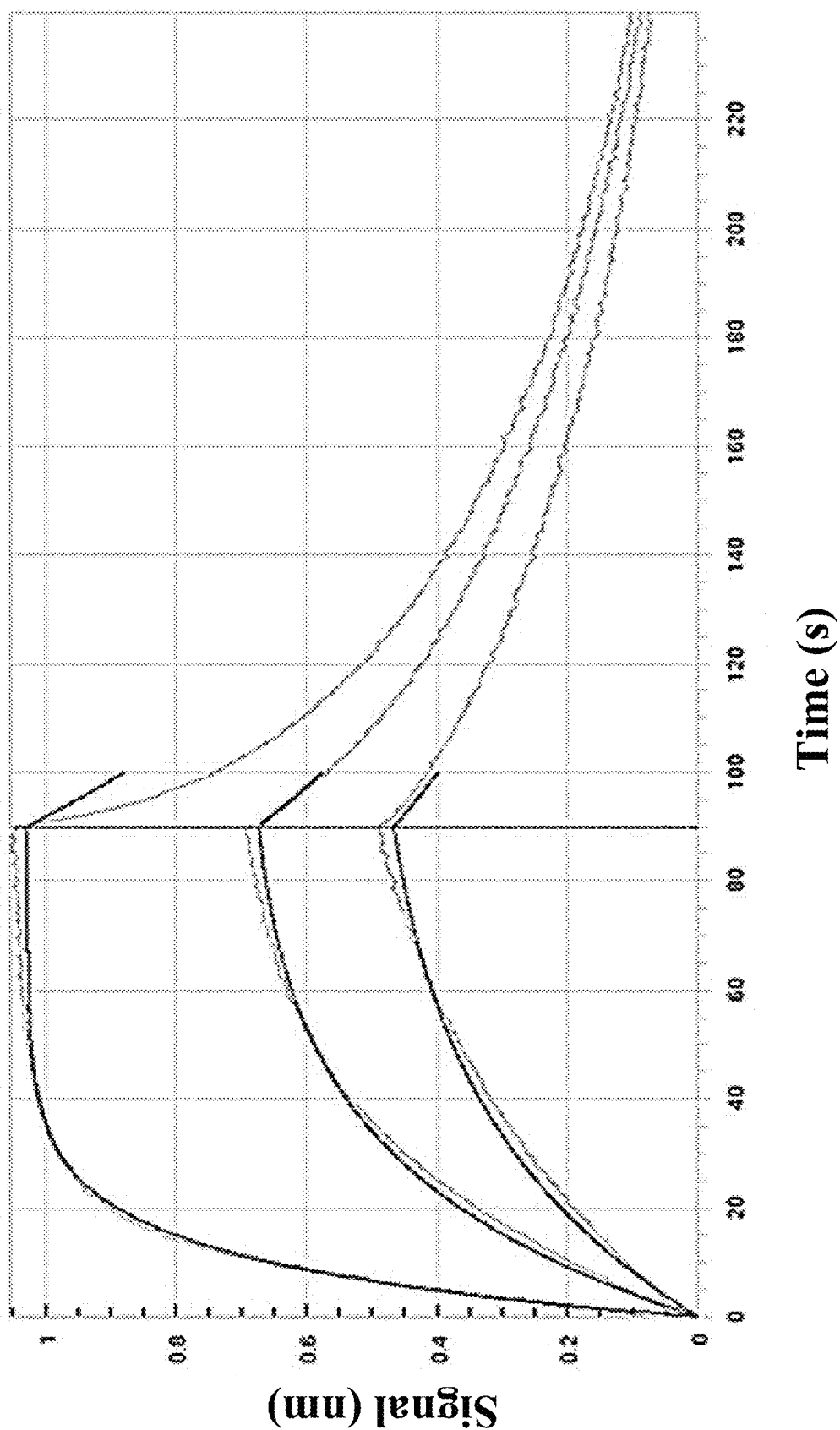
FIG. 21 Analysis of BCD132L-077 (1,2) candidate-FcγRIIIa-158V interactions on Forte Bio Octet RED 386.
Figure 22:
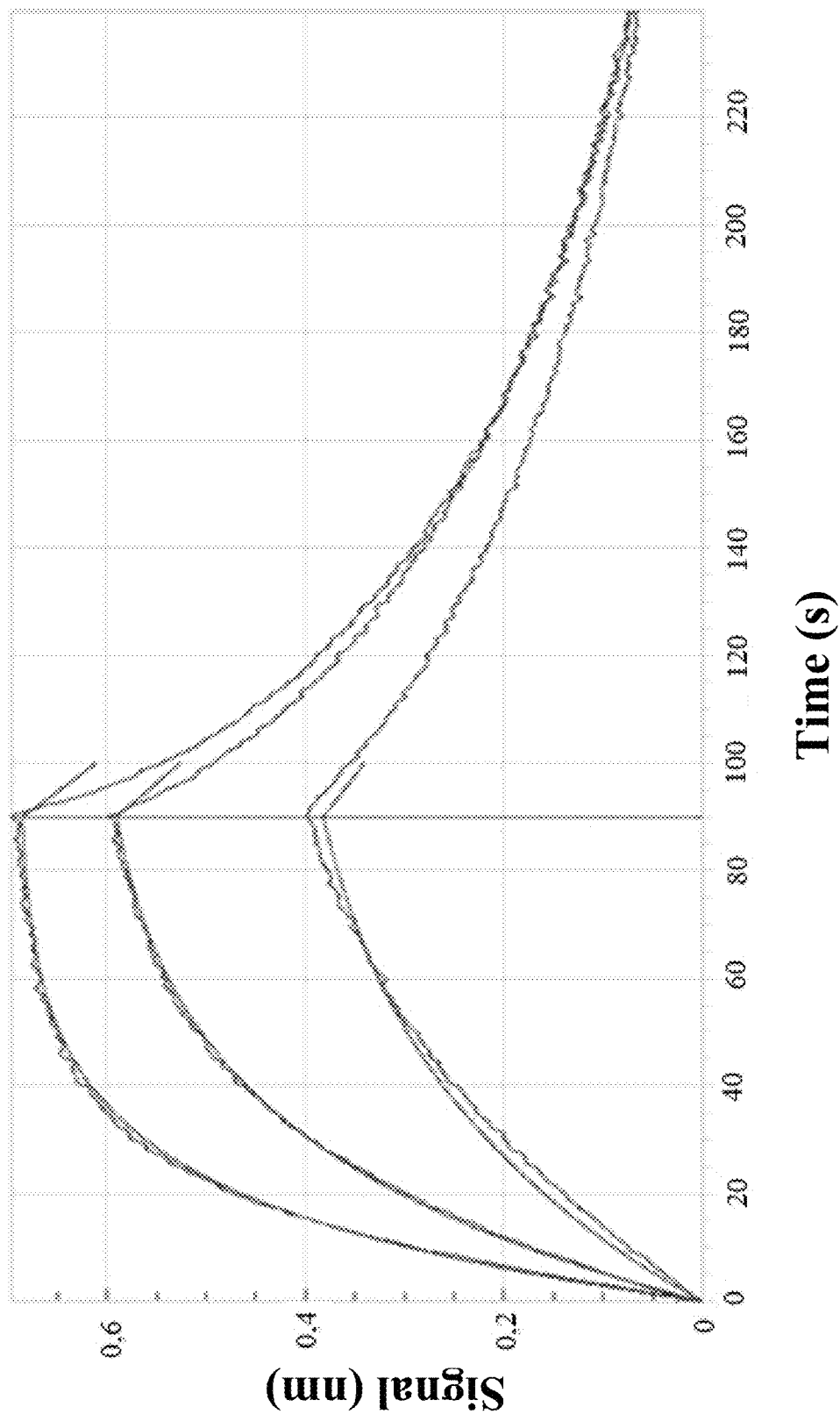
FIG. 22. Analysis of BCD132L-077 (3,4) candidate-FcγRIIIa-158V interactions on Forte Bio Octet RED 386.
Figure 23:
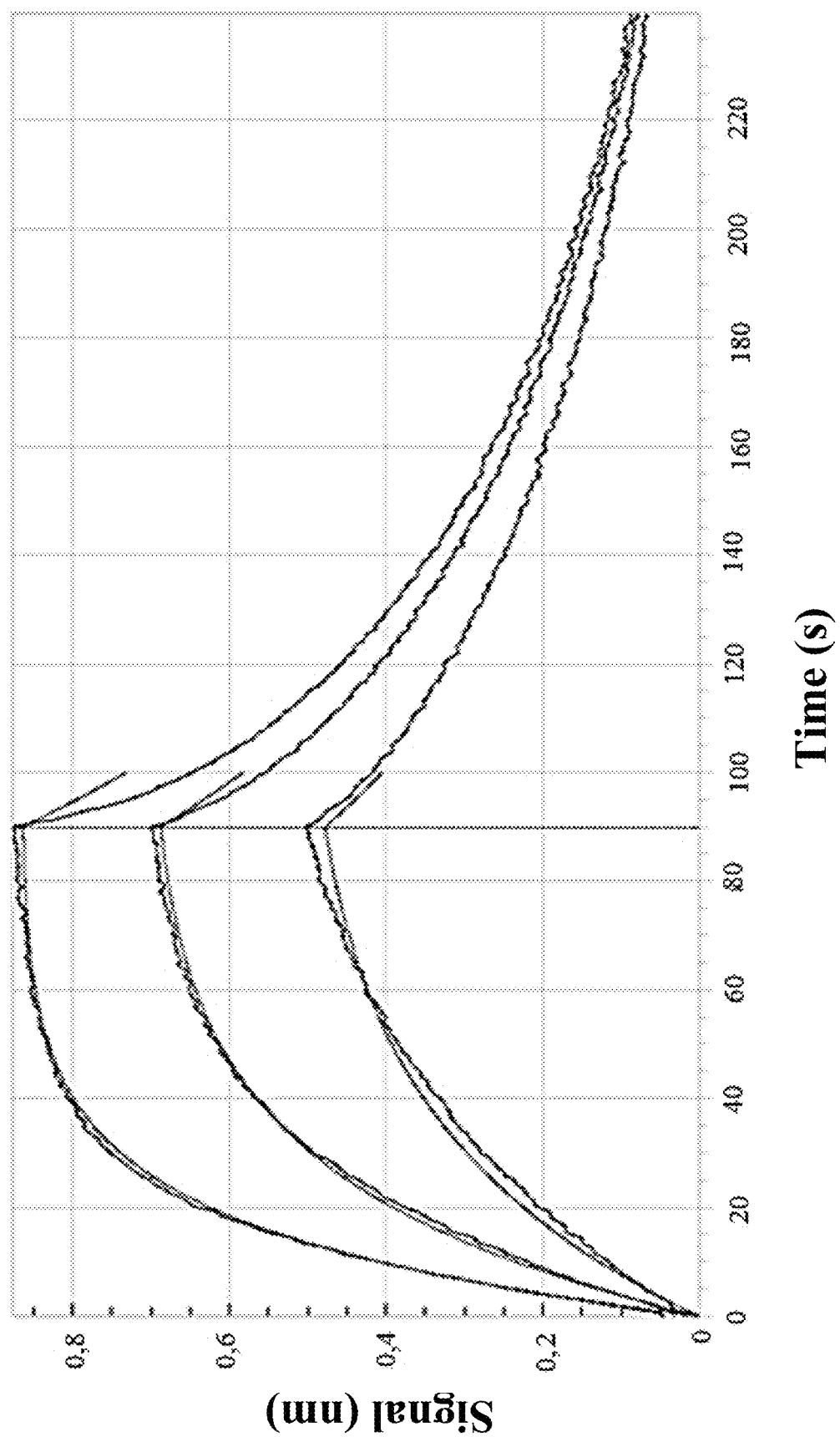
FIG. 23 Analysis of BCD132L-077 (5,6) candidate-FcγRIIIa-158V interactions on Forte Bio Octet RED 386.

116 candidates were transferred for analysis. 67 out of them did not show any binding to peptide. The remaining 49 candidates interacted with peptide with nanomolar and micromolar affinity (FIG. 7 and Table 1).

TABLE 1

| Candidate | Response (nm) | kD (M) | kon (1/Ms) | kdis (1/s) | Full R^2 |
|---|---|---|---|---|---|
| BCD132 L-001 | No binding | No binding | No binding | No binding | No binding |
| BCD132 L-002 | No binding | No binding | No binding | No binding | No binding |
| BCD132 L-003 | 0.2576 | 1.87E−07 | 3.06E+05 | 5.73E−02 | 0.9909 |
| BCD132 L-004 | No binding | No binding | No binding | No binding | No binding |
| BCD132 L-007 | No binding | No binding | No binding | No binding | No binding |
| BCD132 L-008 | 0.1189 | 7.51E−07 | 1.85E+05 | 1.39E−01 | 0.9899 |
| BCD132 L-009 | No binding | No binding | No binding | No binding | No binding |
| BCD132 L-010 | No binding | No binding | No binding | No binding | No binding |
| BCD132 L-011 | 0.2545 | 4.35E−07 | 3.41E+05 | 1.48E−01 | 0.996 |
| BCD132 L-012 | No binding | No binding | No binding | No binding | No binding |
| BCD132 L-013 | No binding | No binding | No binding | No binding | No binding |
| BCD132 L-015 | 0.7312 | 1.51E−07 | 3.00E+05 | 4.54E−02 | 0.9981 |
| BCD132 L-016 | No binding | No binding | No binding | No binding | No binding |
| BCD132 L-017 | No binding | No binding | No binding | No binding | No binding |
| BCD132 L-018 | No binding | No binding | No binding | No binding | No binding |
| BCD132 L-019 | No binding | No binding | No binding | No binding | No binding |
| BCD132 L-020 | No binding | No binding | No binding | No binding | No binding |
| BCD132 L-021 | No binding | No binding | No binding | No binding | No binding |
| BCD132 L-022 | No binding | No binding | No binding | No binding | No binding |
| BCD132 L-023 | No binding | No binding | No binding | No binding | No binding |
| BCD132 L-024 | 0.2377 | 2.72E−07 | 5.86E+05 | 1.59E−01 | 0.9969 |
| BCD132 L-025 | No binding | No binding | No binding | No binding | No binding |
| BCD132 L-026 | 0.189 | 9.74E−08 | 8.72E+05 | 8.50E−02 | 0.9761 |
| BCD132 L-028 | 0.2631 | 1.35E−07 | 9.30E+05 | 1.26E−01 | 0.9849 |
| BCD132 L-029 | No binding | No binding | No binding | No binding | No binding |
| BCD132 L-030 | 0.7685 | 1.11E−05 | 2.39E+03 | 2.65E−02 | 0.8223 |
| BCD132 L-031 | No binding | No binding | No binding | No binding | No binding |
| BCD132 L-033 | No binding | No binding | No binding | No binding | No binding |
| BCD132 L-034 | 0.8465 | 8.45E−06 | 3.73E+03 | 3.15E−02 | 0.9308 |
| BCD132 L-035 | 1.3668 | 6.56E−06 | 3.35E+03 | 2.20E−02 | 0.9829 |
| BCD132 L-037 | No binding | No binding | No binding | No binding | No binding |
| BCD132 L-038 | No binding | No binding | No binding | No binding | No binding |
| BCD132 L-039 | 1.493 | 6.91E−06 | 2.44E+03 | 1.69E−02 | 0.9924 |
| BCD132 L-040 | 1.099 | 9.14E−06 | 3.11E+03 | 2.84E−02 | 0.9675 |
| BCD132 L-041 | No binding | No binding | No binding | No binding | No binding |
| BCD132 L-042 | 0.745 | 8.51E−06 | 4.46E+03 | 3.80E−02 | 0.8425 |
| BCD132 L-043 | No binding | No binding | No binding | No binding | No binding |
| BCD132 L-044 | 0.638 | 8.90E−06 | 3.55E+03 | 3.16E−02 | 0.8215 |
| BCD132 L-045 | 0.7287 | 1.04E−05 | 3.70E+03 | 3.83E−02 | 0.9562 |
| BCD132 L-046 | 0.4142 | 1.38E−05 | 4.68E+03 | 6.44E−02 | 0.9478 |
| BCD132 L-047 | No binding | No binding | No binding | No binding | No binding |
| BCD132 L-048 | No binding | No binding | No binding | No binding | No binding |
| BCD132 L-049 | No binding | No binding | No binding | No binding | No binding |
| BCD132 L-050 | No binding | No binding | No binding | No binding | No binding |
| BCD132 L-051 | No binding | No binding | No binding | No binding | No binding |
| BCD132 L-052 | No binding | No binding | No binding | No binding | No binding |
| BCD132 L-053 | 0.1125 | 1.36E−07 | 4.64E+05 | 6.31E−02 | 0.9252 |
| BCD132 L-054 | 0.083 | 1.59E−07 | 3.10E+05 | 4.92E−02 | 0.8279 |
| BCD132 L-055 | No binding | No binding | No binding | No binding | No binding |
| BCD132 L-056 | No binding | No binding | No binding | No binding | No binding |
| BCD132 L-057 | No binding | No binding | No binding | No binding | No binding |
| BCD132 L-058 | 0.1308 | 1.30E−07 | 2.08E+06 | 2.70E−01 | 0.9744 |
| BCD132 L-059 | No binding | No binding | No binding | No binding | No binding |
| BCD132 L-060 | No binding | No binding | No binding | No binding | No binding |
| BCD132 L-061 | No binding | No binding | No binding | No binding | No binding |
| BCD132 L-062 | No binding | No binding | No binding | No binding | No binding |
| BCD132 L-063 | No binding | No binding | No binding | No binding | No binding |
| BCD132 L-064 | No binding | No binding | No binding | No binding | No binding |
| BCD132 L-065 | 0.0551 | 6.48E−08 | 1.01E+06 | 6.53E−02 | 0.8386 |
| BCD132 L-066 | 0.0398 | 1.14E−05 | 4.10E+03 | 4.66E−02 | 0.8193 |
| BCD132 L-068 | 0.0984 | 9.34E−08 | 9.50E+05 | 8.87E−02 | 0.876 |
| BCD132 L-069 | 0.1078 | 1.29E−07 | 6.96E+05 | 8.96E−02 | 0.8737 |

TABLE 1-continued

| Candidate | Response (nm) | kD (M) | kon (1/Ms) | kdis (1/s) | Full R^2 |
|---|---|---|---|---|---|
| BCD132 L-070 | No binding | No binding | No binding | No binding | No binding |
| BCD132 L-071 | 0.3793 | 1.36E−07 | 7.59E+05 | 1.03E−01 | 0.9755 |
| BCD132 L-072 | 0.2878 | 9.15E−08 | 7.82E+05 | 7.16E−02 | 0.8842 |
| BCD132 L-073 | No binding | No binding | No binding | No binding | No binding |
| BCD132 L-074 | No binding | No binding | No binding | No binding | No binding |
| BCD132 L-075 | 0.4394 | 1.01E−07 | 8.20E+05 | 8.29E−02 | 0.9752 |
| BCD132 L-076 | 0.2166 | 8.14E−08 | 8.45E+05 | 6.88E−02 | 0.7702 |
| BCD132 L-077 | 0.065 | 7.48E−08 | 9.24E+05 | 6.91E−02 | 0.8382 |
| BCD132 L-079 | 0.1921 | 1.88E−07 | 3.16E+05 | 5.96E−02 | 0.9433 |
| BCD132 L-080 | No binding | No binding | No binding | No binding | No binding |
| BCD132 L-081 | No binding | No binding | No binding | No binding | No binding |
| BCD132 L-082 | 0.0695 | 7.99E−08 | 1.05E+06 | 8.41E−02 | 0.9063 |
| BCD132 L-083 | No binding | No binding | No binding | No binding | No binding |
| BCD132 L-084 | 0.3092 | 1.86E−07 | 3.41E+05 | 6.35E−02 | 0.9697 |
| BCD132 L-085 | No binding | No binding | No binding | No binding | No binding |
| BCD132 L-087 | No binding | No binding | No binding | No binding | No binding |
| BCD132 L-088 | No binding | No binding | No binding | No binding | No binding |
| BCD132 L-089 | 0.1279 | 5.94E−08 | 1.75E+06 | 1.04E−01 | 0.879 |
| BCD132 L-092 | No binding | No binding | No binding | No binding | No binding |
| BCD132 L-093 | No binding | No binding | No binding | No binding | No binding |
| BCD132 L-094 | No binding | No binding | No binding | No binding | No binding |
| BCD132 L-095 | 0.5518 | 7.72E−08 | 1.04E+06 | 7.99E−02 | 0.9778 |
| BCD132 L-097 | 0.2544 | 7.32E−08 | 1.59E+06 | 1.17E−01 | 0.9603 |
| BCD132 L-098 | No binding | No binding | No binding | No binding | No binding |
| BCD132 L-099 | No binding | No binding | No binding | No binding | No binding |
| BCD132 L-100 | 0.639 | 8.07E−08 | 7.36E+05 | 5.95E−02 | 0.98 |
| BCD132 L-101 | No binding | No binding | No binding | No binding | No binding |
| BCD132 L-102 | No binding | No binding | No binding | No binding | No binding |
| BCD132 L-103 | No binding | No binding | No binding | No binding | No binding |
| BCD132 L-104 | No binding | No binding | No binding | No binding | No binding |
| BCD132 L-105 | 0.207 | 6.28E−08 | 1.08E+06 | 6.75E−02 | 0.8085 |
| BCD132 L-106 | 0.2847 | 4.65E−08 | 2.30E+06 | 1.07E−01 | 0.8997 |
| BCD132 L-107 | No binding | No binding | No binding | No binding | No binding |
| BCD132 L-109 | No binding | No binding | No binding | No binding | No binding |
| BCD132 L-110 | No binding | No binding | No binding | No binding | No binding |
| BCD132 L-111 | No binding | No binding | No binding | No binding | No binding |
| BCD132 L-112 | 0.3355 | 6.30E−08 | 1.86E+06 | 1.17E−01 | 0.9556 |
| BCD132 L-113 | No binding | No binding | No binding | No binding | No binding |
| BCD132 L-114 | 0.3495 | 6.03E−08 | 1.22E+06 | 7.36E−02 | 0.877 |
| BCD132 L-115 | No binding | No binding | No binding | No binding | No binding |
| BCD132 L-116 | No binding | No binding | No binding | No binding | No binding |
| BCD132 L-117 | No binding | No binding | No binding | No binding | No binding |
| BCD132 L-118 | 0.5571 | 9.04E−08 | 9.57E+05 | 8.66E−02 | 0.973 |
| BCD132 L-119 | 0.2468 | 4.91E−08 | 2.36E+06 | 1.16E−01 | 0.9109 |
| BCD132 L-120 | 0.3083 | 6.95E−08 | 1.69E+06 | 1.18E−01 | 0.9443 |
| BCD132 L-121 | 0.1834 | 5.97E−08 | 2.52E+06 | 1.50E−01 | 0.9316 |
| BCD132 L-123 | No binding | No binding | No binding | No binding | No binding |
| BCD132 L-124 | No binding | No binding | No binding | No binding | No binding |
| BCD132 L-126 | 0.2006 | 4.24E−08 | 2.19E+06 | 9.29E−02 | 0.8596 |
| BCD132 L-129 | 0.4355 | 9.00E−08 | 1.11E+06 | 9.98E−02 | 0.9724 |
| BCD132 L-130 | 0.4193 | 8.67E−08 | 1.08E+06 | 9.31E−02 | 0.9485 |
| BCD132 L-131 | 0.4494 | 9.39E−08 | 9.77E+05 | 9.17E−02 | 0.9612 |
| BCD132 L-132 | 0.7019 | 1.07E−07 | 8.38E+05 | 8.97E−02 | 0.9888 |
| BCD132 L-133 | 0.2948 | 5.66E−08 | 2.12E+06 | 1.20E−01 | 0.9316 |

Candidates BCD132L-026, BCD132L-028, BCD132L-075 and BCD132L-077 were selected based on the results of the above analysis.

Example 9. Determination of Affinity of Final Candidates after Transient Production to CD20 Using Forte Bio Octert RED 384

SAX biosensors and biotin-modified CD20 peptide (Sigma Aldrich) were used for the study. Antibody Rituximab was used as a control. SAX biosensors were steeped into a solution containing biotinylated CD20 peptide at a concentration of 20 μg/ml, where the peptide was immobilized. Further analysis was conducted at 30° C. using PBS containing 0.1% Tween 20 and 0.1% BSA as a working buffer.

After baseline recording in buffer solution, the sensors were immersed into wells with antibody solution at a concentration of 10 μg/ml for 210 seconds, where the complex was associated. Complex dissociation in buffer solution was then detected for 100 seconds.

Binding curves, after subtracting a reference signal, were analyzed using Octet Data Analysis software (Version 9.0) in accordance with the standard procedure using 1:1 interaction model (see FIGS. 8-11).

| | | | | | |
|---|---|---|---|---|---|
| BCD132L-026 | 0.5411 | 3.99E−08 | 6.98E+05 | 2.79E−02 | 0.9795 |
| BCD132L-028 | 0.4703 | 6.28E−08 | 4.17E+05 | 2.62E−02 | 0.9924 |
| BCD132L-075 | 0.8719 | 6.23E−08 | 3.30E+05 | 2.06E−02 | 0.9969 |
| BCD132L-077 | 0.4774 | 2.76E−08 | 6.36E+05 | 1.75E−02 | 0.9413 |

Candidates BCD132L-028 and BCD132L-077 were selected based on the results of the above analysis.

Figure 24:
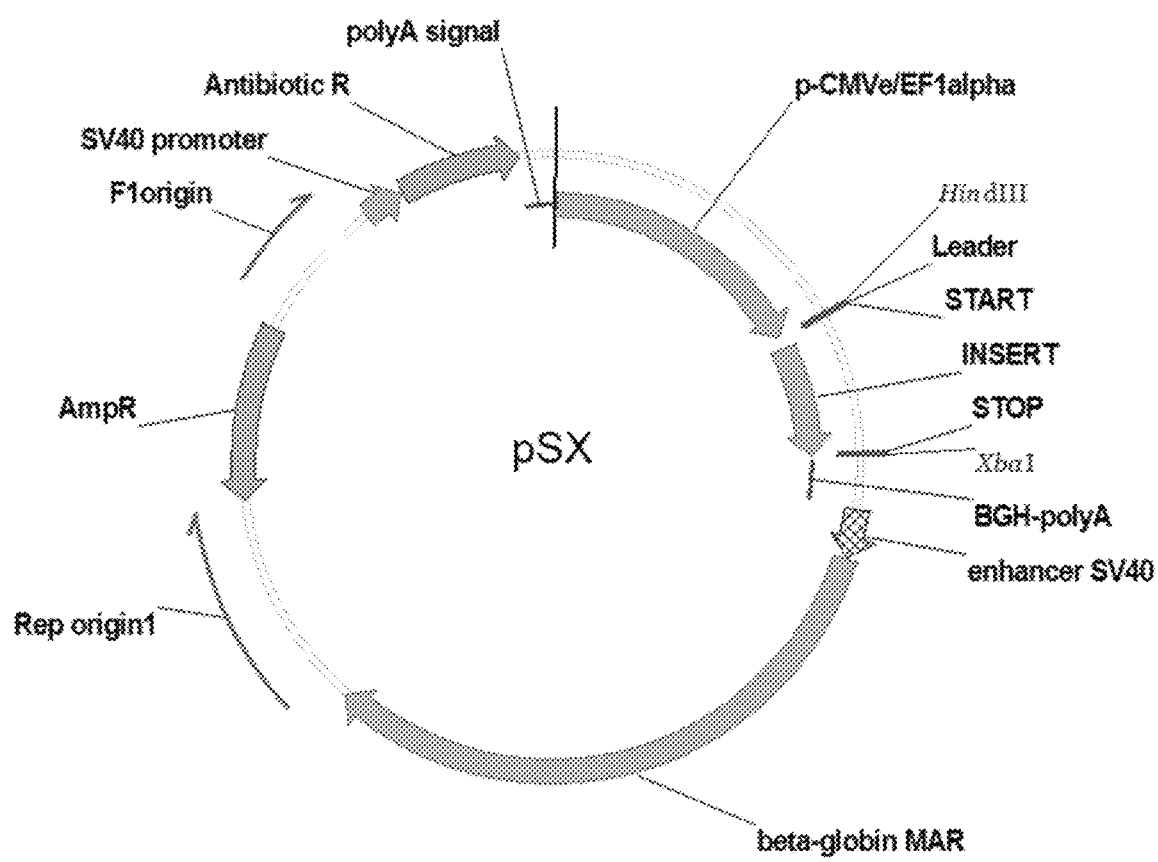
FIG. 24. Map of expression vector pSX.

Example 10. Preparation of a Cell Line Stably Producing Antibodies in IgG1 Format Based on the results of the assays above, BCD132-L-028, BCD132-L-077 showed the best performance. Their heavy and light chain sequences were cloned into HindIII, XbaI sites of vectors pSX (FIG. 24). The resulting plasmids were cultured in *E. coli* cells, 600-700 µg was isolated using BenchPro. The plasmids were linearised overnight by PvuI endonuclease, and then re-precipitated with ethanol and brought to final concentration of 900-1100 ng/µl.

CHO-K1-S cell line was cultured in 5.3.87 MM medium (FBS-free synthetic medium developed by BIOCAD)+6 mM Glutamine. Transfection with gene constructs comprising encoding sequences of BCD132-L-028, BCD132-L-077 candidate chains was performed by electroporation using Nucleofector™ (Lonza) according to the manufacturer protocol.

The day after transfection, the transfected culture was under selection for 24 days by adding puromycin (final concentration of 7.2 µg/ml), hygromycin B (final concentration of 640 µg/ml) to the medium. The selected cell population was cloned. Cell clones expressing BCD132-L-028, BCD132-L-077, respectively, were selected based on the results of analysis of target protein level/structure homogeneity, taking into account growth rate, population homogeneity, and absence of morphological changes, whereas candidates BCD132-L-026 and BCD-132-L-075 were excluded.

Example 11. Determination of Affinity of Final Candidates Cultured in Stable Cell Lines to CD20 on Forte Bio Octert RED 384

SAX biosensors and biotin-modified CD20 peptide (Sigma Aldrich) were used for the study. Antibody Rituximab was used as a control. SAX biosensors were steeped into a solution containing biotinylated CD20 peptide at a concentration of 20 µg/ml, where the peptide was immobilized. Further analysis was conducted at 30° C. using PBS containing 0.1% Tween 20 and 0.1% BSA as a working buffer.

After baseline recording in buffer solution, the sensors were immersed into wells containing antibody solution at a concentration of 10 µg/ml for 150 seconds, where the complex was associated. Complex dissociation in buffer solution was then detected for 300 seconds.

Binding curves, after subtracting a reference signal, were analyzed using Octet Data Analysis software (Version 9.0) in accordance with the standard procedure using 1:1 interaction model (FIG. 12-15).

| | | | | | |
|---|---|---|---|---|---|
| BCD132L-028 | 0.2717 | 7.57E−08 | 9.05E+05 | 6.85E−02 | 0.9754 |
| BCD132L-077 (1, 2) | 0.4031 | 7.39E−08 | 6.41E+05 | 4.74E−02 | 0.9846 |
| BCD132L-077 (3, 4) | 0.2913 | 7.49E−08 | 8.47E+05 | 6.34E−02 | 0.9776 |
| BCD132L-077 (5, 6) | 0.5857 | 6.71E−08 | 9.52E+05 | 6.39E−02 | 0.9682 |

Example 12. Determination of Affinity of Final Candidates Cultured in Stable Cell Lines to FcγRIIIa-158F on Forte Bio Octert RED 384

SAX biosensors and biotin-modified FcγRIIIa-158F proteins (Sigma Aldrich) were used for the study. SAX biosensors were steeped into a solution containing the biotinylated protein at a concentration of 5 µg/ml, where the protein was immobilized to a signal level of 0.5 nm. Further analysis was conducted at 30° C. using PBS containing 0.1% Tween 20 and 0.1% BSA as a working buffer.

After baseline recording, the sensors were steeped into wells containing a solution of antibodies at various concentrations for 90 seconds, where the complex was associated. Complex dissociation in buffer solution was then detected for 150 seconds.

Binding curves, after subtracting a reference signal, were analyzed using Octet Data Analysis software (Version 9.0) in accordance with the standard procedure using 1:1 interaction model (FIGS. 16-19).

| | | | | |
|---|---|---|---|---|
| BCD132L-028 | 5.93E−08 | 7.273E05 | 4.316E−02 | 0.9946 |
| BCD132L-077 (1, 2) | 4.47E−08 | 7.658E05 | 3.423E−02 | 0.9976 |
| BCD132L-077 (3, 4) | 5.41E−08 | 8.084E05 | 4.375E−02 | 0.991 |
| BCD132L-077 (5, 6) | 4.17E−08 | 9.231E05 | 3.845E−02 | 0.9954 |

Example 13. Determination of Affinity of Final Candidates Cultured in Stable Cell Lines to FcγRIIIa-158V on Forte Bio Octert RED 384

SAX biosensors and biotin-modified FcγRIIIa-158V proteins (Sigma Aldrich) were used for the study. SAX biosensors were steeped into a solution containing the biotinylated protein at a concentration of 5 µg/ml, where the protein was immobilized to a signal level of 0.5 nm. Further analysis was conducted at 30° C. using PBS containing 0.1% Tween 20 and 0.1% BSA as a working buffer.

After baseline recording, the sensors were steeped into wells containing a solution of antibodies at various concentrations for 90 seconds, where the complex was associated. Complex dissociation in buffer solution was then detected for 150 seconds.

Binding curves, after subtracting a reference signal, were analyzed using Octet Data Analysis software (Version 9.0) in accordance with the standard procedure using 1:1 interaction model (FIGS. 20-23).

| | | | | |
|---|---|---|---|---|
| BCD132L-028 | 1.78E−08 | 6.385E05 | 1.139E−02 | 0.9963 |
| BCD132L-077 (1, 2) | 2.38E−08 | 6.563E05 | 1.564E−02 | 0.9942 |
| BCD132L-077 (3, 4) | 1.66E−08 | 6.906E05 | 1.149E−02 | 0.9961 |
| BCD132L-077 (5, 6) | 2.27E−08 | 7.311E05 | 1.659E−02 | 0.9952 |

Example 14. Measurement of Specific Binding of BCD-132-L-028 and BCD-132-L-077 to CD20 Receptor on WIL2-S Cell Line Using Flow Cytometry MabThera (Rituximab) was used as a control antibody. Samples and a control antibody were diluted to a concentration of 200 µg/ml, titrated with an increment of 4 in Stain Buffer (PBS, 0.5% BSA, 0.1% NaN3). WIL2-S (ATCC® CRL8885) cell suspension at a concentration of $1 \times 10^6$ cells/ml was incubated with a titer of solutions of standard and test samples. The suspension was stirred and incubated for 30 min in ice. After the time of incubation, the plate was centrifuged, supernatant was collected, 100 µl of Stain Buffer was added, the mixture was resuspended and centrifuged. Supernatant was collected, precipitate was resuspended in a solution of conjugated fluorescent anti-human Fc-PE antibodies (Jackson Immunoresearch, 109-115-098) in Stain Buffer. The plate was incubated for 30 min in ice in dark. After the time of incubation, the plate was centrifuged, supernatant was collected, 100 µl of Stain Buffer was added, the mixture was resuspended and centrifuged. Supernatant was collected, precipitate was resuspended in 150 µl of Stain Buffer and assayed by flow cytometer Guava12HT (Merck Millipore). Data was analyzed using the InCyte module of guavaSoft 3.1.1 software.

Figure 25:
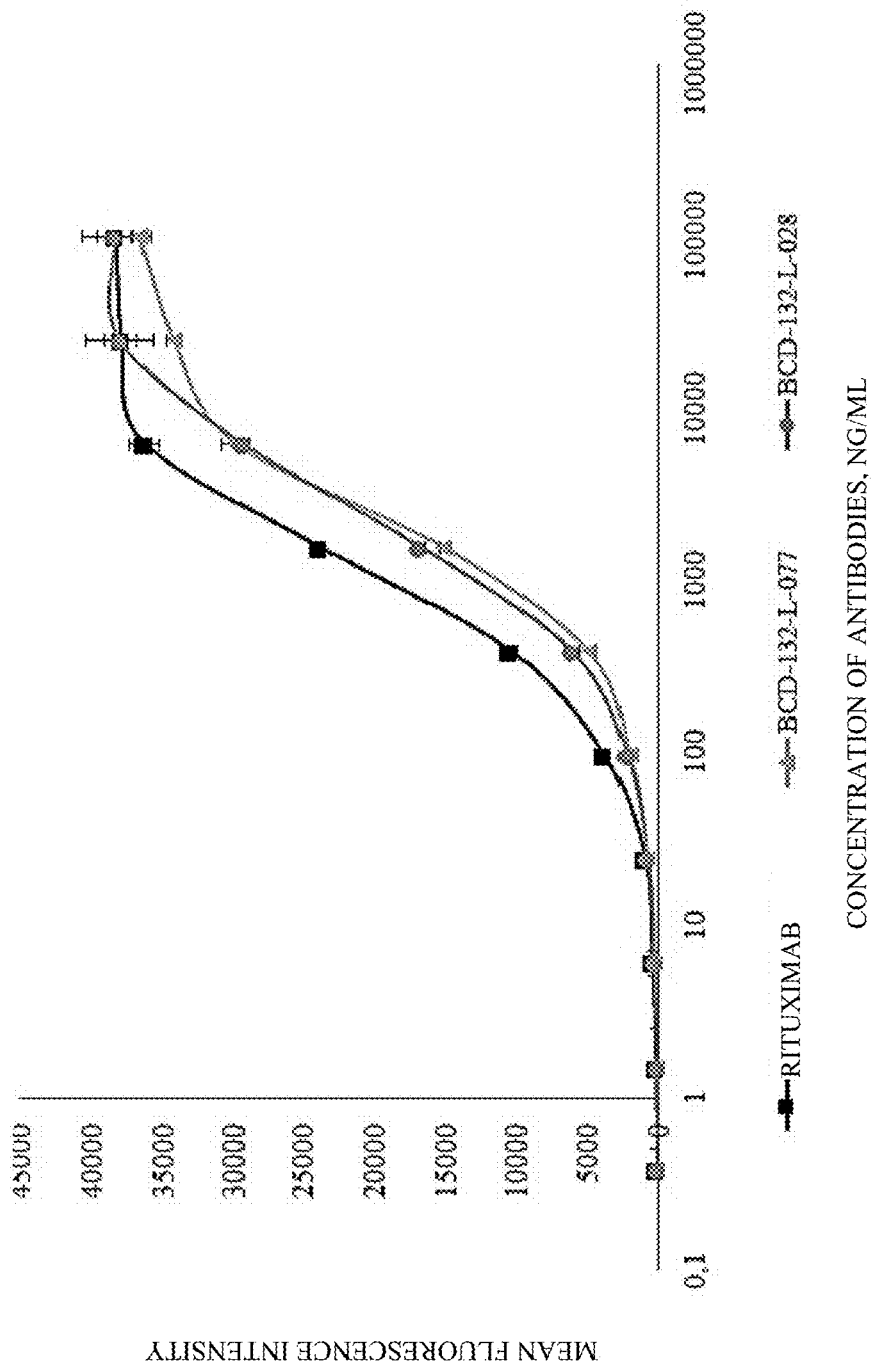
FIG. 25. Measurement of specific binding of BCD-132-L-028 and BCD-132-L-077 to CD20 receptor on WIL2-S cell line using flow cytometry as compared to MabThera.

Level of specific binding of test antibodies BCD-132-L-028 and BCD-132-L-077 to CD20 receptor on WIL2-S cell line is identical to that of MabThera (Rituximab). The results are shown in FIG. 25.

Example 15. Measurement of Complement Dependent Cytotoxicity of BCD-132-L-028 and BCD-132-L-077

WIL2-S (ATCC® CRL-8885™) cell line was used for the complement dependent cytotoxicity assay.

The assay was conducted in RPMI-1640 supplemented with 2 mM glutamine, 0.1% bovine serum albumin, 50 µg/ml of gentamicin. Test antibodies BCD-132-L-028, BCD-132-L-077 and MabThera (Rituximab) were diluted in series from a concentration of 50 µg/ml. The resulting solutions were added to 96-well plates at 50 µl/well. WIL2-S cell suspension at $1\times10^6$ cells/ml was prepared and added to the plate wells at 50 µl/well. A working solution of complement (Quidel, A113) was prepared and added to culture plates at 50 µl/well.

The plates were incubated for 2 hours at 37° C., 5% $CO_2$. After the time of incubation, 15 µl/well of Alamar blue dye was added to the plate wells, the plate was incubated at 37° C., 5% $CO_2$ until gradient staining was seen. Fluorescence was measured using Infinite M200Pro plate reader at excitation/emission wavelength of 544/590 nm.

Figure 26:
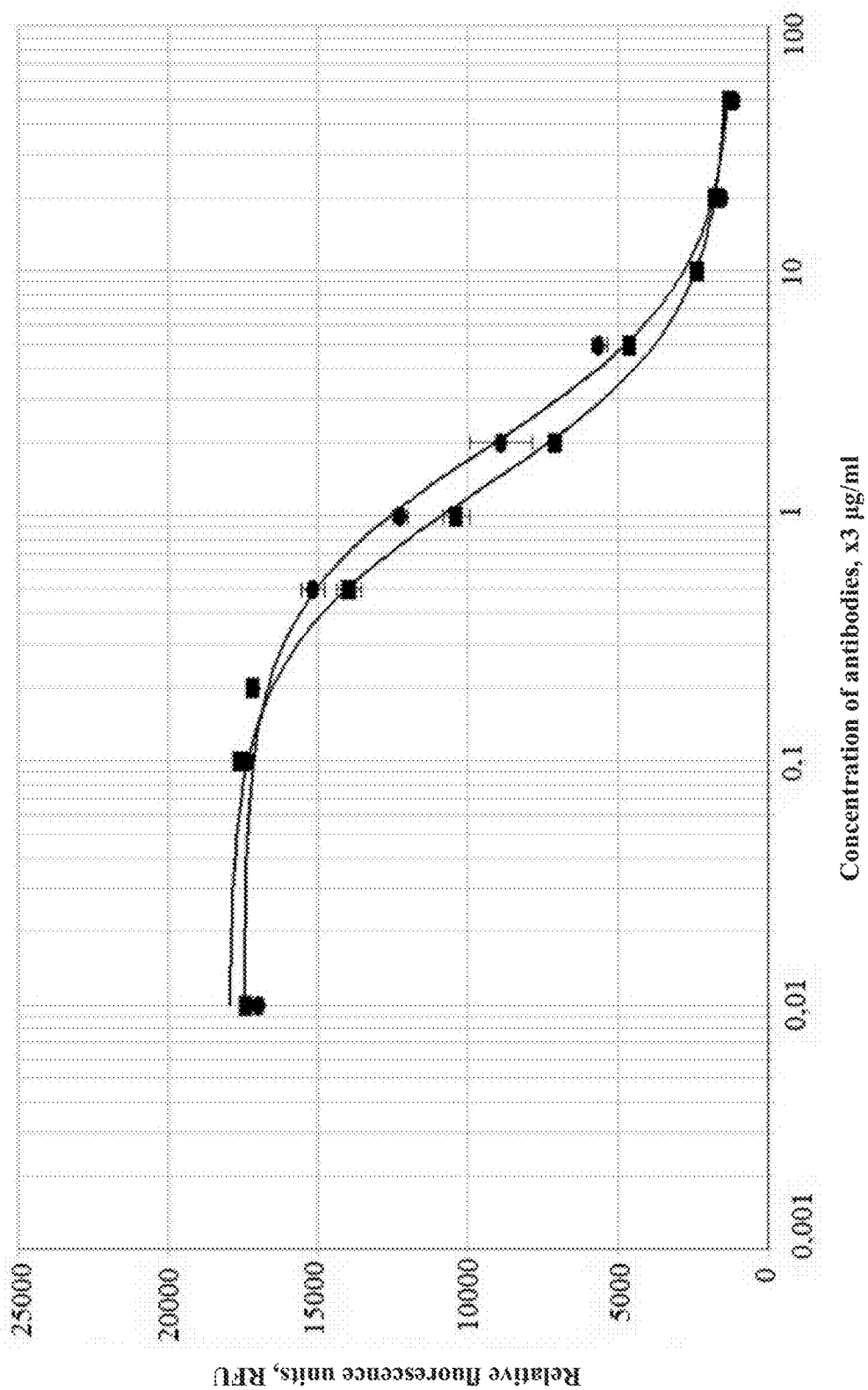
FIG. 26. Measurement of complement dependent cytotoxicity of BCD-132-L-028 and BCD-132-L-077 as compared to MabThera.

The level of complement dependent cytotoxicity of BCD-132-L-028 and BCD-132-L-077 is identical to that of MabThera (Rituximab). The results are shown in FIG. 26, FIG. 27.

Example 16. Measurement of Antibody-Dependent Cellular Cytotoxicity of BCD-132-L-028 and BCD-132-L-077 Using Reporter Lines Jurkat-NFAT-CD16

WIL-2S (ATCC® CRL-8885™) was used as a target line to measure antibody-dependent cellular cytotoxicity. As effector cells, we employed reporter lines Jurkat-NFAT-CD16 High (high affinity allotype of CD16, V158) and Jurkat-NFAT-CD16 Low (low affinity allotype of CD16, F158) stably expressing the cell surface FcγRIIIa (CD16a) receptor and carrying a luciferase-encoding gene under control of NFAT response elements.

We prepared WIL-2S cell suspension at $0.5\times10^6$ cells/ml in RPMI1640 supplemented with 2 mM L-Gln, 4% (v/v) low IgG FBS and 5 µg/ml gentamicin. 25 µl/well of suspension of target cells was added to culture plates with white walls.

We added a titer of BCD-132-L-028 or BCD-132-L-077 and MabThera (Rituximab) from 5 µg/ml with an increment of 5 (25 µl/well), and suspension at $3\times10^6$ cells/ml of reporter line Jurkat-NFAT-CD16 High or Low (25 µl/well). The plates were stirred and incubated at 37° C., 5% CO2 for 4-8 hours.

After the time of incubation, we added 75 µl/well of Bio-Glo luciferase assay reagent (Promega) and measured luminescence using Infinite M200Pro under 100 ms integration time.

BCD-132-L-028 and BCD-132-L-077 show a significantly higher ADCC activity as compared to that of MabThera: the activity is 3-4 times higher when using the reporter line with a high affinity allotype of CD16, and 12-16 times higher when using the reporter line with a low affinity allotype of CD16. The results are shown in FIG. 28; FIG. 29 shows the results for the reporter line with a low affinity allotype of CD16, and FIG. 30, FIG. 31 show the results for the reporter line with a high affinity allotype of CD16.

Example 17. Measurement of B Cell Depletion by CD19+Induced by BCD-132-L-028 and BCD-132-L-077 Using Whole Blood from Healthy Donors The activity of test samples was measured ex vivo using whole blood from healthy donors with the CD16a receptor allotypes: FF (low affinity receptor), FV (heterozygote), VV (high affinity receptor).

MabThera (Rituximab) was used as a control antibody. The control and test antibodies were titrated in triplicates in a 96-well plate. Blood from healthy donor was collected in vacuum tubes with Li-heparin. The tubes were incubated for 30 min at room temperature. 10 µl of prepared antibody solutions and 190 µl of whole blood were added to a 96-well plate with side groove (Eppendorf). 5 ml of DPBS was added to the side groove of the 96-well plate. The plate was stirred on an orbital shaker (2 mm) for 2 min at 600 rpm, and then incubated in a $CO_2$ incubator for 22 hours.

After the time of incubation, the samples were stained with fluorescent-labeled antibodies against CD45, CD3/CD19 (BD Pharmingen) for 1 hour. We fixed the cells and lysed erythrocytes using BD Pharmingen lysis buffer, washed twice from lysis buffer in Stain Buffer (DPBS, 0.1% NaN3, 0.5% BSA) and measured the number of CD45+CD3+ and CD45+CD19+ events (at least 10,000 events within gate CD45+). Data was analyzed using the InCyte module of guavaSoft 3.1.1 software.

Relative B cell depletion was measured using B-/T-cell ratio of a point without antibodies (number of B cells is taken as 100%=0% B cell depletion). B-/T-cell ratio was calculated using the following formula:

$$B-/T-\text{cell ratio} = \frac{\text{number of } B \text{ cells}}{\text{number of } T \text{ cells}}$$

Percent of B cell depletion was calculated using the following formula:

$$B\text{-cell depletion, \%} = 100 - \left(\frac{100}{B/T - \text{cell ratio without antibody}} * B/T - \text{cell ratio with antibody}\right)$$

Statistical environment R with the extension package drc was employed to plot four-parameter curves.

The test antibodies BCD-132-L-028 and BCD-132-L-077 show a significantly higher activity as compared to MabThera (Rituximab). Thus, when using donated blood of allotype FF, BCD-132-L-028 and BCD-132-L-077 induce depletion of about 50% of CD19+ cells, whereas MabThera (Rituximab) induce depletion of about 20%. The ED50 values of MabThera (Rituximab) are significantly higher than those of BCD-132-L-028 and BCD-132-L-077 when using donated blood of CD16 allotype FV and VV. The level of B cell depletion of BCD-132-L-028 and BCD-132-L-077 does not depend on donor CD16 allotype. The results are shown in FIG. 32.

Example 18. Antibody-Dependent Cellular Cytotoxicity (ADCC) Activity Assay of Anti-CD20 Antibody Candidates on Ramos Cell Line Using Human Peripheral Blood Mononuclear Cells (PBMCs)

CD-20-expressing Ramos cell line and PBMCs from healthy donors were employed for the ADCC assay. Ramos cells were cultured in RPMI-1640 medium supplemented with 10% FBS (fetal bovine serum) at 37° C. 5% $CO_2$, the cell were stained with fluorescent dye Calcein AM which may escape only from cells with a damaged cell wall. A suspension of cells at a density of $10^5$ cells/ml was prepared in RPMI-1640 medium supplemented with 10% FBS.

PBMCs were isolated from venous blood from healthy donors by Ficoll density gradient separation (1.077 $g/cm^3$). A suspension of cells at a density of $5*10^6$ cells/ml was prepared in RPMI-1640 medium supplemented with 10% FBS.

A series of antibody dilutions was added to the wells of a 96-well plate at 50 µl/well for the ADCC assay. 100 µl/well of Ramos suspension and 50 µl/well of PBMC suspension were added to them. The plate was incubated for 4 hours at 37° C. with 5% $CO_2$. 30 minutes before the end of incubation, 10 µl/well of 10% Tryton X-100 was added to maximal lysis wells. Following incubation, 100 µl/well of cellular fluid was transferred without taking the cells to a new plate. Fluorescence was measured at excitation/emission wavelength of 485/538 nm.

ADCC efficacy was calculated using the following formula:

$$ADCC = \frac{\text{Exeperimental data} - \text{background}}{\text{Full lysis} - \text{background}} \times 100\%$$

Based on ADCC as a function of antibody concentration, we determined the dependence described by 4-parameter equation using GraphPad Prism 6.0 software package and calculated the half-maximal effective concentration (EC50).

According to the ADCC assay, anti-CD20 antibody candidates BCD-132-L-028 and BCD-132-L-077 show better performance than that of Rituximab. The results are shown in FIG. 33.

Example 19. Study of activity of BCD132-L-077 monoclonal antibody product following repeated intravenous administration in cynomolgus monkeys (*Macaca fascicularis*) on a model of experimental autoimmune encephalomyelitis (EAE).

The study was performed in males of cynomolgus monkeys (*Macaca fascicularis*). Total of 12 animals were involved in the experiment, each group including 4 monkeys. We used two product doses in the experiment: 5 mg/kg; 22 mg/kg, animals in the control group received a placebo product. Data for the animal experimental groups is given in Table 2.

TABLE 2

| Groups of Animals. | | | | |
|---|---|---|---|---|
| Group no. | Animal qty | Product | Route of administration | Dose |
| 1 | 4 (♂) | BCD132-L-077 | IV | 5 mg/kg |
| 2 | 4 (♂) | | | 22 mg/kg |
| 3 | 4 (♂) | Placebo | | — |

To induce experimental autoimmune encephalomyelitis in *M. fascicularis*, a modified technique was used, which has been described in a number of publications. To sensitize primates, we used a recombinant protein from JSC «BIOKAD», which is the extracellular domain of the human myelin oligodendrocyte protein (rhMOG, amino acids 1-125).

Each animal was injected three times with an emulsion containing 400 µg of protein in 400 µl of phosphate-buffered saline mixed with 400 µl of Freund's complete adjuvant. Immediately after the first administration of rhMOG, the monkeys were injected with a heat-inactivated *B. pertussis* vaccine.

First Administration of rhMOG

To prepare the emulsion, 10 mg of rhMOG was dissolved in 10 ml of phosphate-buffered saline. 10 ml of Freund's complete adjuvant was added to the resulting solution.

The resulting emulsion was administered subcuticularly by 100 µl injections at 8 points (total administered volume per monkey is 800 µl):
 4 injections into spinal area (between shoulder blades, 2 on the right side and 2 on the left side of spinal cord);
 2 injections into groin area (1 on the right side and 1 on the left side);
 2 injections into axillary space (1 on the right side and 1 on the left side);

Following the first administration of rhMOG, $10^{10}$ inactivated *B. pertussis* particles were administered intravenously.

The interval between the first and second immunization was 28 days.

Second Administration of rhMOG

To prepare the emulsion, 10 mg of rhMOG was dissolved in 10 ml of phosphate-buffered saline. 10 ml of Freund's complete adjuvant was added to the resulting solution.

The resulting emulsion was administered subcuticularly by 100 µl injections at 8 points (total administered volume per monkey is 800 µl):
 4 injections into spinal area (between shoulder blades, 2 on the right side and 2 on the left side of spinal cord);
 2 injections into groin area (1 on the right side and 1 on the left side);
 2 injections into axillary space (1 on the right side and 1 on the left side);

The interval between the second and third immunization was 14 days

Third Administration of rhMOG

To prepare the emulsion, 10 mg of rhMOG was dissolved in 10 ml of phosphate-buffered saline. 10 ml of Freund's complete adjuvant was added to the resulting solution.

The resulting emulsion was administered subcuticularly by 100 µl injections at 8 points (total administered volume per monkey is 800 µl):

4 injections into spinal area (between shoulder blades, 2 on the right side and 2 on the left side of spinal cord);

2 injections into groin area (1 on the right side and 1 on the left side);

2 injections into axillary space (1 on the right side and 1 on the left side);

Assessment of efficacy of BCD132-L-077 product on a model of experimental autoimmune encephalomyelitis (EAE)

To measure the product activity, a histological examination of brain and spinal cord tissues was carried out. Severity of inflammatory reaction in spinal cord and brain tissues was scored on a three-point scale according to Table 3.

TABLE 3

Inflammatory reaction severity scale

| Score | Inflammatory severity |
|---|---|
| 0 | no signs of inflammation; |
| 1 | rare (1-3 per section) foci of perivascular infiltration; |
| 2 | moderate frequency (4-10 per section) of foci of perivascular infiltration; possible inflammation of the meninges; |
| 3 | ubiquitous foci of perivascular infiltration and inflammatory cell infiltration of neural tissue. |

Severity of degenerative changes in primates' spinal cord and brain tissues was scored on a scale as shown in Table 4.

TABLE 4

Spinal cord/brain tissue demyelination severity scale

| Score | Demyelination severity |
|---|---|
| 0 | no signs of demyelination; |
| 1 | rare (1-3 per section) foci of demyelination; |
| 2 | moderate frequency (4-10 per section) of foci of demyelination; |
| 3 | ubiquitous demyelination with large confluent foci. |

The results of inflammation severity measurements are shown in FIG. 34. It has been shown that with the administration of 5.0 mg/kg and 22.0 mg/kg doses used in the study, there was a decrease in the total group score as compared to the control group (sham control). The detected changes were not reliable. Also, there was no significant difference between the experimental groups. Thus, one can talk of anti-inflammatory effect efficacy that is comparable for the two tested doses of the product.

The results of measurement of severity of degenerative changes in neural tissue are shown in FIG. 35. When using the test product BCD132-L-077 at a minimum dose of 5.0 mg/kg, we observed a significant decrease in demyelination score as compared to that of the control.

An animal group that received the product at a dose of 22.0 mg/kg also showed a decrease in the value of parameter in question, but it was not reliable. There was no significant difference in the values between the experimental groups; thus, one can conclude that the level of activity of the two doses is comparable.

The study showed that the product at doses of 5.0 mg/kg and 22.0 mg/kg shows anti-inflammatory effect that is comparable in terms of efficacy, and reduces to a similar extent the level of demyelination in neural tissue of experimental primates. Based on the above data, a dose of 5.0 mg/kg can be established as a pharmacologically active dose (FAD).

Example 20. Study of Toxicity and Main Pharmacokinetic Parameters (Toxicokinetics) of BCD132-L-077 Following Multiple Subcutaneous Administration in Cynomolgus Monkeys (*Macaca fascicularis*)

The study was performed in males of cynomolgus monkeys (*Macaca fascicularis*). After quarantine, the animals were divided into four experimental groups, each group comprising three males, in accordance with the doses of the product to be administered; body weight was used as a criterion to distribute the monkeys in groups. We used three product doses in the experiment: 44 mg/kg; 88 mg/kg; 176 mg/kg, animals in the control group received a placebo product. Condition of animals, number of dead animals and the timing of their death were used as evaluation criteria. The animals were observed for 8 hours after injection, and then daily for 42 days.

Data for animal experimental groups and product doses is given in Table 5:

TABLE 5

Groups of animals in the study of efficacy of BCD132-L-077 product

| Group no. | Animal qty | Product | Route of administration | Dose |
|---|---|---|---|---|
| 1 | 3 (♂) | BCD132-L-077 | IV | 44 mg/kg |
| 2 | 3 (♂) | | | 88 mg/kg |
| 3 | 3 (♂) | | | 176 mg/kg |
| 4 | 3 (♂) | Placebo | | — |

Condition of animals, number of dead animals and the timing of their death were used as evaluation criteria.

Within the bounds of the study, clinical examination was performed 8 hours after injection, and then daily; furthermore, we evaluated the following:

animal weight;
body temperature;
urinalysis;
complete blood analysis on the following parameters: number of erythrocytes, number of white blood cells, hemoglobin concentration;
biochemical analysis of blood serum on the following parameters: lactate dehydrogenase, total bilirubin, total protein, glucose, aspartate aminotransferase, alanine aminotransferase;
product concentration in blood serum.

According to the studies, the test product does not induce death of *M. fascicularis* following a single intravenous administration, the experimental animals tolerate the administration process well. The product did not show any effect on integral toxicity indicators, and on functional state of organs according to the parameters in question. In the selected dose range, the product exhibits linear pharmacokinetics.

Example 21. Study of Pharmacokinetics and Immunogenicity Following Repeated Intravenous Administration of BCD132-L-077 Product in Cynomolgus Monkeys (*Macaca fascicularis*) for Four Weeks Followed by a Recovery Period for Two Weeks Pharmacokinetics and immunogenicity following repeated intravenous administration were studied using doses of 22.0, 44.0 and 88.0 mg/kg. Total of 18 sexually mature monkeys, 9 female monkeys and 9 male monkeys (*Macaca fascicularis*) aged 4 to 7 years, were involved in the study. The animals were divided into 3 groups based on the dose of product to be administered.

TABLE 6

Groups of Animals.

| Group no. | Animal qty | Product | Route of administration | Dose |
|---|---|---|---|---|
| 1 | 3 (♂) 3 (♀) | BCD132-L-077 | IV | 22 mg/kg |
| 2 | 3 (♂) 3 (♀) | | | 44 mg/kg |
| 3 | 3 (♂) 3 (♀) | | | 88 mg/kg |

Level of BCD132-L-077 in primates' blood serum was measured by enzyme-linked immunosorbent assay. During the study, in order to establish the possible effect of formation of product-binding antibodies on pharmacokinetic parameters, the immunogenicity of BCD132-L-077 product was measured. Also, we calculated an accumulation factor from the ratio $AUC_{ss168\ (336-504)}:AUC_{0-168}$.

To calculate the $AUC_{0-168}$ value, serum was taken immediately before the first administration of product, and then after 0.25, 24, 72 and 168 hours after administration; to calculate the $AUCss_{168\ (336-504)}$ value, serum was taken immediately before the fourth administration of product, and then 0.25, 24, 72 and 168 hours after administration. The pharmacokinetic parameters were calculated based on data only from those animals in which BAbs were not detected. Thus, data from animals that showed immune response to product was excluded from the calculation of pharmacokinetic parameters. Product accumulation was measured by accumulation index; to this end, $AUC_{0-168}$ and $AUCss_{(336-504)}$ values were determined and the index was calculated by the following formula:

$$R = \frac{AUC_{SS168(336-504)}}{AUC_{0-168}},$$

where $AUCss_{168\ (336-504)}$ is equilibrium value of area under product concentration-time curve over a period corresponding to dosage interval (168 h) under repeated administration;

$AUC_{0-168}$ is area under product concentration-time curve from the moment the product was introduced into a body to 168 hours following first administration.

To analyze the level of antibodies binding BCD132-L-077 product, we used primates' blood serum. Samples for the study were taken before the first administration, and then at 4 and 7 weeks of the experiment.

Example 22. Comparison of Pharmacokinetic Parameters Under Repeated Intravenous Administration of Increasing Doses (22.0 mg/kg, 44.0 mg/kg, 88.0 mg/kg) of BCD132-L-077 Product FIG. 36 shows smoothed BCD132-L-077 product concentration-time curves for primates' blood serum. Table 7 shows average values of main pharmacokinetic parameters for groups.

TABLE 7

Comparative data for main pharmacokinetic parameters under administration of increasing doses of BCD132-L-077 product (steady-state (ss) values were calculated using a period of 336-504 hours which corresponds to a dosage interval (168 hours).

| | | Dose (mg/kg) | | | | | |
|---|---|---|---|---|---|---|---|
| | | 22 µg/ml | | 44 µg/ml | | 88 µg/ml | |
| PK parameter | Unit | Xmean | σ | Xmean | σ | Xmean | σ |
| AUCss (0-168) | µg/ml × h | 13435.59 | 11150.8 | 13301.04 | 8719.1 | 34145.90 | 16765.5 |
| AUCss (336-504) | µg/ml × h | 26227.47 | 16819.4 | 22366.93 | 10370.6 | 97088.33 | 94675.6 |
| Css (min) | µg/ml | 82.64 | 75.2 | 84.58 | 63.9 | 162.88 | 74.7 |
| Css (max) | µg/ml | 326.89 | 241.7 | 427.03 | 266.5 | 1212.72 | 830.9 |
| Css | µg/ml | 156.12 | 100.1 | 133.14 | 61.7 | 577.91 | 563.5 |
| T ½ | h | 94.76 | 50.3 | 155.38 | 111.2 | 471.00 | 782.5 |
| Cl | l/h | 0.00924 | 0.004 | 0.01873 | 0.015 | 0.01228 | 0.005 |
| CLss | ml/h | 4.550 | 2.37 | 10.323 | 6.33 | 7.352 | 5.70 |
| Vss | ml | 521.65 | 186.9 | 1639.68 | 1170.5 | 2384.08 | 2213.3 |
| MRTlast | h | 66.37 | 13.6 | 68.30 | 17.5 | 71.51 | 9.2 |

Pharmacokinetic parameters of BCD132-L-077 product were calculated using steady-state AUC values in a dosing period of 336-504 hours (168 hours) following product administration. Initial AUC calculated in a first dosing interval (1-168 hours) was in direct relationship to the dose used. In the minimal-dose group, this parameter was 13,435.59±11,150.80 (µg/ml) hour; in the average-dose group: 13,301.04±8,719.10 (µg/ml) hour; and in the maximal-dose group: 34,145.90±16,765.50 (µg/ml) hour. AUC calculated in steady-state state (336-504 hours) also depended on the dose used. AUCss168 (336-504) was 26,227.47±16,819.40 (µg/ml) hour in animal group which received the product at a dose of 22 mg/kg; the value was 22,366.93±10,370.60 (µg/ml) hour in the average-dose group, and 97,088.33±94,675.60 (µg/ml) hour in the maximal-dose group. The half-life value (T½) was 94.76±50.30 hours in the animal group which received the product at a dose of 22 mg/kg, 155.38±111.20 hours in the average-dose group, and 471.00±782.50 hours in the maximal-dose group. The clearance was 0.00924±0.004 l/h in the minimal-dose group, 0.01873±0.015 l/h in the average-dose group, and 0.01228±0.005 l/h in the maximal-dose group. The product's mean residence time (MRT) was 66.37±13.60 h in the minimal-dose group, 68.30±17.50 h in the average-dose group, and 71.51±9.20 hours. The steady state volume of distribution ($V_{dss}$) was 521.65±186.90 ml/kg, 1,639.68±1,170.50 ml/kg, 2,384.08±2,213.30 ml/kg in minimal-, average- and maximal-dose groups, respectively. The average steady state concentration ($C_{ss}$) was 156.12±100.10 µg/ml, 133.14±61.70 µg/ml, 577.91±563.50 µg/ml in minimal-, average- and maximal-dose groups, respectively. The maximal steady state concentration ($C_{ssmax}$) was 326.89±241.70 µg/ml, 427.03±266.50 µg/ml, 1,212.72±830.90 µg/ml. The minimal steady state concentration ($C_{ssmin}$) was 82.64±75.20 µg/ml, 84.58±63.90 µg/ml, 162.88±74.70 µg/ml. The data obtained indicate that the product concentration in primates' blood serum is in direct relationship to the BCD132-L-077 dose used in the experiment.

For animal group that received the product at a minimal dose of 22.0 mg/kg, accumulation index (R) was 1.95. For animal group that received BCD-132 at an average dose of 44.0 mg/kg, accumulation index R was 1.68. For animal group that received the product at a maximal dose (88.0 mg/kg), index R was 2.84. The experimental data obtained indicate that accumulation index value does not depend on the dose used.

During the study, in order to establish the possible effect of formation of product-binding antibodies on pharmacokinetic parameters, the immunogenicity of BCD132-L-077 product was measured. Experimental data indicate the presence of BAbs in 11.11% of all animals involved in the study. No sex dependence was found; BAbs were observed in one male and one female. Product-binding antibodies were found in average- and maximal-dose groups, in only one animal from each group. Pharmacokinetic parameters can be evaluated in all animal groups, provided that experimental data for animals for which the presence of binding antibodies was established are excluded from processing.

Example 23. Study of Toxicity and Local Irritant Effect Following Repeated Intravenous Administration of BCD132-L-077 Product in Cynomolgus Monkeys (*Macaca fascicularis*) for Four Weeks Followed by a Recovery Period for Two Weeks Total of 30 cynomolgus monkeys (*Macaca fascicularis*), aged 4 to 7 years, 15 males and 15 females, were involved in the experiment. Each group included 6 monkeys. Product toxicity under repeated administration was studied at doses of 22 mg/kg, 44 mg/kg and 88 mg/kg. The animals were divided into 5 groups according to the dose of product to be administered and time to euthanasia:

BCD132-L-077 product at a minimal dose of 22 mg/kg (3 females and 3 males);

BCD132-L-077 product at an average dose of 44 mg/kg (3 females and 3 males);

BCD132-L-077 product at a maximal dose of 88 mg/kg, euthanasia after the end of administration (3 females and 3 males);

BCD132-L-077 product at a maximum dose of 88 mg/kg, euthanasia after the end of recovery period (3 females and 3 males);

Sham control (3 females and 3 males).

Data for the animal experimental groups are shown in Table 8.

TABLE 8

| Groups of Animals. | | | | |
|---|---|---|---|---|
| Group No. | Animal Qty | Product | Route of administration | Dose |
| 1 | 3 (♂) 3 (♀) | BCD132-L-077 | IV | 22 mg/kg |
| 2 | 3 (♂) 3 (♀) | | | 44 mg/kg |
| 3 | 3 (♂) 3 (♀) | | | 88 mg/kg |
| 3* | 3 (♂) 3 (♀) | | | 88 mg/kg |
| 4 | 3 (♂) 3 (♀) | Placebo | | — |

3* - satellite group,
3 - main group

Within the bounds of the study, clinical examinations were performed daily; furthermore, we examined the following:

animal weight;
body temperature;
urinalysis;
ECG;
hemostasis parameters: activated partial thromboplastin time, fibrinogen concentration, prothrombin time;
complete blood analysis on the following parameters: number of erythrocytes, number of white blood cells, hemoglobin concentration, lymphocytes, monocytes, neutrophils, eosinophils, basophils;
biochemical analysis of blood serum on the following parameters: lactate dehydrogenase, total bilirubin, total protein, glucose, aspartate aminotransferase, alanine aminotransferase, cholesterol, triglycerides, urea, createnine, sodium, potassium, alkaline phosphatase;
pathomorphological and histological studies.

Local irritant effect was evaluated on the basis of examination data and results of histological examination. Tissues at the administration site and draining lymph nodes were selected for histological examination.

According to histological examination, the test product does not show a local irritant effect.

The data obtained in the study of toxicity of BCD132-L-077 therapeutic monoclonal antibody product produced by JSC «BIOKAD» indicate that the test product does not exhibit toxic effects on major organs and organ systems of experimental animals under repeated weekly intravenous administration for 4 weeks. No observed adverse effect level (NOAEL) as established in this study corresponds to the maximal dose of the test product BCD132-L-077 and amounts to 88 mg/kg.

Example 24. Study of Antitumor Activity of BCD132-L-028 Product Following Repeated Intraperitoneal Administration in Immunodeficient hIL15-NOG Mice Humanized with Human NK Cells on a Model of Subcutaneous Xenograft Using the Raji Human Lymphoma Cell Line In the study, we plan to use 7 groups of immunodeficient transgenic hIL15-NOG mice constitutively expressing human IL-15, and weighing 15.0-25.0 g. Total of 84 female animals were involved in the experiment. Data for the groups are shown in Table 9.

TABLE 9

Groups of Animals.

| Group No. | Total of animals in group | Product | Cell Line | Qty of inoculated NK cells | Route of administration | Dose, mg/kg |
|---|---|---|---|---|---|---|
| 1 | 12 (♀) | BCD132-L-023 | Raji | IV - 6*10⁶ cells | IP | 10 mg/kg |
| 2 | 12 (♀) | BCD132-L-023 | | | | 30 mg/kg |
| 3 | 12 (♀) | BCD132-L-023 | | | | 90 mg/kg |
| 4 | 12 (♀) | Obinutuzumab | | | | 30 mg/kg |
| 5 | 12 (♀) | Acellbia | | | | 30 mg/kg |
| 6 | 12 (♀) | Placebo | | — | | |
| 7 | 12 (♀) | Placebo | | | | |

Animals are weighed before administration of tumor cell line, and then 2 times a week throughout the experiment.

Tumor nodule is measured after administration of tumor cells 2 times a week throughout the experiment.

Volume of tumor nodule is calculated by the following formula:

$V = \pi/6 \times L \times W \times H$, where $L, W, H$ are tumor linear dimensions.

The efficacy of the test product is assessed by the index of tumor growth inhibition (TGI) vs the index of tumor growth (I). The indices are calculated by the following formula:

$$TGI(\%) = \frac{V_k - V_o}{V_k} \times 100,$$

Where $V_k$ and $V_o$ are median tumor volume (MM³) in control and treated groups, respectively.

$I_i = V_i/V_o,$ where I is the index of tumor growth, i is the day of experiment, $V_o$ is tumor volume per day.

Example 25. Study of Toxicity and Main Pharmacokinetic Parameters (Toxicokinetics) of BCD132-L-028 Monoclonal Antibody Product Following a Single Intravenous Administration in Cynomolgus Monkeys (*Macaca fascicularis*)

In the study, we plan to use four experimental groups of cynomolgus monkeys, each group including three males. The monkeys will be kept in individual cages with indication of animal number according to the experiment.

The animals are randomly assigned to groups according to doses of substance to be administered, using body weight as a criterion.

TABLE 10

Groups of Animals.

| Group no. | Animal qty | Product | Route of administration | Dose, mg/kg |
|---|---|---|---|---|
| 1 | 3 (♂) | BCD132-L-028 | IV | 20 |
| 2 | 3 (♂) | | | 40 |
| 3 | 3 (♂) | | | 80 |
| 4 | 3 (♂) | Placebo | | — |

Products are planned to be administered intravenously in an ulnar vein as sterile isotonic saline solutions. The animals of the control group will be administered (placebo) with isotonic saline using the same volumes and method as those used in the experimental groups.

Within the bounds of the study, clinical examination is performed daily; furthermore, we examine the following:
1. animal weight;
2. body temperature;
3. urinalysis;
4. complete blood analysis on the following parameters: number of erythrocytes, number of white blood cells, hemoglobin concentration;
5. biochemical analysis of blood serum on the following parameters: lactate dehydrogenase, total bilirubin, total protein, glucose, aspartate aminotransferase, alanine aminotransferase;
6. study of product concentration in blood serum, calculation of main pharmacokinetic parameters, and evaluation of pharmacokinetics linearity.

Example 26. Study of Pharmacokinetics and Immunogenicity Following Repeated Intravenous Administration of BCD132-L-028 Monoclonal Antibody Product in Cynomolgus Monkeys (*Macaca fascicularis*) for 13 Weeks Followed by a Recovery Period for 30 Days In the study of pharmacokinetics and immunogenicity following repeated intravenous administration for 13 weeks followed by a recovery period for 30 days, we plan to use 18 cynomolgus monkeys (9 males and 9 females).

The animals will be assigned to 3 groups (Table 11) according to the doses of substance to be administered, each group including 3 females and 3 males: minimal-dose group (6 mg/kg), intermediate-dose group (20 mg/kg), maximal-dose group (60 mg/kg).

TABLE 11

Groups of Animals.

| Group no. | Total of animals in group | Product | Route of administration | Dose, mg/kg |
|---|---|---|---|---|
| 1 | 3 (♂)<br>3 (♀) | BCD132-L-028 | IV | 6 |
| 2 | 3 (♂)<br>3 (♀) | | | 20 |
| 3 | 3 (♂)<br>3 (♀) | | | 60 |

In the study, we plan to:
1. evaluate the test product concentration in blood serum of experimental animals;

2. evaluate the test product accumulation under administration of increasing doses;
3. evaluate the level of binding antibodies under repeated intravenous administration of the test product.

Example 27. Study of Toxicity and Local Irritant Effect Following Repeated Intravenous Administration of BCD132-L-028 Monoclonal Antibody Product in Cynomolgus Monkeys (*Macaca fascicularis*) for 13 Weeks Followed by a Recovery Period for 30 Days In the study, we plan to use 5 experimental groups of cynomolgus monkeys, each group including 3 males and 3 females: minimal-dose group (6 mg/kg, without necropsy), intermediate-dose group (20 mg/kg, without necropsy), satellite maximal-dose group (60 mg/kg, necropsy after the end of product administration period), main maximal-dose group (60 mg/kg, necropsy after the end of recovery period) and sham control group (necropsy after the end of recovery period).

TABLE 12

Groups of Animals (* - animal from satellite group)

| Group no. | Animal qty | Product | Route of administration | Dose, mg/kg |
|---|---|---|---|---|
| 1 | 3 (♂) 3 (♀) | BCD132-L-028 | IV | 6 |
| 2 | 3 (♂) 3 (♀) | | | 20 |
| 3 | 3 (♂) 3 (♀) 3 (♂) 3 (♀) | | | 60 |
| 4 | 3 (♂) 3 (♀) | Placebo | | — |

Clinical examination of each animal will be performed daily; furthermore, we will evaluate the following:
animal weight;
body temperature (before administration and then weekly until termination of the experiment);
effect on the cardiovascular system using Poly-Spectr cardiograph;
urinalysis;
complete blood analysis on the following parameters: number of erythrocytes, number of leukocytes, hemoglobin concentration, number of lymphocytes, number of monocytes, number of neutrophils, number of eosinophils, number of basophils;
evaluation of effect on blood coagulation system on the following parameters: activated partial thromboplastin time, fibrinogen concentration, prothrombin time;
biochemical analysis of blood serum on the following parameters: sodium, potassium, creatinine, urea, alkaline phosphatase, lactate dehydrogenase, total bilirubin, total protein, glucose, triglycerides, aspartate aminotransferase, alanine aminotransferase, total cholesterol;

At the end of product administration period (week 14), we plan to euthanize three males and three females from each animal group. The remaining two males and two females in each group will be euthanized at the end of recovery period (week 18). Local irritant effect will be evaluated on the basis of necropsy data and results of histological examination. For histological examination, we will select a section of ulnar vein, tissues at the administration site and draining lymph nodes.

The invention claimed is:

1. A monoclonal antibody or antigen-binding fragment thereof that specifically binds to CD20, comprising:
   i) a heavy chain variable domain comprising the amino acid sequence shown in SEQ ID NO: 2, and a light chain variable domain comprising the amino acid sequence shown in SEQ ID NO: 4; or
   ii) a heavy chain variable domain comprising the amino acid sequence shown in SEQ ID NO: 6, and a light chain variable domain comprising the amino acid sequence shown in SEQ ID NO: 8.

2. A monoclonal antibody according to claim 1, comprising:
   i) a heavy chain comprising the amino acid sequence shown in SEQ ID NO: 1, and a light chain comprising the amino acid sequence shown in SEQ ID NO: 3; or
   ii) a heavy chain comprising the amino acid sequence shown in SEQ ID NO: 5, and a light chain comprising the amino acid sequence shown in SEQ ID NO: 7.

3. A monoclonal antibody according to claim 1, wherein the antibody is a full-length IgG antibody.

4. A monoclonal antibody according to claim 3, wherein the full-length IgG antibody relates to human IgG1, IgG2, IgG3, or IgG4 isotype.

5. A monoclonal antibody according to claim 4, wherein the full-length IgG antibody relates to human IgG1 isotype.

6. A pharmaceutical composition comprising an antibody or antigen-binding fragment thereof according to claim 1 in combination with one or more pharmaceutically acceptable excipients.

7. A pharmaceutical composition comprising an antibody or antigen-binding fragment thereof according to claim 1 and at least one different therapeutically active compound.

8. A pharmaceutical composition according to claim 7, wherein the at least one different therapeutically active compound is an antitumor compound selected from a chemotherapeutic agent, an antibody, or anti-hormonal agent.

9. A method for inhibiting biological activity of CD20 in a subject in need thereof, comprising administering to the subject an effective amount of an antibody or antigen-binding fragment thereof according to claim 1.

10. A method for treating a disease or disorder mediated by CD20 in a subject in need thereof, comprising administering to the subject an effective amount of an antibody or antigen-binding fragment according to claim 1.

11. The method according to claim 10, wherein the disease or disorder is selected from:
    a) an oncological disease or disorder; and
    b) an autoimmune disease or disorder.

12. The method according to claim 11, wherein the oncological disease or disorder is selected from B cell lymphoma and leukemia.

13. The method according to claim 12, wherein the B cell lymphoma is selected from non-Hodgkin lymphoma (NHL), Hodgkin's disease (Hodgkin's lymphoma), chronic lymphocytic leukemia (CLL), and small lymphocytic lymphoma (SLL).

14. The method according to claim 11, wherein the autoimmune disease or disorder is selected from rheumatoid arthritis, juvenile rheumatoid arthritis (Still's disease), systemic lupus erythematosus (SLE), lupus nephritis, ulcerative colitis, Wegener's disease, inflammatory bowel disease, idiopathic thrombocytopenia purpura (ITP), thrombotic thrombocytopenia purpura (TTP), autoimmune thrombocytopenia, multiple sclerosis, psoriasis, IgA nephropathy, IgM polyneuropathies, myasthenia gravis, vasculitis, ANCA vasculitis, rejection of graft of parenchymatous organs, graft-versus-host disease (GvHD), diabetes mellitus, Raynaud's syndrome, Sjorgen's syndrome, and glomerulonephritis.

* * * * *

SEQUENCE LISTING

```
<160> NUMBER OF SEQ ID NOS: 8

<210> SEQ ID NO 1
<211> LENGTH: 451
<212> TYPE: PRT
<213> ORGANISM: Artificial sequence
<220> FEATURE:
<223> OTHER INFORMATION: synthesized

<400> SEQUENCE: 1

Glu Val Gln Leu Val Gln Pro Gly Ala Glu Val Val Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Arg Gly Leu Glu Trp Met
            35                  40                  45

Gly Ala Ile Tyr Pro Gly Asn Gly Asp Thr Ser Tyr Asn Gln Lys Phe
        50                  55                  60

Lys Gly Arg Val Thr Met Thr Arg Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
```

```
                100               105               110
Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 2
<211> LENGTH: 121
<212> TYPE: PRT
<213> ORGANISM: Artificial sequence
<220> FEATURE:
<223> OTHER INFORMATION: synthesized

<400> SEQUENCE: 2

Glu Val Gln Leu Val Gln Pro Gly Ala Glu Val Val Lys Pro Gly Ala
```

```
                 1               5                  10                 15
            Ser Val Lys Val Ser Cys Lys Ala Ser Gly Tyr Thr Phe Thr Ser Tyr
                        20                  25                  30

Asn Met His Trp Val Arg Gln Ala Pro Gly Arg Gly Leu Glu Trp Met
                        35                  40                  45

Gly Ala Ile Tyr Pro Gly Asn Gly Asp Thr Ser Tyr Asn Gln Lys Phe
                        50                  55                  60

Lys Gly Arg Val Thr Met Thr Arg Asp Lys Ser Thr Ser Thr Val Tyr
             65                  70                  75                  80

Met Glu Leu Ser Ser Leu Arg Ser Glu Asp Thr Ala Val Tyr Tyr Cys
                        85                  90                  95

Ala Arg Ser Thr Tyr Tyr Gly Asp Trp Tyr Phe Asn Val Trp Gly
                        100                 105                 110

Gln Gly Thr Leu Val Thr Val Ser Ser
                        115                 120

<210> SEQ ID NO 3
<211> LENGTH: 213
<212> TYPE: PRT
<213> ORGANISM: Artificial sequence
<220> FEATURE:
<223> OTHER INFORMATION: synthesized

<400> SEQUENCE: 3

Gln Ile Val Leu Ser Gln Ser Pro Ala Ile Leu Ser Ala Ser Pro Gly
 1               5                  10                  15

Glu Arg Val Thr Leu Thr Cys Arg Ala Ser Ser Ser Val Ser Tyr Ile
            20                  25                  30

His Trp Phe Gln Gln Lys Pro Gly Lys Ala Pro Lys Pro Leu Ile Tyr
            35                  40                  45

Ala Thr Ser Asn Leu Ala Ser Gly Val Pro Ser Arg Phe Ser Gly Ser
            50                  55                  60

Gly Ser Gly Thr Asp Phe Ser Leu Thr Ile Ser Arg Val Glu Pro Glu
 65                  70                  75                  80

Asp Phe Ala Val Tyr Tyr Cys Gln Gln Trp Thr Ser Asn Pro Pro Thr
                        85                  90                  95

Phe Gly Gly Gly Thr Lys Val Glu Ile Lys Arg Thr Val Ala Ala Pro
                        100                 105                 110

Ser Val Phe Ile Phe Pro Pro Ser Asp Glu Gln Leu Lys Ser Gly Thr
                        115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                        165                 170                 175

Thr Leu Thr Leu Ser Lys Ala Asp Tyr Glu Lys His Lys Val Tyr Ala
                        180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 4
<211> LENGTH: 106
<212> TYPE: PRT
```

```
<213> ORGANISM: Artificial sequence
<220> FEATURE:
<223> OTHER INFORMATION: synthesized

<400> SEQUENCE: 4

Gln Ile Val Leu Ser Gln Ser Pro Ala Ile Leu Ser Ala Ser Pro Gly
1               5                   10                  15

Glu Arg Val Thr Leu Thr Cys Arg Ala Ser Ser Val Ser Tyr Ile
            20                  25                  30

His Trp Phe Gln Gln Lys Pro Gly Lys Ala Pro Lys Pro Leu Ile Tyr
            35                  40                  45

Ala Thr Ser Asn Leu Ala Ser Gly Val Pro Ser Arg Phe Ser Gly Ser
50                  55                  60

Gly Ser Gly Thr Asp Phe Ser Leu Thr Ile Ser Arg Val Glu Pro Glu
65                  70                  75                  80

Asp Phe Ala Val Tyr Tyr Cys Gln Gln Trp Thr Ser Asn Pro Pro Thr
                85                  90                  95

Phe Gly Gly Gly Thr Lys Val Glu Ile Lys
            100                 105

<210> SEQ ID NO 5
<211> LENGTH: 451
<212> TYPE: PRT
<213> ORGANISM: Artificial sequence
<220> FEATURE:
<223> OTHER INFORMATION: synthesized

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Arg Gly Leu Glu Trp Met
            35                  40                  45

Gly Ala Ile Tyr Pro Gly Asn Gly Asp Thr Ser Tyr Asn Gln Lys Phe
50                  55                  60

Lys Gly Arg Ala Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 6
<211> LENGTH: 121
<212> TYPE: PRT
<213> ORGANISM: Artificial sequence
<220> FEATURE:
<223> OTHER INFORMATION: synthesized

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Arg Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Ala Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Gln Gly Thr Leu Val Thr Val Ser Ser
        115                 120
```

```
<210> SEQ ID NO 7
<211> LENGTH: 213
<212> TYPE: PRT
<213> ORGANISM: Artificial sequence
<220> FEATURE:
<223> OTHER INFORMATION: synthesized

<400> SEQUENCE: 7

Gln Ile Val Leu Ser Gln Ser Pro Ala Thr Leu Ser Ala Ser Pro Gly
1               5                   10                  15

Glu Arg Ala Thr Met Thr Cys Arg Ala Ser Ser Val Ser Tyr Ile
            20                  25                  30

His Trp Phe Gln Gln Lys Pro Gly Lys Ala Pro Lys Pro Leu Ile Tyr
            35                  40                  45

Ala Thr Ser Asn Leu Ala Ser Gly Val Pro Ser Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Thr Tyr Tyr Cys Gln Gln Trp Thr Ser Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 8
<211> LENGTH: 106
<212> TYPE: PRT
<213> ORGANISM: Artificial sequence
<220> FEATURE:
<223> OTHER INFORMATION: synthesized

<400> SEQUENCE: 8

Gln Ile Val Leu Ser Gln Ser Pro Ala Thr Leu Ser Ala Ser Pro Gly
1               5                   10                  15

Glu Arg Ala Thr Met Thr Cys Arg Ala Ser Ser Val Ser Tyr Ile
            20                  25                  30

His Trp Phe Gln Gln Lys Pro Gly Lys Ala Pro Lys Pro Leu Ile Tyr
            35                  40                  45

Ala Thr Ser Asn Leu Ala Ser Gly Val Pro Ser Arg Phe Ser Gly Ser
        50                  55                  60

Gly Ser Gly Thr Asp Phe Thr Leu Thr Ile Ser Arg Leu Glu Pro Glu
65                  70                  75                  80
```

```
Asp Phe Ala Thr Tyr Tyr Cys Gln Gln Trp Thr Ser Asn Pro Pro Thr
                85                  90                  95

Phe Gly Gly Gly Thr Lys Val Glu Ile Lys
            100                 105
```